United States Patent [19]

Draetta et al.

[11] Patent Number: 5,691,147
[45] Date of Patent: Nov. 25, 1997

[54] CDK4 BINDING ASSAY

[75] Inventors: Giulio Draetta; Jeno Gyuris, both of Winchester, Mass.

[73] Assignee: Mitotix, Inc., Cambridge, Mass.

[21] Appl. No.: 253,155

[22] Filed: Jun. 2, 1994

[51] Int. Cl.[6] .................................................. G01N 33/53
[52] U.S. Cl. ........................... 435/7.1; 436/501; 530/300; 530/350; 536/23.1; 536/23.5; 435/4
[58] Field of Search ..................... 435/4, 7.1; 536/23.1, 536/23.5; 530/300, 350; 436/501

[56] References Cited

PUBLICATIONS

Amerik et al. (1994) 340:25-28, FEBS Letters.
Serrano et al. (1993) 366:704-707, Nature.

*Primary Examiner*—John Ulm
*Assistant Examiner*—Kenneth A. Sorensen
*Attorney, Agent, or Firm*—Matthew P. Vincent; Beth E. Arnold; Foley, Hoag & Eliot LLP

[57] ABSTRACT

The present invention relates to the discovery of novel proteins of mammalian origin which can associate with the human cyclin dependent kinase 4 (CDK4).

1 Claim, 2 Drawing Sheets

Figure 2

| pjG4-5 clone | CDK2 | CDK3 | CDK4 | CDK5 | CDK6 | cdi1 | Rb | ΔRb | p53 | cycC | cycD1 | cycD2 | cycE |
|---|---|---|---|---|---|---|---|---|---|---|---|---|---|
| #11 | | | ‡ | + | ‡ | | | | | | | | |
| #13 | | | ‡‡ | +++ | +++ | | | | | | | | |
| #22 | | | ‡‡ | + | | | | | | | | | |
| #36 | | | ‡ | | | | + | + | ‡ | | | | |
| #61 | | | ‡‡ | + | + | | + | + | | | | | |
| #68 | | | ‡‡ | + | ‡‡ | | | | | | | | |
| #71 | | | ‡‡ | + | + | | | | | | | | |
| #75 | | | ‡ | | | | | | | | | | |
| #116 | | | ‡ | + | | | ‡ | ‡ | ‡ | | | | |
| #118 | | | ‡ | | | | | | | | | | |
| #121 | | | ‡ | | | | | | | | | | |
| #125 | | | ‡ | | | | + | + | | | | | |
| #127 | | | ‡‡ | | | + | ‡‡ | ‡‡ | ‡‡ | | | | |
| #165 | | | + | | | | + | + | + | | | | |
| #166 | | | + | + | | | ‡‡ | ‡‡ | ‡‡ | | | | |
| #190 | | | + | + | | | + | + | + | | | | |
| #193 | | | + | + | | + | + | + | ‡‡ | | | | |
| #216 | | | + | +/- | | | +/- | +/- | +/- | | | | |
| #225 | | | + | + | | | | | | | | | |
| #227 | | | + | + | | | | | | | | | |
| #267 | | | ‡‡ | + | ‡ | | ‡ | ‡ | ‡‡ | | | | |
| #269 | | | ‡‡ | + | ‡‡ | | +/- | +/- | +/- | | | | |
| #295 | | | ‡‡ | + | ‡‡ | | +/- | +/- | | | | | |
| #297 | | | + | + | | | | | | | | | |
| Cyclin D1 | ‡ | ‡ | | | | | | | | | | | |
| Cyclin D3 | +++ | +++ | | | | | | | | | ‡ | ‡ | |
| p16 | | | | | | | | | | | | | |
| p21 | +++ | +++ | + | + | | | | | | | | | |

SEQUENCE LISTING ( 1 ) GENERAL INFORMATION:

( i i i ) NUMBER OF SEQUENCES: 95

( 2 ) INFORMATION FOR SEQ ID NO:1:

( i ) SEQUENCE CHARACTERISTICS:
        ( A ) LENGTH: 1638 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GAATTCTGCG GCCGCATGGA TACAGATACA GATACATTCA CCTGTCAGAA AGATGGTCGC      60
TGGTTCCCTG AGAGAATCTC CTGCAGTCCT AAAAAATGTC CTCTCCCGGA AAACATAACA     120
CATATACTTG TACATGGGGA CGATTTCAGT GTGAATAGGC AAGTTTCTGT GTCATGTGCA     180
GAAGGGTATA CCTTTGAGGG AGTTAACATA TCAGTATGTC AGCTTGATGG AACCTGGGAG     240
CCACCATTCT CCGATGAATC TTGCAGTCCA GTTTCTTGTG GGAAACCAGA AAGTCCAGAA     300
CATCGATTTG TGGTTGGCAG TAAATACACC TTTGCAAAGC ACAATTATTT ATCAGTGTGA     360
GCCTGGCTAT GAACTGGAGG GGAACAGGGC AACGTGTCTG CCAGGAGAAC AGACAGTGGA     420
GTGGAGGGGT GGCAATATGC AAAGAGACCA GGTGTGAAAC TCCACTTGAA TTTCTCAATG     480
GGAAAGCTGA CATTGAAAAC AGGACGACTG GACCCAACGT GGTATATTCC TGCAACAGAG     540
GCTACAGTCT TGAAGGGCCA TCTGAGGCAC ACTGCACAGA AAATGGAACC TGGAGCCACC     600
CAGTCCCTCT CTGCAAACCA AATCCATGCC CTGTTCCTTT TGGTGATTCC CGAGAATGCT     660
CTGCTGTCTT GAAAGGAGT  TTTATGTTGA TCAGAATGTG TCCATCAAAT GTAGGGAAGG     720
TTTTCTGCTG CAGGGCCACG GCATCATTAC CTGCAACCCC GACGAGACGT GGACACAGAC     780
AAGCGCCAAA TGTGAAAAAA TCTCATGTGG TCCACCAGCT CACGTAGCAA AATGCAATTG     840
CTCGAGGCGT ACATTATCAA TATGGAGACA TGATCACCTA CTCATGTTAC AGTGGATACA     900
TGTTGGAGGG TTTCCTGAGG AGTGTTTGTT TAGAAAATGG AACATGGACA TCACCTCCTA     960
TTTGCAGAGC TGTCTGTCGA TTTCCATGTC AAGAATGGGG GCATCTGCCA ACGCCCAAAT    1020
GCTTGTTCCT GTCCAGAGGG CTGGATGGGG CGCCTCTTGT GAAGAACCAA TCTGCATTCT    1080
TCCCTGTCTG AACGGAGGTC GCTGTGTGGC CCCTTACCAG TGTGACTGCC CGCCTGGCTG    1140
GACGGGGTCT CGCTGTCAAA CAAGCTGTTT GCCAGTCTCC CTGCTTAAAT GGTGGAAAAT    1200
GTGTAAGACC AAACCGATGT CACTGTCTTT CTTCTTGGAC GGGACATAAC TGTTCCAGGA    1260
AAAGGAGGAC TGGGTTTTAA CCACTGCACG ACCATCTGGC TCTCCCAAA  GCAGGATCAT    1320
CTCTCCTCGG TAGTGCCTGG GCATCCTGGA ACTTATGCGA AGAAAGTCCA ACATGGTGCT    1380
GGGTCTTGTT TAGTAAACTT GTTACTTGGG GTTACTTTTT TTATTTGTG  ATAAATTTTG    1440
TTATTCCTTG TGACAAACTT TCTTACATGT TTCCATTTTT AAATATGCCT GTATTTCTA    1500
AATAAAAATT ATATTAAATA GATGCTGCTC TACCCTCACC AAATGTACAT ATTCTGCTGT    1560
CTATTGGGAA AGTTCCTGGT ACACATTTTT ATTCAGTTAC TTAAAATGAT TTTTTCCATT    1620
AAAGTATATT TTGCTACT                                                 1638
```

( 2 ) INFORMATION FOR SEQ ID NO:2:

( i ) SEQUENCE CHARACTERISTICS:

(A) LENGTH: 794 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:2:

```
GAATTCTGCG GCCGCGAACT GCTGGCTGCC CACGGTACTC TGGAGCTGCA AGCCGAGATC     60
CTGCCCCGCC GGCCTCCCAC GCCGGAGGCC CAGAGCGAAG AGGAGAGATC CGATGAGGAG    120
CCGGAGGCCA AGAAGAGGA AGAGGAAAAA CCACACATGC CCACGGAATT TGATTTTGAT     180
GATGAGCCAG TGACACCAAA GGACTCCCTG ATTGACCGGA GACGCACCCC CAGGAAGCTC    240
AGCCCGGAGC CAGAAACGGG AGGCCCGCCT GGACAAGGTG CTGTCGGACA TGAAGAGACA    300
CAAGAAGCTG GAGGAGCAGA TCCTTCGTAC CGGGAGGGAC CTCTTCAGCC TGGACTCGGA    360
GGACCCCAGC CCCGCCAGCC CCCACTCCG ATCCTCCGGG AGTAGTCTCT TCCCTCGGCA     420
GCGGAAATAC TGATTCCCAC TGCTCCTGCC TCTAGGGTGC AGTGTCCGTA CCTGCTGGAG    480
CCTGGGCCCT CCTTCCCCCA GCCCAGACAT TGAGAAACTT GGGAAGAAGA GAGAAACCTC    540
AAGCTCCCAA ACAGCACGTT GCGGGAAAGA GGAAGAGAGA GTGTGAGTGT GTGTGTGTGT    600
TTTTTCTATT GAACAACTGT AGAGTGTGTG TGTGTGTTTT CTTTGGACA CCTATAGAGA     660
GAGTGTGTGT GTTTCTATT GAACATCTAT ATAGAGAG TGTGTGAGTG TGTGTTTCT        720
ATTGGACACC TATTCAAGAG ACCTGGACTG GATTTCTGA GTCTGAAATA AAAGATGCAG     780
AGCTATCATC TCTT                                                      794
```

(2) INFORMATION FOR SEQ ID NO:3:

(i) SEQUENCE CHARACTERISTICS:
(A) LENGTH: 794 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

```
GAATTCTGCG GCCGCGTGGG GACTGAGGAG GATGGCGGAG GCGTCGGCCA CAGGACGGTG     60
TACTTGTTTG ATCGGCGCGA AAAGGAGTCC GAGCTCGGGG ACCGGCCTCT GCAGGTCGGG   120
GAGCGCTCGG ACTACGCGGG ATTTCGCGCG TGTGTGTGTC AGACACTTGG CATTTCACCT   180
GAAGAAAAAT TTGTTATTAC AACAACAAGT AGGAAAGAAA TTACCTGTGA TAATTTTGAT   240
GAAACTGTTA AAGATGGAGT CACCTTATAC CTGCTACAGT CGGTCAATCA GTTACTACTG   300
ACAGCTACGA AAGAACGAAT TGACTTCTTA CCTCACTATG ACACACTGGT TAAAAGTGGC   360
ATGTATGAAT ATTATGCCAG TGAAGGACAA AATCCTTTGC CATTTGCTCT TGCGGAATTA   420
ATTGACAATC ATTGCTCTGC TACTTCTCGT AACATTGGGG TTAGAAGAAT ACAGATCCAA   480
TTGCTTTGTT GATGAAACAC AAGGAAAACC TGCTGTTGCA GTGATAGATA ATGGAAGAGG   540
AATGACCTCT AAACAGCTTA ACAACTGGGC CGTGTATAGG TTGTCCAAAT TCACAAGGCA   600
AGGTGACTTT GAAAGTGATC ATTCAGGATG TTCGTCCAGT ACCAGTGCCA CGCAGTTTAA   660
ATAGTGATAT TTCCTATTTT GGTGTTGGGG GCAAGCAAAC TGTCTTCTTT GTTGGACAAT   720
CAGCCAGGAT GATAAGCCAA CCTGCAGATT CCCCAGATGT TCACGAGCTT GTGCTTTGCT   780
AAAGGAGATT TTGG                                                      794
```

(2) INFORMATION FOR SEQ ID NO:4:

5,691,147

37

-continued

38

( i ) SEQUENCE CHARACTERISTICS:
    ( A ) LENGTH: 305 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:4:

```
GAATTCTGCG GCCGCGAGAG AGAGAGAGAG AGAGAGAGAG AGAGAGAGAG AGAGAGAGAG        60
AGAGAGAGAG AGAGAGAGAG AGAGAGAGAG AGAGAGAGAG AGAGAGAGAG AGAGAGAGAG       120
AGAGAGAGAG AGAGAGAGAG AGAGAGCATT CGGCCCGATA TGTCTCGCTC CGTGGCCTTA       180
GATGTTCTCG CTCTACTCTC TCTCTCTTGC CTGGAGGCTA TCCAGGTTGC TCCCATAGAT       240
TCATGACCTC TCACCTTCTC CAAGAGATTT GGGTGCAACC AAATTGCCGG GATCCAATCT       300
TTTCC                                                                   305
```

( 2 ) INFORMATION FOR SEQ ID NO:5:

( i ) SEQUENCE CHARACTERISTICS:
        ( A ) LENGTH: 305 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
GAATTCTGCG GCCGCCTGCC CCACAACTTT CTCACGGTGG CGCCTGGACA CAGTAGTCAC        60
CACAGTCCAG GCCTGCAGGG CCAGGGTGTG ACCCTGCCCG GGAGCCACC  CCTCCCTGAG       120
AAGAAGCGGG TCTCGGAGGG GGATCGTTCT TTGGTTTCAG TCTCTCCCTC CTCCAGTGGT       180
TTCTCCAGCC CGCACAGCGG GAGCAACATC AGTATCCCCT TCCCATATGT CCTTCCCGAC       240
TTTTCCAAGG CTTCAGAAGG GGGCTCAACT CTGCAGATTG TCCAGGTGAT AAACTTGTGA       300
TCGGG                                                                   305
```

( 2 ) INFORMATION FOR SEQ ID NO:6:

( i ) SEQUENCE CHARACTERISTICS:
        ( A ) LENGTH: 252 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
GAATTCTGCG GCCGCCGCCG TCCTCCGGCT GACAGGGGGA GGAGCCCGCC GGGAGGGCCG        60
GGGTCTCGGG TTGGGGAGCC GGAACGGGAG AGCAGCGCAG TCGGGTGTAC CGTGGTCGTG       120
TCCCGGGTAG GGTTGTTTCG GATCAGCGAC CGTCGGATTC TCCCTCATTG AACAGCGCCG       180
GTCTTGGGGG GGGCTGGGGG STTTGGAGGC CGACAGATTT TTCGAAAATC TTGTTGAAGG       240
GGGTTCGCGC CG                                                           252
```

( 2 ) INFORMATION FOR SEQ ID NO:7:

( i ) SEQUENCE CHARACTERISTICS:
        ( A ) LENGTH: 3407 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

| | | | | | | |
|---|---|---|---|---|---|---|
| GGCGAGCACT | GGCTACGTGC | GACTGTGGGG | AGCGGCGCGG | TGCTGGGTGC | TGCGGCGGCC | 60 |
| GATGCTGGCC | GCCGCCGGGG | GGCGGGTTCC | CACTGCAGCA | GGAGCGTGGT | TGCTCCGAGG | 120 |
| CCAGCGGACC | TGCGACGCCT | CTCCTCCTTG | GGCACTGTGG | GGCCGAGGCC | CGGCAATTGG | 180 |
| GGCCAATGG | CGGGGGTTTT | GGGAAGCGAG | CAGCCGCGGC | GGAGGCGCAT | TCTCGGGGG | 240 |
| CGAGGACGCC | TCCGAGGGCG | GCGCGGAGGA | AGGAGCCGGC | GGCGCGGGGG | GCAGCGCGGG | 300 |
| CGCCGGGGAA | GGCCCGGTCA | TAACGGCGCT | CACGCCCATG | ACGATCCCCG | ATGTGTTTCC | 360 |
| GCACCTGCCG | CTCATCGCCA | TCACCCGCAA | CCCGGTGTTC | CCGCGCTTTA | TCAAGATTAT | 420 |
| CGAGGTTAAA | AATAAGAAGT | TGGTTGAGCT | GCTGAGAAGG | AAAGTTCGTC | TCGCCCAGCC | 480 |
| TTATGTCGGC | GTCTTTCTAA | AGAGAGATGA | CAGCAATGAG | TCGGATGTGG | TCGAGAGCCT | 540 |
| GGATGAAATC | TACCACACGG | GGACGTTTGC | CCAGATCCAT | GAGATGCAGG | ACCTTGGGA | 600 |
| CAAGCTGCGC | ATGATCGTCA | TGGGACACAG | AAGAGTCCAT | ATCAGCAGAC | AGCTGGAGGT | 660 |
| GGAGCCCGAG | GAGCCGGAGG | CGGAGAACAA | GCACAAGCCC | CGCAGGAAGT | CAAAGCGGGG | 720 |
| CAAGAAGGAG | GCGGAGGACG | AGCTGAGCGC | CAGGCACCCG | GCGGAGCTGG | CGATGGAGCC | 780 |
| CACCCCTGAG | CTCCCGGCTG | AGGTGCTCAT | GGTGGAGGTA | GAGAACGTTG | TCCACGAGGA | 840 |
| CTTCCAGGTC | ACGGAGGAGG | TGAAAGCCCT | GACTGCAGAG | ATCGTGAAGA | CCATCCGGGA | 900 |
| CATCATTGCC | TTGAACCCTC | TCTACAGGGA | GTCAGTGCTG | CAGATGATGC | AGGCTGGCCA | 960 |
| GCGGGTGGTG | GACAACCCCA | TCTACCTGAG | CGACATGGGC | GCCGCGCTCA | CCGGGGCCGA | 1020 |
| GTCCCATGAG | CTGCAGGACG | TCCTGGAAGA | GACCAATATT | CCTAAGCGGC | TGTACAAGGC | 1080 |
| CCTCTCCCTG | CTGAAGAAGG | AATTTGAACT | GAGCAAGCTG | CAGCAGCGCC | TGGGGCGGGA | 1140 |
| GGTGGAGGAG | AAGATCAAGC | AGACCCACCG | TAAGTACCTG | CTGCAGGAGC | AGCTAAAGAT | 1200 |
| CATCAAGAAG | GAGCTGGGCC | TGGAGAAGGA | CGACAAGGAT | GCCATCGAGG | AGAAGTTCCG | 1260 |
| GGAGCGCCTG | AAGGAGCTCG | TGGTCCCCAA | GCACGTCATG | GATGTTGTGG | ACGAGGAGCT | 1320 |
| GAGCAAGCTG | GGCCTGCTGG | ACAACCACTC | CTCGGAGTTC | AATGTCACCC | GCAACTACCT | 1380 |
| AGACTGGCTC | ACGTCCATCC | CTTGGGGCAA | GTACAGCAAC | GAGAACCTGG | ACCTGGCGCG | 1440 |
| GGCACAGGCA | GTGCTGGAGG | AAGACCACTA | CGGCATGGAG | GACGTCAAGA | AACGCATCCT | 1500 |
| GGAGTTCATT | GCCGTTAGCC | AGCTCCGCGG | CTCCACCCAG | GGCAAGATCC | TCTGCTTCTA | 1560 |
| TGGCCCCCCT | GGCGTGGGTA | AGACCAGCAT | TGCTCGCTCC | ATCGCCCGCG | CCCTGAACCG | 1620 |
| AGAGTACTTC | CGCTTCAGCG | TCGGGGGCAT | GACTGACGTG | GCTGAGATCA | AGGGCCACAG | 1680 |
| GCGGACCTAC | GTGGGCGCCA | TGCCCGGGAA | GATCATCCAG | TGTTTGAAGA | AGACCAAGAC | 1740 |
| GGAGAACCCC | CTGATCCTCA | TCGACGAGGT | GGACAAGATC | GGCCGAGGCT | ACCAGGGGGA | 1800 |
| CCCGTCGTCG | GCACTGCTGG | AGCTGCTGGA | CCCAGAGCAG | AATGCCAACT | TCCTGGACCA | 1860 |
| CTACCTGGAC | GTGCCCGTGG | ACTTGTCCAA | GGTGCTGTTC | ATCTGCACGG | CCAACGTCAC | 1920 |
| GGACACCATC | CCCGAGCCGC | TGCGAGACCG | TATGGAGATG | ATCAACGTGT | CAGGCTACGT | 1980 |
| GGCCCAGGAG | AAGCTGGCCA | TTGCGGAGCG | CTACCTGGTG | CCCCAGGCTC | GCGCCCTGTG | 2040 |
| TGGCTTGGAT | GAGAGCAAGG | CCAAGCTGTC | ATCGGACGTG | CTGACGCTGC | TCATCAAGCA | 2100 |
| GTACTGCCGC | GAGAGCGGTG | TCCGCAACCT | GCAGAAGCAA | GTGGAGAAGG | TGTTACGGAA | 2160 |
| ATCGGCCTAC | AAGATTGTCA | GCGGCGAGGC | CGAGTCCGTG | GAGGTGACGC | CCGAGAACCT | 2220 |
| GCAGGACTTC | GTGGGGAAGC | CCGTGTTCAC | CGTGGAGCGC | ATGTATGACG | TGACACCGCC | 2280 |

```
CGGCGTGGTC ATGGGGCTGG CCTGGACCGC AATGGGAGGC TCCACGCTGT TGTGGAGAC    2340
ATCCCTGAGA CGGCCACAGG ACAAGGATGC CAAGGGTGAC AAGGATGGCA GCCTGGAGGT   2400
GACAGGCCAG CTGGGGGAGG TGATGAAGGA GAGCGCCCGC ATAGCCTACA CCTTCGCCAG   2460
AGCCTTCCTC ATGCAGCACG CCCCCGCCAA TGACTACCTG GTGACCTCAC ACATCCACCT   2520
GCATGTGCCC GAGGGCGCCA CCCCCAAGGA CGGCCCAAGC GCAGGCTGCA CCATCGTCAC   2580
GGCCCTGCTG TCCCTGGCCA TGGGCAGGCC TGTCCGGCAG AATCTGGCCA TGACTGGCGA   2640
AGTCTCCCTC ACGGGCAAGA TCCTGCCTGT TGGTGGCATC AAGGAGAAGA CCATTGCGGC   2700
CAAGCGCGCA GGGGTGACGT GCATCATCCT GCCAGCCGAG AACAAGAAGG ACTTCTACGA   2760
CCTGGCAGCC TTCATCACCG AGGGCCTGGA GGTGCACTTC GTGGAACACT ACCGGAGAT    2820
CTTCGACATC GCCTTCCCGG ACGAGCAGGC AGAGGCGCTG GCCGTGGAAC GGTGACGGCC   2880
ACCCCGGGAC TGCAGGCGGC GGATGTCAGG CCCTGTCTGG GCCAGAACTG AGCGCTGTGG   2940
GGAGCGCGCC CGGACCTGGC AGTGGAGCCA CCGAGCGAGC AGCTCGGTCC AGTGACCCAG   3000
ATCCCAGGGA CCTCAGTCGG CTTAATCAGA GTGTGGCATA GAAGCTATTT AATGATTAAA   3060
GTCATTTGCA GTGGGAGTTA GCATCACTAA CCTGACAGTT GTTGCCAGGA ATTTGCTTTG   3120
TTTACTGCTA GTATATTAGA AATCCTAGAT CTCAGAATCA CAATAGTAAT AAACAACAGG   3180
GGTCATTTTT TCCTAACTTA CTCTGTGTTC AGGTGTGGAA TTTCTGTCTC CCAAGAGGAA   3240
ATGTGACTTC ACTTGGTGC CAATGGACAG AAAATTCTAC CTGTGCTACA TAGGAGAAGT   3300
TTGGAATGCA CTTAATAGCT GGTTTTTACA CCTTGATTTC GAGGTGGAAA GAAATTGATC   3360
ATGAATCTCT AATAAATTTA AATCTCTTAA ACCAAAAAAA AAAAAA                  3407
```

( 2 ) INFORMATION FOR SEQ ID NO:8:

( i ) SEQUENCE CHARACTERISTICS:
        ( A ) LENGTH: 450 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
GAATTCTGCG GCCGCACTGG AGAACCCTGC TGTGACTGGG TGGGAGATGA GGGAGCAGGC    60
CACTTCGTGA AGATGGTGCA CAACGGGATA GAGTATGGGG ACATGCAGCT GATCTGTGAG   120
GCATACCACC TGATGAAAGA CGTGCTGGGC ATGGCGCAGG ACGAGATGGC CCAGGCCTTT   180
GAGGATTGGA ATAAGACAGA GCTAGACTCA TTCCTGATTG AAATCACAGC CAATATTCTC   240
AAGTTCCAAG ATACCGATGG CAAACACCTG CTGCCAAAGA TCARGGACAG CGCGGGGCAG   300
AAGGGCACAG GGAAGTGGAC CGCCATCTTC GCCCTGGGAT TACGGGGTAC CCGTCACCCT   360
CATTGGGGAA GGTGTCTTTG STCGGTGCTT ATCATCTCTT GAAGGATGAG AGAATTTCAA   420
GCTTGCAAAA AAGTTGAGGG GTCCCCAGAA                                    450
```

( 2 ) INFORMATION FOR SEQ ID NO:9:

( i ) SEQUENCE CHARACTERISTICS:
        ( A ) LENGTH: 8201 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
CTAAAAATAC CATTAAGTAA TAGTATTAGC TTTTGTATTC TGAGATTCAA CAGCAGCAGT    60
CACTTCCCTC CACTCCTATG TGTATCCCAG GACCACCCTG GGCGGGGAGG GCTGAGGTCA   120
GGGAGGTCTG AAGCTGGTCC TGGGCTCCGG GGGTGACAGT GATGAGGAAC TGGGTGCACA   180
CATGAGTGGG GCAGCCGGGC CTGGCCAGAG AAGCAACACA CACGTGCACA GACATGTTTA   240
TCCACATACA CATGTGCACG CATGTGCACA AACACATTGC AGGCAGGCAT GTTGACGCCT   300
CAGGCAGCGG AGGACCCTGA CTCTGGGCCC TGCTGACCCG GGCAAGGCCC ATTGTGATGC   360
GTGCCATGAC CTCAGAATGT CACTGGTGCT TAGCACCTAT CCGCTCTCCA GACTGCGTCT   420
GTGTTCTACG GCAGTTACAC ACACGCAGTG GTATTCACAA GCGGTTTTGT GGACTCAAAG   480
GTTTTCTCCC TGAGAGGCAT AACCCAGGCC AGCTGATTCA TCAGAATCAG GTGAGTGTGA   540
CCTGCTCTCT TCCCTCCAGG CTGACTTGGG GACAGTGGCT ATGGTATGGG CGGTGTTGGC   600
CTCTGGGCAG CTACAGAGGA GGGTCATCCC TGAGCACTCA CCGGGCGCCC GTTCTACACT   660
GCCCATGTAG ACGATTTTCT CTTTCGTCTT CATGGTGGCT TCGTAGAGTG GGTGCTGTTC   720
CCAAATGTAC CCATTCGACA GGTGAGCCGT CTGGGGTCAG AGAGGCAGTA ACTGGCCTGG   780
GAATCCAGAC AAGACCCTGG GTTTTGCTCT CAGCCCTGCT GTGTGCCATG CTAGACTTCA   840
GGCCTCAACC CTGAGACCTC CCTGCTCTAG ATCCCAAATC TGCCCAGATT TCCGATCCAA   900
TGGGCAGAGC CTGGCCCTGG CAGAGACACT GGATGGATC CACTGTGGGT GGGGAGGAGG    960
GAAGGGTCCT CAGAACACAC CTGGGGCCTA AGCTGGGTCT TGATGGTCAC TGTGGGACCC  1020
ACTGGACACA CACAGTCCCT TGTCTGGGAG TGGCATGGGG AGCCTTCTGC CCTTGGGCAG  1080
TTGTGGAAAG TGAAGGAGCC CTGGAGAGCT GGCTGAGGGG AGACTATCTT CCCTTGTGTT  1140
CAAAGGGGTC CAGGCACTGG GGCTCTCCCC AAGTATTTCT TATTCTGTCT GGCCTCGCTT  1200
TCCTTTTGCC CTGAGTATTC TCAGGAGGGA CGGTCCATCT AGATGTCCTC CAGGAGCAAG  1260
GACCCACTGT TCTTCATCAG TGACCCAGGA AAATGAAGCC CCTCCTGTG GGGACAGCTC  1320
AGAATGGTGG AGTCCACAGT CCCTCCCTGA GAGACATGGT TTCCATGAGC ACAGTGGCTG  1380
CTTTGGAGAC AGTAATCATT TTCATCCCCA AAACCAAACA CACTCCTGCT CAAATGGTGT  1440
TATTGCTAAA GCAGCTTCAC TGGTTAGACT GAAGGGCCAT GGTAGCCCAA GTGATGAGCG  1500
GGGTAGAATG GAGCAGTCAG GAGAGATCTT GTTCCCCGTA GGAAACTGGG CATCTCTGTG  1560
GCCCTGAACA TCCCAGGAGG CCGATCGTAC AGAGACCTCT GGTGCCTGAC CGCAGTTCAC  1620
ATCCACATCC CTGGAATAGA CCATCACAGG CTCTTCACCC TTGGCAGGTG GACACCATTC  1680
AACCTGCCGG GGCAGGATGG ACATGGTAGA GAATGCAGAT AGTTTGCAGG CACAGGAGCG  1740
GAAGGACATA CTTATGAAGT ATGACAAGGG ACACCGAGCT GGGCTGCCAG AGGACAAGGG  1800
GCCTGAGCCC GTTGGAATCA ACAGCAGCAT TGATCGTTTT GGCATTTTGC ATGAGACGGA  1860
GCTGCCTCCT GTGACTGCAC GGGAGGCGAA GAAAATTCGG CGGGAGATGA CACGAACGAG  1920
CAAGTGGATG GAAATGCTGG GAGAATGGGA GACATATAAG CACAGTAGCA AACTCATAGA  1980
TCGAGTGTAC AAGGGAATTC CCATGAACAT CCGGGGCCCG GTGTGGTCAG TCCTCCTGAA  2040
CATTCAGGAA ATCAAGTTGA AAAACCCCGG AAGATACCAG ATCATGAAGG AGAGGGGCAA  2100
GAGGTCATCT GAACACATCC ACCACATCGA CCTGGACGTG AGGACGACTC TCCGGAACCA  2160
TGTCTTCTTT AGGGATCGAT ATGGAGCCAA GCAGAGGGAA CTATTCTACA TCCTCCTGGC  2220
CTATTCGGAG TATAACCCGG AGGTGGGCTA CTGCAGGGAC CTGAGCCACA TCACCGCCTT  2280
GTTCCTCCTT TATCTGCCTG AGGAGGACGC ATTCTGGGCA CTGGTGCAGC TGCTGGCCAG  2340
TGAGAGGCAC TCCCTGCCAG GATTCCACAG CCCAAATGGT GGGACAGTCC AGGGGCTCCA  2400
```

```
AGACCAACAG GAGCATGTGG TACCCAAGTC ACAACCCAAG ACCATGTGGC ATCAGGACAA    2460
GGAAGGTCTA TGCGGGCAGT GTGCCTCGTT AGGCTGCCTT CTCCGGAACC TGATTGACGG    2520
GATCTCTCTC GGGCTCACCC TGCGCCTGTG GGACGTGTAT TTGGTGGAAG GAGAACAGGT    2580
GTTGATGCCA ATAACCAGCA TTGCTCTTAA GGTTCAGCAG AAGCGCCTCA TGAAGACATC    2640
CAGGTGTGGC CTGTGGGCAC GTCTGCGGAA CCAATTCTTC GATACCTGGG CCATGAACGA    2700
TGACACCGTG CTCAAGCATC TTAGGGCCTC TACGAAGAAA CTAACAAGGA AGCAAGGGGA    2760
CCTGCCACCC CCAGGCCCAA CAGCCCTGGG ACGAAGGTGT GTGGCAGGAA GCCCCAGCC    2820
AGTCTGAACC CTGGGGGCAG TCCAGGAGC CACCCACCAT GCCCAACGG CTTCCCCATG    2880
CCAGGCAGCA CACACCCCTC CCTCTGGGAT CAGCAGACTA CAGGCGTGTC GTCAGTGTCA    2940
GACCACAGGG GCCACACAGA GACCCCAAGG ACTCCAGAGA TGCAGCCAAA CGCGAGCAAG    3000
GGTCCTTGGC ACCCAGGCCT GTGCCGGCTT CACGTGGTGG GAAGACCCTC TGCAAGGGGT    3060
ATAGGCAGGC CCCTCCAGGC CCACCAGCCC AGTTCAGCG GCCCATTTGC TCAGCTTCCC    3120
CGCCATGGGC ATCTCGTTTT TCCACGCCCT GTCCTGGTGG GGCTGTCCGG AAGACACGT    3180
ACCCTGTGGG CACTCAGGGT GTGCCCAGCC TGGCCCTGGC TCAGGGAGGA CCTCAGGGTT    3240
CCTGGAGATT CCTGGAGTGG AAGTCAATGC CCCGGCTCCC AACGGACCTG GATATAGGGG    3300
GCCCTTGGTT CCCCCATTAT GATTTGAAC GGAGCTGCTG GGTCCGTGCC ATATCCCAGG    3360
AGGACCAGCT GGCCACCTGC TGGCAGGCTG AACACTGCGG AGAGGTTCAC AACAAAGATA    3420
TGAGTTGGCC TGAGGAGATG TCTTTTACAG CAAATAGTAG TAAAATAGAT AGACAAAAGG    3480
TTCCCACAGA AAAGGGAGCC ACAGGTCTAA GCAACCTGGG AAACACATGC TTCATGAACT    3540
CAAGCATCCA GTGCGTTAGT AACACACAGC CACTGACACA GTATTTATC TCAGGGAGAC    3600
ATCTTTATGA ACTCAACAGG ACAAATCCCA TTGGTATGAA GGGGCATATG GCTAAATGCT    3660
ATGGTGATTT AGTGCAGGAA CTCTGGAGTG GAACTCAGAA GAGTGTTGCC CCATTAAAGC    3720
TTCGGCGGAC CATAGCAAAA TATGCTCCCA AGTTTGATGG GTTTCAGCAA CAAGACTCCC    3780
AAGAACTTCT GGCTTTTCTC TTGGATGGTC TTCATGAAGA TCTCAACCGA GTCCATGAAA    3840
AGCCATATGT GGAACTGAAG GACAGTGATG GCCGACCAGA CTGGGAAGTA GCTGCAGAGG    3900
CCTGGGACAA CCATCTAAGA AGAAATAGAT CAATTATTGT GGATTTGTTC CATGGGCAGC    3960
TAAGATCTCA AGTCAAATGC AAGACATGTG GGCATATAAG TGTCCGATTT GACCCTTTCA    4020
ATTTTTTGTC TTTGCCACTA CCAATGGACA GTTACATGGA CTTAGAAATA ACAGTGATTA    4080
AGTTAGATGG TACTACCCCT GTACGGTATG GACTAAGACT GAATATGGAT GAAAAGTACA    4140
CAGGTTTAAA AAAACAGCTG AGGGATCTCT GTGGACTTAA TTCAGAACAA ATCCTACTAG    4200
CAGAAGTACA TGATTCCAAC ATAAAGAACT TCCTCAGGA TAACCAAAAA GTACAACTCT    4260
CAGTGAGCGG ATTTTGTGT GCATTTGAAA TTCCTGTCCC TTCATCTCCA ATTTCAGCTT    4320
CTAGTCCAAC ACAAATAGAT TTCTCCTCTT CACCATCTAC AAATGGAATG TTCACCCTAA    4380
CTACCAATGG GGACCTACCC AAACCAATAT TCATCCCCAA TGGAATGCCA AACACTGTTG    4440
TGCCATGTGG AACTGAGAAG AACTTCACAA ATGGAATGGT TAATGGTCAC ATGCCATCTC    4500
TTCCTGACAG CCCCTTTACA GGTTACATCA TTGCAGTCCA CCGAAAAATG ATGAGGACAG    4560
AACTGTATTT CCTGTCACCT CAGGAGAATC GCCCAGCCT CTTTGGAATG CCATTGATTG    4620
TTCCATGCAC TGTGCATACC CAGAAGAAAG ACCTATATGA TGCGGTTTGG ATTCAAGTAT    4680
CCTGGTTAGC AAGACCACTC CCACCTCAGG AAGCTAGTAT TCATGCCCAG GATCGTGATA    4740
ACTGTATGGG CTATCAATAT CCATTCACTC TACGAGTTGT GCAGAAAGAT GGGATCTCCT    4800
```

-continued

```
GTGCTTGGTG CCCACAGTAT AGATTTTGCA GAGGCTGTAA AATTGATTGT GGGGAAGACA    4860
GAGCTTTCAT TGGAAATGCC TATATTGCTG TGGATTGGCA CCCCACAGCC CTTCACCTTC    4920
GCTATCAAAC ATCCCAGGAA AGGGTTGTAG ATAAGCATGA GAGTGTGGAG CAGAGTCGGC    4980
GAGCGCAAGC CGAGCCCATC AACCTGGACA GCTGTCTCCG TGCTTTCACC AGTGAGGAAG    5040
AGCTAGGGGA AAGTGAGATG TACTACTGTT CCAAGTGTAA GACCCACTGC TTAGCAACAA    5100
AGAAGCTGGA TCTCTGGAGG CTTCCACCCT TCCTGATTAT TCACCTTAAG CGATTTCAAT    5160
TTGTAAATGA TCAGTGGATA AAATCACAGA AAATTGTCAG ATTTCTTCGG GAAAGTTTTG    5220
ATCCGAGTGC TTTTTTGGTA CCACGAGACC CGGCCCTCTG CCAGCATAAA CCACTCACAC    5280
CCCAGGGGGA TGAGCTCTCC AAGCCCAGGA TTCTGGCAAG AGAGGTGAAG AAAGTGGATG    5340
CGCAGAGTTC GGCTGGAAAA GAGGACATGC TCCTAAGCAA AAGCCCATCT TCACTCAGCG    5400
CTAACATCAG CAGCAGCCCA AAAGGTTCTC CTTCTTCATC AAGAAAAAGT GGAACCAGCT    5460
GTCCCTCCAG CAAAAACAGC AGCCCTAATA GCAGCCCACG GACTTTGGGG AGGAGCAAAG    5520
GGAGGCTCCG GCTGCCCCAG ATTGGCAGCA AAATAAGCC GTCAAGTAGT AAGAAGAACT    5580
TGGATGCCAG CAAAGAGAAT GGGGCTGGGC AGATCTGTGA GCTGGCTGAC GCCTTGAGCC    5640
GAGGGCATAT GCGGGGGGGC AGCCAACCAG AGCTGGTCAC TCCTCAGGAC CATGAGGTAG    5700
CTTTGGCCAA TGGATTCCTT TATGAGCATG AAGCATGTGG CAATGGCTGT GGCGATGGCT    5760
ACAGCAATGG TCAGCTTGGA AACCACAGTG AAGAAGACAG CACTGATGAC CAAAGAGAAG    5820
ACACTCATAT TAAGCCTATT TATAATCTAT ATGCAATTTC ATGCCATTCA GGAATTCTGA    5880
GTGGGGGCCA TTACATCACT TATGCCAAAA ACCCAAACTG CAAGTGGTAC TGTTATAATG    5940
ACAGCAGCTG TGAGGAACTT CACCCTGATG AAATTGACAC CGACTCTGCC TACATTCTTT    6000
TCTATGAGCA GCAGGGGATA GACTACGCAC AATTTCTGCC AAAGATTGAT GGCAAAAAGA    6060
TGGCAGACAC AAGCAGTACG GATGAAGACT CTGAGTCTGA TTACGAAAAG TACTCTATGT    6120
TACAGTAAAG CTACCACTCT GGCTGCTAGA CAGCTTGGTG GCGAGGGAGA TGACTCCTTG    6180
TAGCTGATAC TTGGCAAAAG TGTCACTGAA AGACAAGCTA AATGTAGTTA TTTTATCCTG    6240
TTAGAACAAA AATTCTAATT AAAATAGTTA ACTTGAAGAG TAGAAACAAT GTATTTTGA    6300
AGTCTCATAC AAGCTGTCTG ATAGAGAACT TCAGGCAGA TCCCACCATT AGCCTGTAAA    6360
CAAAAGGTGT GGCACCAGCC ACCTGGGACC AAATAAGAAT TGAATTGTGC TTGTCCAGAT    6420
ATGAACAAAT ATGTAGTGAG TATAGAGTTT ACCAATAATC ATAACAAATA TTAAAGATTT    6480
CCTTGGAGTC AGAGGAAAAA ACAAACAATT ATAATGTTGT CTAGGGACGA CATGATACGC    6540
TACCTCCTTT TTCCTGAAGT TTTATTCCAT TATATTGACA AGATGGAGAA AGCAAGATCA    6600
TGAAGGTGTG CAAATGATTC TTACGGCATG GACAAGGATT TTTCAATTTA TTTTTTAAAC    6660
TGTTTCCATA CCCTTTCTTT TTCTTGCTTT TTGTTTTTGC CATTGTGTTT ACGTTGAGA    6720
CACAACCAGT CATTGGTGGC AGGGGCATAG AGTGGTCAGT CTGAAGGGA GGCTCTCTTA     6780
AGAGCTATGT GCCTTCCAAC CAGAGGGAGA CCCAGTAGAA AGAAAAACAT CCTGGGAAAT    6840
CCAGCTACCA GGGCCCTCCC AGTGGAGGCA TCTTACATTT AGGCTACTTC AAGTATCCTC    6900
AGAAATGTAT TCTGCACCCC CGGCCCCGCC CATGCTGAGG GAAGGGAGC AGTTGCCAAT     6960
ATTTGCACCA TCTTCACATG CACATGTTGC AACAAGAGCT TCTGGGAAGG TAAGCGGCAT    7020
CGGAGCTAGA TCACGTTTCA CAATTAGTGG TTATTCTTTT CTGTGTTTGT TTTGCACTTT    7080
AAAAAAGAGA GAACACATGC AAATGAACTT GCTTGTGTGT ATTTGATGGC TCTAAGGGCT    7140
ATAAATTACA AACAAAACAC ATCCCAGACA TTAGGAGTTC ATAAGTATAT TTAATGAAAT    7200
```

-continued

```
TGGTGGTTTT AGGAAGTCAA CTTTAGTTTT GCTTTGTTTG CATGTCCACT GGTTTTTTTA   7260
TTTTGATATT TGTCTTTTTT TAAATTTTAC AGTAGTCATT GAAAGTTATG TTTCTTTGCT   7320
TACTTCATTT TTTCCCTCTA ATTATTTAAG ATTGGAACAA AAGTATAAAT ATTATTTATT   7380
TGAGGTAGAA TTTTTTTCAT GTAGTTTCTT AATATATACT TGAAGGAAAT GTTTCACCTT   7440
ATTTTTGGTC TTTGTTTATT CATTTAGACC CTGCAAGTTG ATTCTCATTG CCAGATTCCA   7500
TTACCCTTTC TTCCTCATAG GTAGTAATTA CCAATGTAAC TAAGCATTTG TGTTCTGATA   7560
TCTGAGGCCA GTAACTATTA ATATCTAGTT CTCAGAGCAT TTGGAAAGGT TATCTTAAAT   7620
GGCTACCTAA ATTGAAATCC TTTTCAGAAA AAATATAATT GCAAGTAGGT AGGAGTGGCC   7680
TAAATTGTCT AATGTAATAA AGTCAGACAA AATGCACACT TTATAGTTTC AAGATTTTCA   7740
GTAAATAAAA TCTGTCCATT CCTACCTGGA CATGTCCCAT TAAAAGTGG AAGATTTTAA    7800
ATAATTTCTT TACAGATGTT TTATTTAAAC AGGTAGCACA ATCTACTAAT GTTGTGTGAT   7860
TTGTGTTATA CTGGTTGTAA TTAATTTTTT TAATTCATGA ACTAGCGGAA AATTTATTAA   7920
ATTAACTATT AACTACATTC ACCTTGTAAA TTACTGTATA AAACTTGTTG ACAATGCACT   7980
GACTTTAGAA AGATGTTAAT GTACATAAAT AGAGTGTAAA TAAAATAGTG TTGATGTACT   8040
GAAATATGAA CTGTATCAAA AGTATTGGTA ATTGTATATG GGGTGTACCT GTTTATCTGT   8100
TAACTATTAT CCAAACAAAT TAAATACTGT GGTTGCCTCT ATGTGCTGTT TTTCCTCATA   8160
CAAGTAAACA CAGAAAGTCA AAAAAAAAA AAAAAAAAA A                         8201
```

( 2 ) INFORMATION FOR SEQ ID NO:10:

( i ) SEQUENCE CHARACTERISTICS:
        ( A ) LENGTH: 945 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

```
GAATTCTGCG GCCGCCAGAA AATTCACAAA GAGATGCCCT GTAAGTGTAC TGTATGTGGC    60
AGTGACTTCT GCCATACTTC ATACCTACTT GAACATCAGA GGGTCCATCA TGAAGAGAAA   120
GCCTATGAGT ATGATGAATA TGGGTTGGCC TATATTAAAC AACAAGGAAT TCATTTCAGA   180
GAAAAGCCCT ATCGTGTAG TGAATGTGGA AAAGACTTCA GATTGAATTC ACATCTTATT    240
CAGCATCAAA GAATTCACAC AGGAGAGAAA GCACATGAAT GTCATGAATG TGGAAAAGCT   300
TTCAGTCAAA CCTCATGCCT TATTCAGCAT CACAAAATGC ATAGGAAAGA GACTCGTATT   360
GAATGTAATG AGTATTGAGG GCAGGTTCAA GTCATAGCTC AGATCTTATC CTGCAACAAG   420
GAAGTCCTCA CCAGACAGAA AGCCTTTGAT TGGTGATGTA TGGGAAAAGA ACTCCAGTCA   480
GAGAGCACAT CTAGTTCAAC ATCAGAGCAT TCATACCAAA GAGAACTCAT GAATGTAATG   540
AAGATGGGAA GATATTTATC AAATTCAGGC TTCATTCAGC ATCTGAGAGT TCACACCAGG   600
GAGCAAATCA TGTATGTACT GCATGTGGTA AAGCCTTCAG TCATAGCTCA GCCATTGCTC   660
AGCATCAGAT AATTCACACC AGAGAGAAAC CCTCTGAATG TGACGAATGA AGAAAGGTA    720
TTAGTGTTAA ACTCTTAATC GACTCCTGCA AATCTATACC AGTGAGAAAT CTTACAAATG   780
TATTGGATTG TGGCAAATTT CTCATGCTAT TAGTATTTTC ATACCTTAGT CACATGTGGG   840
GGAATCCACA TGGGAATAAA CTCCCATTGC TGCAATGATT GTGAAAAGCA TCAGGCAAGG   900
AACTTCCTGG TTAGGTTCAA TTCCACGCCA TGCAAAAGGT TTTA                    945
```

(2) INFORMATION FOR SEQ ID NO:11:

(i) SEQUENCE CHARACTERISTICS:
(A) LENGTH: 971 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:11:

| | | | | | |
|---|---|---|---|---|---|
| GAATTCTGCG | GCCGCCTCTT | CGCTGAGGCG | GGGCCAGACT | TGAACTGCG | GTTAGAGCTG | 60 |
| TATGGGGCCT | GTGTGGAAGA | AGAGGGGGCC | CTGACTGGCG | GCCCCAAGAG | GCTTGCCACC | 120 |
| AAACTCAGCA | GCTCCCTGGG | CCGCTCCTCA | GGGAGGCGTG | TCCGGGCATC | GCTGGACAGT | 180 |
| GCTGGGGGTT | CAGGGAGCAG | TCCCATCTTG | CTCCCCACCC | CAGTTGTTGG | TGGTCCTCGT | 240 |
| TACCACCTCT | TGGCTCACAC | CACACTCACC | CTGGGAGGAG | TGCAAGATGG | ATTCCGCACA | 300 |
| CATGACCTCA | CCCTTGGCAG | TCATGAGGAG | AACCTGCCTG | GCTGCCCCTT | TATGGTAGCG | 360 |
| TGTGTTGCCG | TCTGGCAGCT | CAGCCTCTCT | GCATGACTCA | GCCCACTGCA | AGTGGTACCC | 420 |
| TCAGGGTGCA | GCAAGCTGGG | GAGATGCAGA | ACTGGGCACA | AGTGCATGGA | GTTCTGAAAG | 480 |
| GCACAAACCT | CTTCTGTTAC | CGGCAACCTG | AGGATGCAGA | CACTGGGGAA | GAGCCGCTGC | 540 |
| TTACTATTGC | TGTCAACAAG | GAGACTCGAG | TCCGGGCAGG | GGAGCTGGAC | CAGGCTCTAG | 600 |
| GACGGCCCTT | CACCCTAAGC | ATCAGTAACC | AGTATGGGA | TGATGAGGTG | ACACACACCC | 660 |
| TTCAGACAGA | AAGTCGGGAA | GCACTGCAGA | GCTGGATGGA | GGCTCTTGTG | GCAGCTTTTT | 720 |
| CTTTTGGACA | ATGAGCCAAT | GGAAGCAGTG | CTTGTGATGA | AATCAATGAA | AATTGGAAAC | 780 |
| TTCCTGCTCC | CCCGGAAACC | ACCCCAAGCA | CTGGCAAAGC | AGGGGGTCCT | TGTACCATGA | 840 |
| GATGGCTATT | GAGCCGCTGG | ATGACATCGC | AGCGGGTGAA | AGACATCCTG | ACCCAGGGGG | 900 |
| AGGGCGCAAG | GTTGGAGACA | CCCCCCCCGG | TTGGAATTTT | TACAGACAGC | CTGCCTGCTT | 960 |
| ACCCCTGTCG | C | | | | | 971 |

(2) INFORMATION FOR SEQ ID NO:12:

(i) SEQUENCE CHARACTERISTICS:
(A) LENGTH: 1075 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:12:

| | | | | | |
|---|---|---|---|---|---|
| GAATTCTGCG | GGCGCCAACA | ACGTGATGAA | TATCTGGAAA | GTTTCTGCAA | GTTCGGCCCT | 60 |
| GTCAACAACA | GCACCATGAA | AATCGACCAC | TTTCAGCTAG | ATAATGAGAA | GCCCATGCGA | 120 |
| GTGGTGGATG | ATGAAGACTG | GGTAGACCAG | CGTCTCATCA | GCGAGCTGAG | GAAGGAGTAC | 180 |
| GGATTGACCT | ACACTGATTC | TTCATGGTGC | TAACAGATGT | GGATCTGAGA | GTCAAGCAAT | 240 |
| ACTATGAGGT | ACCAATAACA | ATGAAGTCTG | TGTTTGCATC | TGATCGATAC | TTTCCAGTCC | 300 |
| CGAATCAAAG | ATATGGAGAA | GCAGAAGAAG | GAGGGCATTG | TTTGCAAAGA | GGACAAAAAG | 360 |
| CAGTCCCTGG | AGAACTTCCT | ATCCAGGTTC | CGGTGGAGGA | GGAGGTTGCT | GGTGATCTCT | 420 |
| GCTCCTAACG | ATGAAGACTG | GGCCTATTCA | CAGCAGCTCT | CTGCCCTCAG | TGGTCAGGCG | 480 |
| TGCAATTTGG | GTCTGCGCCA | CATAACCATT | CTGAAGCTTT | AGGCGTTGGA | GAGGAAGTTG | 540 |
| GGGAGTCTT | AGAACTGTTC | CCAATTAATG | GGAGCTCTGT | TGTTGAGCGA | GAAGACGTWC | 600 |
| CAGCCCATTT | GTGAAAGACA | TTCGTAACTA | TTTTCAAGTG | AGCCCGGAGT | ACTTCTCCAT | 660 |

-continued

| | | | | | | |
|---|---|---|---|---|---|---|
| GCTTCTAGTC | GGAAAAGACG | GAAATGTCAA | ATCCTGGTAT | CCTTCCCCAA | TGTGGTCCAT | 720 |
| GGTGATTGTG | TACGATTTAA | TTGATTCGAT | GCAACTTCGG | AGACAGGAAA | TGGCGATTCA | 780 |
| GCAGTCACTG | GGATGCGCT | GCCCAGAAGA | TGAGTATGCA | GGCTATGGTT | ACCATAGTTA | 840 |
| CCACCAAGGA | TACCAGGATG | GTTACCAGGA | TGACTACCGT | CATCATGAGA | GTTATCACCA | 900 |
| TGGATACCCT | TACTGAGCAG | AAATATGTAA | CCTTAGACTC | ACCATTTCCT | CTGCAGCTGC | 960 |
| TGGAACTACG | ATTGGCCAGC | TCCATTCTTC | CACACTGGGG | TACTACATTT | CCTGGCTTTT | 1020 |
| TCTTTCAAGG | GTTTTTCTTT | AGGACTTAAA | TAAATTAGCA | AACTTTTCAA | CCCTT | 1075 |

( 2 ) INFORMATION FOR SEQ ID NO:13:

( i ) SEQUENCE CHARACTERISTICS:
( A ) LENGTH: 1439 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:13:

| | | | | | | |
|---|---|---|---|---|---|---|
| GAATTCTGCG | GCCGCCATTA | CTCCTGCAAC | ATATCTGGCT | CTCTGAAGCG | GCACTACAAC | 60 |
| AGGAAGCACC | CTAATGAGGA | GTATGCCAAC | GTGGGCACCG | GGAGCTGGC | AGCGGAGGTG | 120 |
| CTCATCCAGC | AAGGTGGTTT | GAAGTGTCCT | GTTGCAGCT | TTGTATATGG | CACCAAATGG | 180 |
| GAGTTCAATA | GGCACTTGAA | GAACAAACAT | GGCTTGAAGG | TGGTGGAAAT | TGATGGAGAC | 240 |
| CCCAAGTGGG | AGACAGCAAC | AGAAGCTCCT | GAGGAGCCCT | CCACCCAGTA | TCTCCACATC | 300 |
| ACAGAGTCCG | AAGAAGACGT | TCCAAGGGAC | ACAGGCAGCG | GTGGCCGCGC | TCCAGGACCT | 360 |
| GAGATACAAC | TCTGAGAGTG | GCGACCGACT | TGACCCCACG | GCTGTGAACA | TCCTGCAGCA | 420 |
| GATCAATGAG | CTGGGCGCCG | AGACCCATGA | CGCCACTGCC | CTTGCCTCGG | TGGTTGCCAT | 480 |
| GGCACCAGGG | ACGGTGACTG | TGGTTAAGCA | GGTCACCGAG | GAGGAGCCCA | GCTCCAACCA | 540 |
| CACGGTCATG | ATCCAGGAGA | CGGTCCAGCA | AGCGTCCGTG | GAGCTTGCCG | AGCAGCACCA | 600 |
| CCTGGTGGTG | TCCTCCGACG | ACGTGGAGGG | CATTGAGACG | GTGACTGTCT | ACACGCAGGG | 660 |
| CGGGGAGGCC | TCGGAGTTCA | TCGTCTACGT | GCAGGAGGCC | ATGCAGCCTG | TGGAGGAGCA | 720 |
| GGCTGTGGAG | CAGCCGGCCC | AGGAACTCTA | GAGGACATGT | GGCATCGGAT | GCCACAGGGC | 780 |
| GGGCTGCCAG | GCTCTGCAGG | CACCCAGGGT | GGGGAGCCAC | CCTTCCTGCC | CTACCCGCAG | 840 |
| AATGGTGCTC | TCCTTTGCCC | TCCCTGCCCA | GCAGCCTGAT | AGGACTCTCC | TAGTCCAACT | 900 |
| TGGGGTGGGC | AAGGCAGTCA | GCATCACCAG | CAACACCACA | GGACCCTCAC | CCCAGCATAG | 960 |
| ACACACACCC | CCTGACCCTT | ACCATCTGCT | TCCTGAAAGA | CTTCAGTGTC | AGCTCCCCTA | 1020 |
| CACACACCCA | CACCTTCACC | CCTTGCTCCA | AGATCCAACA | AGAGACTCCA | AGTCTTCCTC | 1080 |
| AGCATCTTCC | TTGGATCACA | ACTCCAGCTC | CTTGACTCTC | ATCTAGGTGC | CAAATGTTCA | 1140 |
| TCTGCAACCC | GCTATGCAGT | CTGGTGAGAG | GGAGACAGCC | ATCACATAGR | AAGTGGCCGT | 1200 |
| ACGGGTTTTA | ATCACTGCTG | GGTGGGGTGG | GGGTAGGGGG | ATTGTCCTGG | CTTTGTCGAC | 1260 |
| MAAGTCCCAC | TTCCCCGAGT | ATTAAGGGCC | CTTGGTATCA | AGTGAGGTAA | ATTCACCCAT | 1320 |
| CACAGGGTCT | CGCCCTACCA | TCCTGGAATT | ATTTCACTTT | TAAGATAAAT | GCACTATTTC | 1380 |
| ACTGTTCGCC | TCCCATTCTA | AGGAGGTGAG | GTGGTTGGAA | TAAAAACAGT | TCCTGTCCC | 1439 |

( 2 ) INFORMATION FOR SEQ ID NO:14:

( i ) SEQUENCE CHARACTERISTICS:

(A) LENGTH: 349 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:14:

| | | | | | | |
|---|---|---|---|---|---|---|
| GAATTCTGCG | GNCGCGAGAG | AGAGAGAGAG | AGAGAGAGAG | AGAGAGAGAG | AGAGAGAGAG | 60 |
| AGAGAGAGAG | AGAGAGAGAG | AGAGAGAGAG | AGAGAGAGAG | AGAGAGAGAG | AGAGAGAGAG | 120 |
| AGAGAGAGAG | AGAGAGAGAG | AGAGAGAGAG | AGAGAGAGAG | AGAGAGAGAG | AGAGAGCCCA | 180 |
| GGTCTTAACA | CATATGGGAC | TGATGTCATC | TCGACCTCTC | CATTTATTGA | GTCTGTGATT | 240 |
| TATTTGGAGT | GGAGGCATCG | TTTTTAAGAA | ACACATGTCA | TCTAGGTTGT | CTAAACCTAT | 300 |
| CTGCATCTAC | TCTCACCTCA | NCCCCCCCC | CCCCTTCCCC | CCCTNTTCC | | 349 |

(2) INFORMATION FOR SEQ ID NO:15:

(i) SEQUENCE CHARACTERISTICS:
(A) LENGTH: 572 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:15:

| | | | | | | |
|---|---|---|---|---|---|---|
| GAATTCTGCG | GCCGCCGATC | CGAGGTCCTT | TTAGTCTCAG | AGGATGGGAA | GATCCTGGCA | 60 |
| GAAGCAGATG | GACTGAGCAC | AAACCACTGG | CTGATCGGGA | CAGACAAGTG | TGTGGAGAGG | 120 |
| ATCAATGAGA | TGGTGAACAG | GGCCAAACGG | AAAGCAGGGG | TGGATCCTCT | GGTACCGCTG | 180 |
| CGAAGCTTGG | GCCTATCTCT | GAGCGGTGGG | GACCAGGAGG | ACGCGGGGAG | GATCCTGATC | 240 |
| GAGGAGCTGA | GGGACCGATT | TCCCTACCTG | AGTGAAAGCT | ACTTAATCAC | ACCGACGGCG | 300 |
| GCGGCTCCAT | CGACACAGCT | ACACCGGATG | GTGGAGTTGT | GCTCATATCT | GGAACAGGCT | 360 |
| CCAACTGCAG | GCTCATCAAC | CCTGATGGCT | CCGAGAGTGG | CTGCGGGCGG | CTTGGGGGCA | 420 |
| TATTATGGGT | GATGAGGGTT | CAGCCTACTG | GATCGCACAC | CAAGCAGTGA | AAATAGTGTT | 480 |
| TGGACTCCAT | TGAAAACTAG | AGGCGGTCCC | ATGATATCGG | TTACGTCAAA | CAGGCCATGT | 540 |
| TCCACTATTT | CCAGGTTCAG | ATCCGCTAGG | TT | | | 572 |

(2) INFORMATION FOR SEQ ID NO:16:

(i) SEQUENCE CHARACTERISTICS:
(A) LENGTH: 402 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:16:

| | | | | | | |
|---|---|---|---|---|---|---|
| GAATTCTGCG | GCCGCCAGAG | CAGCACGGAG | ATCAGCAAGA | CGCGGGGCGG | GGAGACAAAG | 60 |
| CGCGAGGTGC | GGGTGGAGGA | GTCCACCCAG | GTCGGCGGGG | CACCCCTTCC | CTGCTGTGTT | 120 |
| TGGGACTTC | CTGGGCCGGG | AGCGCCTGGC | ATCCTTCGGC | AGTATCACCC | GCAGCAGGA | 180 |
| GGGTGAGGCC | AGCTCTCAGG | ACATGACTGC | ACAGGTGACC | AGCCCATCGG | GCAAGGTGGA | 240 |
| AGCCGCAGAG | ATCGTCGAGG | GCGAGGACAG | CGTCTACAGC | GTGCGCTTTG | TGCCCCAGGA | 300 |
| AATGGGGGCC | CATACGGTCG | GTGTCAAGTA | CCGTGGNCAG | CACGTGCCCG | GNAGNCCCTT | 360 |
| TCAGTTCACT | GTNGGGCCGC | TGGGTGANGG | TTGGTGCCCA | CA | | 402 |

(2) INFORMATION FOR SEQ ID NO:17:

(i) SEQUENCE CHARACTERISTICS:
    (A) LENGTH: 771 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:17:

| | | | | | | |
|---|---|---|---|---|---|---|
| AAGGGGAAGA | GAAGAGAGTG | TCCAGGGAGC | CAGCAGGTGT | CCTCTCCCAG | AGTGGTATGC | 60 |
| AGCTGGAATA | TCTGTCCCTC | CCCTTCCAAC | TTCCCGCACG | CAGATCCTTG | CAGGTTGAGC | 120 |
| TCTGTGGAGG | CCAACCTGTC | CTCTCCAGGG | TGAAAGTGCA | GTGGAGGCCT | TCTGGCTCCA | 180 |
| CTCCAAATGT | GATAGAAGGG | GATCTCCTGG | TATTTGGCCA | GCAGCTTGCT | CCTCCAATGG | 240 |
| GCATGGGGGA | GGTCATGGAG | GAAGAGCGCA | GGTTGTGTTA | ACTGTCCTTG | AACATTAGCG | 300 |
| GTTTCGGCTC | CTCCACCAAG | TATCCGCCCA | GAGTCCGCTC | CAGCTCCAGC | ACCTCCTTCA | 360 |
| GTGCTACAGG | CCTGTCCTCC | AGACAGTAGA | CCCGGAGTCT | GTACTCCAGG | GAGGTGCAGA | 420 |
| GGGCGGGGGC | GAAGACGGCC | AGCTGGASCC | GCTTGACTGC | TGAGCGGGAA | TAGGACTCGC | 480 |
| CCGTGAACAC | GTAGGTGCCC | AGCTGGTCCA | GCAGGATGTG | ACAGGCCCTG | GCTCCAGCT | 540 |
| GGCAGTAGCA | GGGTGTGTTC | AGGGTCTCCT | CATCCAGGGT | CACCACCTCC | TCCCAGTGGC | 600 |
| CCTGGTGGGC | CTGGGTCTTG | AGCTGAAAGA | TCCAGTCACG | GGCACTGACT | TCGGCACAGT | 660 |
| GGGGCATGGT | GAGGATGACG | GGGCGGCACA | GCAGGAGGCC | TGTGGGTCCA | CAGGTCACCG | 720 |
| AGGGGCTCAA | TACTGTCTCG | GGAGAGGCAT | AATCTGGCAC | ATCATAAGGG | T | 771 |

(2) INFORMATION FOR SEQ ID NO:18:

(i) SEQUENCE CHARACTERISTICS:
    (A) LENGTH: 638 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:18:

| | | | | | | |
|---|---|---|---|---|---|---|
| GAATTCTGCG | GNCGCGCCCT | ACATGTGAAC | AACGATCGGG | CAAAAGTGAT | CCTGAAGCCA | 60 |
| GACAAGACTA | CTATTACAGA | ACCACACCAC | ATCTGGCCCA | CTCTGACTGA | CGAAGAATGG | 120 |
| ATCAAGGTCG | AGGTGCAGCT | CAAGGATCTG | ATCTTGGCTG | ACTACGGCAA | GAAAAACAAT | 180 |
| GTGAACGTGG | CATCACTGAC | ACAATCAGAA | ATTCGAGACA | TCATCCTGGG | TATTGAGGAT | 240 |
| CTTCGGGAAC | CGTCACAGGA | GGGGAGNAG | ATCGCTGAGA | TCCGAGAAGC | AGGCCCAGGG | 300 |
| AACAATCGCA | GGTTGACGGC | AACACAGGAT | TCGCACTTGT | CAACAAGCAT | TGGGGATGAG | 360 |
| TTCAACAACC | TCCACCACCC | CAGGAATTTT | TGAGACCCCG | GNTTTTCCTC | CATCCNAGNN | 420 |
| TTTANTTGGG | GGGGTCAAAG | GGCCNNTTNT | TTTTGCCCAC | CCTGAACCCT | AGGGCCCAAC | 480 |
| CCNNTTTTTT | TTTCNACNTT | TNGGAATNAA | AGGGGNTTTG | NTCANACCCC | ANCCCCCCN | 540 |
| GNTTTNNTTT | NGNNGGTCCC | CTTTNTTTTT | TTCCCCCCNG | NCCCNNTTTG | NNGGTTCCTT | 600 |
| TTTGGGGGGC | CCCCCNTTCN | CCCCGGGNNG | GGGCCCCC | | | 638 |

(2) INFORMATION FOR SEQ ID NO:19:

(i) SEQUENCE CHARACTERISTICS:
    (A) LENGTH: 1769 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:19:

| | | | | | | |
|---|---|---|---|---|---|---|
| GTGCTGCATT | TGATACAGTT | CTTGGGATAA | ATGTTGCAGT | CAAGAAACTA | AGCCGTCCTT | 60 |
| TTCAGAACCA | AACTCATGCC | AAGAGAGCTT | ATCGTGAACT | TGTCCTCTTA | AAATGTGTCA | 120 |
| ATCATAAAAA | TATAATTAGT | TTGTTAAATG | TGTTTACACC | ACCAAAAACT | CTAGAAGAAT | 180 |
| TTGCAAGATG | TGTATTTGGT | TATGGAATTA | ATGGATGCTA | ACTTATGTCA | GGTTATTCAC | 240 |
| ATGGAGCTGG | ATCATGAAAG | AATGTCCTAC | CTTCTTTACC | AGATGCTTTG | TGGTATTAAA | 300 |
| CATCTGCATT | CAGCTGGTAT | AATTCATAGA | GATTGAAGC | CTAGCAACAT | TGTTGTGAAA | 360 |
| TCAGACTGCA | CCCTGAAGAT | CCTTGACTTT | GGCCTGGCCC | GGACAGCGTG | CACTAACTTC | 420 |
| ATGATGACCC | CTTACGTGGT | GACACGGTAC | TACCGGGCGC | CCGAAGTCAT | CCTGGGTATG | 480 |
| GGCTACCAAA | GAGAACGTGG | ATATCTGGTC | AGTGGGTTGC | ATCATGGGAG | AGCTGGTGAA | 540 |
| AGGTTGTGTG | ATATTCCAAG | GCACTGACCA | TATTGATCAG | TGGAATAAAG | TTATTGAGCA | 600 |
| GCTGGGAACA | CCATCAGCAG | AGTTCATGAA | GAAACTTCAG | CCAACTGTGA | GGAATTATGT | 660 |
| CGAAAACAGA | CCAAAGTATC | CTGGAATCAA | ATTGGAAGAA | CTCTTTCCAG | ATTGGTTATT | 720 |
| CCCATCAGAA | TCTGAGCGAG | ACAAAATAAA | AACAAGTCAA | GCCAGAGATC | TGTTATCAAA | 780 |
| AATGTTAGTG | ATTGATCCTG | ACAAGCGGAT | CTCTGTAGAC | GAAGCTCTGC | GTCACCCATA | 840 |
| CATCACTGTT | TGGTATGACC | CCGCCGAAGC | AGAAGCCCCA | CCACCTCCAA | TTTTATGATG | 900 |
| CCCAGTTGGA | AGAAAGAGAA | CATGCAATTG | AGGAATGGAA | AGAGCTAATT | TACAAAGAAG | 960 |
| TCATGGATTG | GGAAGAAAGA | AGCAAGAATG | GTGTTGTAAA | AGATCAGCCT | TCAGCACAGA | 1020 |
| TGCAGCAGTA | AGTAGCAACG | CCACTCCTTC | TCAGTCTTCA | TCGATCAATG | ACATTTCATC | 1080 |
| CATGTCCACT | GAGCAGACGC | TGGCCTCAGA | CACAGACAGC | AGTCTTGATG | CCTCGACGGG | 1140 |
| ACCCCTTGAA | GGCTGTCGAT | GATAGGTTAG | AAATAGCAAA | CCTGTCAGCA | TTGAAGGAAC | 1200 |
| TCTCACCTCC | GTGGGCCTGA | AATGCTTGGG | AGTTGATGGA | ACCAAATAGA | AAAACTCCAT | 1260 |
| GTTCTGCATG | TAAGAAACAC | AATGCCTTGC | CCTATTCAGA | CCTGATAGGA | TTGCCTGCTT | 1320 |
| AGATGATAAA | ATGAGGCAGA | ATATGTCTGA | AGGAAAAAAT | TCCAACCACA | CTTCTAGAGA | 1380 |
| TTTTGTCCAA | GATCATTTCA | GGTGAGCAGT | TAGAGTAGGT | GAATTTGTTT | CCAAATTGTA | 1440 |
| CTAGTGACAG | TTTCTCATCA | TCTGTAACTG | TTGAGATGTA | TGTGCATGTG | ACCACCAATG | 1500 |
| CTTGGTTGGA | CTTGCCCATC | TAGCACTTTG | GGAATCAGTA | TTTAAATGCC | CAATAATCTT | 1560 |
| CCAGGTAGTG | CTGCTTCTGR | AGTTATCTCT | TAATCCTCTT | AAGTAATTTG | GTGTCTGTCC | 1620 |
| AGGAAAAGTC | GATTTATGTG | TATTAATTGG | CCATCATGAT | GTTATCATAT | CTTATTCCCC | 1680 |
| TTTATGCTAT | GATTTATTCT | ATCTTTTGTA | TTTCAGGAGA | CATATAATTA | AATCTATTTA | 1740 |
| ATAAATAAAA | ATATATAGCT | TTTCCTAGG | | | | 1769 |

( 2 ) INFORMATION FOR SEQ ID NO:20:

( i ) SEQUENCE CHARACTERISTICS:
( A ) LENGTH: 503 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:20:

```
GAATTCTGCG GTCGCCACGA AGAGAACATG CATGATCTTC AGTACCATAC CCACTACGCC        60

CAGAACCGCA CTGTGGAGAG GTTTGAGTCT CTGGTAGGAC GCATGGCTTC TCACGAGATT       120

GAAATTGGCA CCATCTTCAC CAACATCAAT GCCACCGACA ACCACGCGCA CAGCATGCTC       180

ATGTACCTGG ATGACGTGCG GCTCTCCTGC ACGCTGGGCT TCCACACCCA TGCCGAGGAG       240

CTCTACTACC TGAACAAGTC TGTCTCCATC ATGCTGGGCA CCACAGACCT GCTCCGGGAG       300

CGCTTCAGCC TGCTCAGTGC CCGGCTGGAC CTCAACGTCC GGAACCTCTC CATGATCGTG       360

GAGGAGATGA AGGAGGGGA CACACAGAAT GGGGAGATCC TTCGGAATGT AACATCCTAC        420

GAGGTGCCCC CGGCCTCCAG GACCAAGAGG TTCAAAAGAG ATTTGGCGTG AAACGGCTGT       480

GGCGGAGAGG CCAAAGGAGA CCG                                              503
```

( 2 ) INFORMATION FOR SEQ ID NO:21:

( i ) SEQUENCE CHARACTERISTICS:
        ( A ) LENGTH: 114 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

```
TCCAGAGGAT TTGAGGGACA GGGTCGGAGG GGGCTCTTCC GCCAGCACCG GAGGAAGAAA        60

GAGGAGGGGC TGGCTGGTCA CCAGAGGGTG GGGCGGACCG CGTGCGCTCG GCGG            114
```

( 2 ) INFORMATION FOR SEQ ID NO:22:

( i ) SEQUENCE CHARACTERISTICS:
        ( A ) LENGTH: 447 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

```
GAATTCTGCG GCCGCCGCCG CCACCCGAGC CGGAGCGGGC TGGGTCGTCA AGGTAAGATG        60

GTGGACTACA GCGTGTGGGA CCACATTGAG GTGTCTGATG ATGAAGACGA GACGCACCCC       120

AACATCGACA CGGCCAGTCT CTTCCGCTGG CGGCATCAGG CCCGGGTGGA ACGCATGGAG       180

CAGTTCCAGA AGGAGAAGGA GGAACTGGAC AGCGGCTGCC GCGAGTGCAA GCGCAAGGTG       240

GCCGAGTGCC AGAGGAAACT GAAGGAGCTG GAGGTGGCCG AGGGCGGCAA GGCAGAGCTG       300

GAGCGTCTGC AGGCCGAGGC ACAGCAGCTG CGCAATGAGG AGCGGAGCTG GAGCAGATG        360

CTGGAGGAGC ATGCGCAAGA AGGAGAAGAG CATGCCCTGG CAACGTGGAC ACGCTCAGCA       420

AAGACGGCTT CAGCAAAGAG CATGGTA                                          447
```

( 2 ) INFORMATION FOR SEQ ID NO:23:

( i ) SEQUENCE CHARACTERISTICS:
        ( A ) LENGTH: 329 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

```
GAATTCTGCG GCCGCGAGAG AGAGAGAGAG AGAGAGAGAG AGAGAGAGAG AGAGAGAGAG        60
```

-continued

```
AGAGAGAGAG  AGAGAGAGAG  AGAGAGAGAG  AGAGAGAGAG  AGAGAGAGAG  AGAGAGAGAG      120

AGAGAGAGAG  AGAGAGAGAG  AGAGAGAGAG  AGTCTCTATG  ATCTTCCAT   TCAAAACTTC      180

CAAGTTTCTC  CTTATGTGGA  ACCGAAATCT  TTCTTTCTCC  CGCGAAACTT  TACTACTATC      240

AGATAATTGA  AGACAGATCT  CTGTGTGTTC  TCTTCAAGCC  CAAACCAATT  CTGTTCCTTC      300

ACTCTATATA  GTGGTAATAT  GAATGTTTA                                           329
```

( 2 ) INFORMATION FOR SEQ ID NO:24:

( i ) SEQUENCE CHARACTERISTICS:
        ( A ) LENGTH: 391 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

```
GAATTCGGCA  CGAGGTTTTT  TTTTTTTTT   TTTTTTTTT   TTTTTGAAT   GGGGTTATCC       60

AGGATGTGAC  TTTTGGAGAT  TGGTTTTTTC  CGTGGATTAT  CCTGCCCCTG  AGATCCACCC      120

AAGTTGTGGG  ATCTGAAACT  TGCCCACCCT  CCGGGATTTT  GAAGGACGCT  GAATCATGAG      180

CGACAGTAAT  TGTGAAAGCC  AGTTTTTGG   TGTGAAAGTG  GAAGACTCAA  CCTCCACTGT      240

CCTAAAACGT  TACCAGAAGT  TGAAACCAAT  TGGCTCTGGG  GCCCAAGGGA  TTGTCGGGGC      300

TGCATCGGGT  ACAGTTCTTG  GGGATAAATG  TTGGAGCCAA  GGAATTAAGC  CCGCCCCTTT      360

TCAGAACCCA  ACTCATGAAA  GGGAGTTCTC  C                                       391
```

( 2 ) INFORMATION FOR SEQ ID NO:25:

( i ) SEQUENCE CHARACTERISTICS:
        ( A ) LENGTH: 148 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:25:

```
Met  Asp  Thr  Asp  Thr  Asp  Thr  Phe  Thr  Cys  Gln  Lys  Asp  Gly  Arg  Trp
  1              5                  10                       15

Phe  Pro  Glu  Arg  Ile  Ser  Cys  Ser  Pro  Lys  Lys  Cys  Pro  Leu  Pro  Glu
           20                  25                       30

Asn  Ile  Thr  His  Ile  Leu  Val  His  Gly  Asp  Asp  Phe  Ser  Val  Asn  Arg
              35                   40                        45

Gln  Val  Ser  Val  Ser  Cys  Ala  Glu  Gly  Tyr  Thr  Phe  Glu  Gly  Val  Asn
      50                   55                        60

Ile  Ser  Val  Cys  Gln  Leu  Asp  Gly  Thr  Trp  Glu  Pro  Pro  Phe  Ser  Asp
 65                    70                   75                            80

Glu  Ser  Cys  Ser  Pro  Val  Ser  Cys  Gly  Lys  Leu  Ser  Lys  Val  Gln  Asn
                      85                   90                        95

Met  Asp  Leu  Trp  Leu  Ala  Val  Asn  Thr  Pro  Leu  Xaa  Ser  Thr  Ile  Ile
                100                 105                 110

Tyr  Gln  Cys  Glu  Pro  Gly  Tyr  Glu  Gly  Gly  Glu  Gln  Gly  Thr  Cys
           115                 120                 125

Leu  Pro  Gly  Glu  Gln  Thr  Val  Glu  Trp  Arg  Gly  Gly  Asn  Met  Gln  Arg
      130                 135                       140

Asp  Gln  Val  Xaa
145
```

( 2 ) INFORMATION FOR SEQ ID NO:26:

( i ) SEQUENCE CHARACTERISTICS:
    ( A ) LENGTH: 130 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:26:

```
Glu Leu Leu Ala Ala His Gly Thr Leu Glu Leu Gln Ala Glu Ile Leu
 1               5                  10                  15

Pro Arg Arg Pro Pro Thr Pro Glu Ala Gln Ser Glu Glu Glu Arg Ser
                20                  25                  30

Asp Glu Glu Pro Glu Ala Lys Glu Glu Glu Glu Glu Lys Pro His Met
             35                  40                  45

Pro Thr Glu Phe Asp Phe Asp Asp Glu Pro Val Thr Pro Lys Asp Ser
         50                  55                  60

Leu Ile Asp Arg Arg Arg Thr Pro Arg Lys Leu Ser Pro Glu Pro Glu
 65                  70                  75                  80

Thr Gly Gly Pro Pro Gly Gln Gly Ala Val Gly His Glu Glu Thr Gln
                85                  90                  95

Glu Ala Gly Gly Ala Asp Pro Ser Tyr Arg Glu Gly Pro Leu Gln Pro
            100                 105                 110

Gly Leu Gly Gly Pro Gln Pro Arg Gln Pro Pro Thr Pro Ile Leu Arg
            115                 120                 125

Glu Xaa
130
```

( 2 ) INFORMATION FOR SEQ ID NO:27:

( i ) SEQUENCE CHARACTERISTICS:
    ( A ) LENGTH: 159 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:27:

```
Val Gly Thr Glu Glu Asp Gly Gly Val Gly His Arg Thr Val Tyr
 1               5                  10                  15

Leu Phe Asp Arg Arg Glu Lys Glu Ser Glu Leu Gly Asp Arg Pro Leu
                20                  25                  30

Gln Val Gly Glu Arg Ser Asp Tyr Ala Gly Phe Arg Ala Cys Val Cys
             35                  40                  45

Gln Thr Leu Gly Ile Ser Pro Glu Glu Lys Phe Val Ile Thr Thr Thr
         50                  55                  60

Ser Arg Lys Glu Ile Thr Cys Asp Asn Phe Asp Thr Val Lys Asp
 65                  70                  75                  80

Gly Val Thr Leu Tyr Leu Leu Gln Ser Val Asn Gln Leu Leu Leu Thr
                85                  90                  95

Ala Thr Lys Glu Arg Ile Asp Phe Leu Pro His Tyr Asp Thr Leu Val
            100                 105                 110

Lys Ser Gly Met Tyr Glu Tyr Tyr Ala Ser Glu Gly Gln Asn Pro Leu
            115                 120                 125
```

```
        Pro  Phe  Ala  Leu  Ala  Glu  Leu  Ile  Asp  Asn  His  Cys  Ser  Ala  Thr  Ser
             130                 135                      140

Arg  Asn  Ile  Gly  Val  Arg  Arg  Ile  Gln  Ile  Gln  Leu  Leu  Cys  Xaa
        145                      150                      155
```

( 2 ) INFORMATION FOR SEQ ID NO:28:

( i ) SEQUENCE CHARACTERISTICS:
    ( A ) LENGTH: 76 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:28:

```
        Glu  Arg  Glu  Arg  Glu  Arg  Glu  Arg  Glu  Arg  Glu  Arg  Glu  Arg  Glu  Arg
        1                   5                        10                       15

Glu  Arg  Glu  Arg  Glu  Arg  Glu  Arg  Glu  Arg  Glu  Arg  Glu  Arg  Glu  Arg
                            20                       25                       30

Glu  Arg  Glu  Arg  Glu  Arg  Glu  Arg  Glu  Arg  Glu  Ser  Ile  Arg  Pro  Asp
                            35                       40                  45

Met  Ser  Arg  Ser  Val  Ala  Leu  Asp  Val  Leu  Ala  Leu  Leu  Ser  Leu  Ser
             50                      55                       60

Cys  Leu  Glu  Ala  Ile  Gln  Val  Ala  Pro  Ile  Asp  Ser
        65                      70                       75
```

( 2 ) INFORMATION FOR SEQ ID NO:29:

( i ) SEQUENCE CHARACTERISTICS:
    ( A ) LENGTH: 94 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:29:

```
        Leu  Pro  His  Asn  Phe  Leu  Thr  Val  Ala  Pro  Gly  His  Ser  Ser  His  His
        1                   5                        10                       15

Ser  Pro  Gly  Leu  Gln  Gly  Gln  Gly  Val  Thr  Leu  Pro  Gly  Glu  Pro  Pro
                            20                       25                       30

Leu  Pro  Glu  Lys  Lys  Arg  Val  Ser  Glu  Gly  Asp  Arg  Ser  Leu  Val  Ser
                            35                       40                  45

Val  Ser  Pro  Ser  Ser  Ser  Gly  Phe  Ser  Ser  Pro  His  Ser  Gly  Ser  Asn
             50                      55                       60

Ile  Ser  Ile  Pro  Phe  Pro  Tyr  Val  Leu  Pro  Asp  Phe  Ser  Lys  Ala  Ser
        65                      70                       75                       80

Glu  Gly  Gly  Ser  Thr  Leu  Gln  Ile  Val  Gln  Val  Ile  Asn  Leu
                            85                       90
```

( 2 ) INFORMATION FOR SEQ ID NO:30:

( i ) SEQUENCE CHARACTERISTICS:
    ( A ) LENGTH: 51 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:30:

```
Arg Arg Pro Pro Ala Asp Arg Gly Arg Ser Pro Pro Gly Gly Pro Gly
 1               5                   10                  15
Ser Arg Val Gly Glu Pro Glu Arg Glu Ser Ser Ala Val Gly Cys Thr
            20                  25                  30
Val Val Val Ser Arg Val Gly Leu Phe Arg Ile Ser Asp Arg Arg Ile
        35                  40                  45
Leu Pro His
    50
```

( 2 ) INFORMATION FOR SEQ ID NO:31:

( i ) SEQUENCE CHARACTERISTICS:
        ( A ) LENGTH: 937 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:31:

```
Met Leu Ala Ala Gly Gly Arg Val Pro Thr Ala Ala Gly Ala Trp
 1               5                   10                  15
Leu Leu Arg Gly Gln Arg Thr Cys Asp Ala Ser Pro Pro Trp Ala Leu
            20                  25                  30
Trp Gly Arg Gly Pro Ala Ile Gly Gly Gln Trp Arg Gly Phe Trp Glu
        35                  40                  45
Ala Ser Ser Arg Gly Gly Gly Ala Phe Ser Gly Gly Glu Asp Ala Ser
    50                  55                  60
Glu Gly Gly Ala Glu Glu Gly Ala Gly Gly Ala Gly Gly Ser Ala Gly
65                  70                  75                  80
Ala Gly Glu Gly Pro Val Ile Thr Ala Leu Thr Pro Met Thr Ile Pro
                85                  90                  95
Asp Val Phe Pro His Leu Pro Leu Ile Ala Ile Thr Arg Asn Pro Val
            100                 105                 110
Phe Pro Arg Phe Ile Lys Ile Ile Glu Val Lys Asn Lys Lys Leu Val
            115                 120                 125
Glu Leu Leu Arg Arg Lys Val Arg Leu Ala Gln Pro Tyr Val Gly Val
    130                 135                 140
Phe Leu Lys Arg Asp Asp Ser Asn Glu Ser Asp Val Val Glu Ser Leu
145                 150                 155                 160
Asp Glu Ile Tyr His Thr Gly Thr Phe Ala Gln Ile His Glu Met Gln
                165                 170                 175
Asp Leu Gly Asp Lys Leu Arg Met Ile Val Met Gly His Arg Arg Val
            180                 185                 190
His Ile Ser Arg Gln Leu Glu Val Glu Pro Glu Glu Pro Glu Ala Glu
            195                 200                 205
Asn Lys His Lys Pro Arg Arg Lys Ser Lys Arg Gly Lys Lys Glu Ala
    210                 215                 220
Glu Asp Glu Leu Ser Ala Arg His Pro Ala Glu Leu Ala Met Glu Pro
225                 230                 235                 240
Thr Pro Glu Leu Pro Ala Glu Val Leu Met Val Glu Val Glu Asn Val
                245                 250                 255
Val His Glu Asp Phe Gln Val Thr Glu Glu Val Lys Ala Leu Thr Ala
            260                 265                 270
Glu Ile Val Lys Thr Ile Arg Asp Ile Ile Ala Leu Asn Pro Leu Tyr
            275                 280                 285
```

```
Arg Glu Ser Val Leu Gln Met Met Gln Ala Gly Gln Arg Val Val Asp
290                 295                 300
Asn Pro Ile Tyr Leu Ser Asp Met Gly Ala Ala Leu Thr Gly Ala Glu
305                 310                 315                 320
Ser His Glu Leu Gln Asp Val Leu Glu Thr Asn Ile Pro Lys Arg
            325                 330                 335
Leu Tyr Lys Ala Leu Ser Leu Leu Lys Lys Glu Phe Glu Leu Ser Lys
            340                 345                 350
Leu Gln Gln Arg Leu Gly Arg Glu Val Glu Glu Lys Ile Lys Gln Thr
            355                 360                 365
His Arg Lys Tyr Leu Leu Gln Glu Gln Leu Lys Ile Ile Lys Lys Glu
370                 375                 380
Leu Gly Leu Glu Lys Asp Asp Lys Asp Ala Ile Glu Glu Lys Phe Arg
385                 390                 395                 400
Glu Arg Leu Lys Glu Leu Val Val Pro Lys His Val Met Asp Val Val
            405                 410                 415
Asp Glu Glu Leu Ser Lys Leu Gly Leu Leu Asp Asn His Ser Ser Glu
            420                 425                 430
Phe Asn Val Thr Arg Asn Tyr Leu Asp Trp Leu Thr Ser Ile Pro Trp
    435                 440                 445
Gly Lys Tyr Ser Asn Glu Asn Leu Asp Leu Ala Arg Ala Gln Ala Val
450                 455                 460
Leu Glu Glu Asp His Tyr Gly Met Glu Asp Val Lys Lys Arg Ile Leu
465                 470                 475                 480
Glu Phe Ile Ala Val Ser Gln Leu Arg Gly Ser Thr Gln Gly Lys Ile
            485                 490                 495
Leu Cys Phe Tyr Gly Pro Pro Gly Val Gly Lys Thr Ser Ile Ala Arg
            500                 505                 510
Ser Ile Ala Arg Ala Leu Asn Arg Glu Tyr Phe Arg Phe Ser Val Gly
    515                 520                 525
Gly Met Thr Asp Val Ala Glu Ile Lys Gly His Arg Arg Thr Tyr Val
    530                 535                 540
Gly Ala Met Pro Gly Lys Ile Ile Gln Cys Leu Lys Lys Thr Lys Thr
545                 550                 555                 560
Glu Asn Pro Leu Ile Leu Ile Asp Glu Val Asp Lys Ile Gly Arg Gly
            565                 570                 575
Tyr Gln Gly Asp Pro Ser Ser Ala Leu Leu Glu Leu Leu Asp Pro Glu
            580                 585                 590
Gln Asn Ala Asn Phe Leu Asp His Tyr Leu Asp Val Pro Val Asp Leu
    595                 600                 605
Ser Lys Val Leu Phe Ile Cys Thr Ala Asn Val Thr Asp Thr Ile Pro
610                 615                 620
Glu Pro Leu Arg Asp Arg Met Glu Met Ile Asn Val Ser Gly Tyr Val
625                 630                 635                 640
Ala Gln Glu Lys Leu Ala Ile Ala Glu Arg Tyr Leu Val Pro Gln Ala
            645                 650                 655
Arg Ala Leu Cys Gly Leu Asp Glu Ser Lys Ala Lys Leu Ser Ser Asp
            660                 665                 670
Val Leu Thr Leu Leu Ile Lys Gln Tyr Cys Arg Glu Ser Gly Val Arg
    675                 680                 685
Asn Leu Gln Lys Gln Val Glu Lys Val Leu Arg Lys Ser Ala Tyr Lys
    690                 695                 700
Ile Val Ser Gly Glu Ala Glu Ser Val Glu Val Thr Pro Glu Asn Leu
```

```
        705                    710                      715                        720
    Gln  Asp  Phe  Val  Gly  Lys  Pro  Val  Phe  Thr  Val  Glu  Arg  Met  Tyr  Asp
                        725                      730                     735
    Val  Thr  Pro  Pro  Gly  Val  Val  Met  Gly  Leu  Ala  Trp  Thr  Ala  Met  Gly
                   740                      745                     750
    Gly  Ser  Thr  Leu  Phe  Val  Glu  Thr  Ser  Leu  Arg  Arg  Pro  Gln  Asp  Lys
              755                      760                     765
    Asp  Ala  Lys  Gly  Asp  Lys  Asp  Gly  Ser  Leu  Glu  Val  Thr  Gly  Gln  Leu
         770                      775                     780
    Gly  Glu  Val  Met  Lys  Glu  Ser  Ala  Arg  Ile  Ala  Tyr  Thr  Phe  Ala  Arg
    785                      790                     795                        800
    Ala  Phe  Leu  Met  Gln  His  Ala  Pro  Ala  Asn  Asp  Tyr  Leu  Val  Thr  Ser
                        805                      810                     815
    His  Ile  His  Leu  His  Val  Pro  Glu  Gly  Ala  Thr  Pro  Lys  Asp  Gly  Pro
                   820                      825                     830
    Ser  Ala  Gly  Cys  Thr  Ile  Val  Thr  Ala  Leu  Leu  Ser  Leu  Ala  Met  Gly
              835                      840                     845
    Arg  Pro  Val  Arg  Gln  Asn  Leu  Ala  Met  Thr  Gly  Glu  Val  Ser  Leu  Thr
         850                      855                     860
    Gly  Lys  Ile  Leu  Pro  Val  Gly  Gly  Ile  Lys  Glu  Lys  Thr  Ile  Ala  Ala
    865                      870                     875                        880
    Lys  Arg  Ala  Gly  Val  Thr  Cys  Ile  Ile  Leu  Pro  Ala  Glu  Asn  Lys  Lys
                   885                      890                     895
    Asp  Phe  Tyr  Asp  Leu  Ala  Ala  Phe  Ile  Thr  Glu  Gly  Leu  Glu  Val  His
                   900                      905                     910
    Phe  Val  Glu  His  Tyr  Arg  Glu  Ile  Phe  Asp  Ile  Ala  Phe  Pro  Asp  Glu
                   915                      920                     925
    Gln  Ala  Glu  Ala  Leu  Ala  Val  Glu  Arg
              930                      935
```

(2) INFORMATION FOR SEQ ID NO:32:

(i) SEQUENCE CHARACTERISTICS:
        (A) LENGTH: 129 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:32:

```
    Thr  Gly  Glu  Pro  Cys  Cys  Asp  Trp  Val  Gly  Asp  Glu  Gly  Ala  Gly  His
    1                   5                       10                         15
    Phe  Val  Lys  Met  Val  His  Asn  Gly  Ile  Glu  Tyr  Gly  Asp  Met  Gln  Leu
                   20                      25                      30
    Ile  Cys  Glu  Ala  Tyr  His  Leu  Met  Lys  Asp  Val  Leu  Gly  Met  Ala  Gln
              35                      40                      45
    Asp  Glu  Met  Ala  Gln  Ala  Phe  Glu  Asp  Trp  Asn  Lys  Thr  Glu  Leu  Asp
         50                      55                      60
    Ser  Phe  Leu  Ile  Glu  Ile  Thr  Ala  Asn  Ile  Leu  Lys  Phe  Gln  Asp  Thr
    65                      70                      75                         80
    Asp  Gly  Lys  His  Leu  Leu  Pro  Lys  Ile  Xaa  Asp  Ser  Ala  Gly  Gln  Lys
                   85                      90                      95
    Gly  Thr  Gly  Lys  Trp  Thr  Ala  Ile  Phe  Ala  Leu  Gly  Leu  Arg  Gly  Thr
                   100                     105                     110
    Arg  His  Pro  His  Trp  Gly  Arg  Cys  Leu  Xaa  Ser  Val  Leu  Ile  Ile  Ser
```

115 120 125

Xaa (2) INFORMATION FOR SEQ ID NO:33:

(i) SEQUENCE CHARACTERISTICS:
    (A) LENGTH: 376 amino acids
    (B) TYPE: amino acid
    (D) TOPOLOGY: linear (ii) MOLECULE TYPE: peptide (v) FRAGMENT TYPE: N-terminal (xi) SEQUENCE DESCRIPTION: SEQ ID NO:33:

```
Met Asp Met Val Glu Asn Ala Asp Ser Leu Gln Ala Gln Glu Arg Lys
 1               5                  10                  15

Asp Ile Leu Met Lys Tyr Asp Lys Gly His Arg Ala Gly Leu Pro Glu
            20                  25                  30

Asp Lys Gly Pro Glu Pro Val Gly Ile Asn Ser Ser Ile Asp Arg Phe
            35                  40                  45

Gly Ile Leu His Glu Thr Glu Leu Pro Pro Val Thr Ala Arg Glu Ala
        50                  55                  60

Lys Lys Ile Arg Arg Glu Met Thr Arg Thr Ser Lys Trp Met Glu Met
65                  70                  75                  80

Leu Gly Glu Trp Glu Thr Tyr Lys His Ser Ser Lys Leu Ile Asp Arg
                85                  90                  95

Val Tyr Lys Gly Ile Pro Met Asn Ile Arg Gly Pro Val Trp Ser Val
            100                 105                 110

Leu Leu Asn Ile Gln Glu Ile Lys Leu Lys Asn Pro Gly Arg Tyr Gln
            115                 120                 125

Ile Met Lys Glu Arg Gly Lys Arg Ser Ser Glu His Ile His His Ile
            130                 135                 140

Asp Leu Asp Val Arg Thr Thr Leu Arg Asn His Val Phe Phe Arg Asp
145                 150                 155                 160

Arg Tyr Gly Ala Lys Gln Arg Glu Leu Phe Tyr Ile Leu Leu Ala Tyr
                165                 170                 175

Ser Glu Tyr Asn Pro Glu Val Gly Tyr Cys Arg Asp Leu Ser His Ile
                180                 185                 190

Thr Ala Leu Phe Leu Leu Tyr Leu Pro Glu Glu Asp Ala Phe Trp Ala
            195                 200                 205

Leu Val Gln Leu Leu Ala Ser Glu Arg His Ser Leu Pro Gly Phe His
            210                 215                 220

Ser Pro Asn Gly Gly Thr Val Gln Gly Leu Gln Asp Gln Gln Glu His
225                 230                 235                 240

Val Val Pro Lys Ser Gln Pro Lys Thr Met Trp His Gln Asp Lys Glu
                245                 250                 255

Gly Leu Cys Gly Gln Cys Ala Ser Leu Gly Cys Leu Leu Arg Asn Leu
            260                 265                 270

Ile Asp Gly Ile Ser Leu Gly Leu Thr Leu Arg Leu Trp Asp Val Tyr
            275                 280                 285

Leu Val Glu Gly Glu Gln Val Leu Met Pro Ile Thr Ser Ile Ala Leu
            290                 295                 300

Lys Val Gln Gln Lys Arg Leu Met Lys Thr Ser Arg Cys Gly Leu Trp
305                 310                 315                 320

Ala Arg Leu Arg Asn Gln Phe Phe Asp Thr Trp Ala Met Asn Asp Asp
                325                 330                 335
```

```
        Thr   Val   Leu   Lys   His   Leu   Arg   Ala   Ser   Thr   Lys   Lys   Leu   Thr   Arg   Lys
                          340                     345                           350

Gln   Gly   Asp   Leu   Pro   Pro   Pro   Gly   Pro   Thr   Ala   Leu   Gly   Arg   Arg   Cys
                    355                           360                           365

Val   Ala   Gly   Ser   Pro   Gln   Pro   Val
              370                     375
```

( 2 ) INFORMATION FOR SEQ ID NO:34:

( i ) SEQUENCE CHARACTERISTICS:
    ( A ) LENGTH: 315 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:34:

```
        Glu   Phe   Cys   Gly   Arg   Gln   Lys   Ile   His   Lys   Glu   Met   Pro   Cys   Lys   Cys
        1                       5                         10                            15

Thr   Val   Cys   Gly   Ser   Asp   Phe   Cys   His   Thr   Ser   Tyr   Leu   Leu   Glu   His
                          20                            25                            30

Gln   Arg   Val   His   His   Glu   Glu   Lys   Ala   Tyr   Glu   Tyr   Asp   Glu   Tyr   Gly
                          35                            40                            45

Leu   Ala   Tyr   Ile   Lys   Gln   Gln   Gly   Ile   His   Phe   Arg   Glu   Lys   Pro   Tyr
                    50                            55                            60

Thr   Cys   Ser   Glu   Cys   Gly   Lys   Asp   Phe   Arg   Leu   Asn   Ser   His   Leu   Ile
        65                            70                            75                            80

Gln   His   Gln   Arg   Ile   His   Thr   Gly   Glu   Lys   Ala   His   Glu   Cys   His   Glu
                                85                            90                            95

Cys   Gly   Lys   Ala   Phe   Ser   Gln   Thr   Ser   Cys   Leu   Ile   Gln   His   His   Lys
                          100                           105                           110

Met   His   Arg   Lys   Glu   Thr   Arg   Ile   Glu   Cys   Asn   Glu   Tyr   Xaa   Gly   Gln
                    115                           120                           125

Val   Gln   Val   Ile   Ala   Gln   Ile   Leu   Ser   Cys   Asn   Lys   Glu   Val   Leu   Thr
              130                           135                           140

Arg   Gln   Lys   Ala   Phe   Asp   Trp   Xaa   Cys   Met   Gly   Lys   Glu   Leu   Gln   Ser
        145                           150                           155                           160

Glu   Ser   Thr   Ser   Ser   Ser   Thr   Ser   Glu   His   Ser   Tyr   Gln   Arg   Glu   Leu
                          165                           170                           175

Met   Asn   Val   Met   Lys   Met   Gly   Arg   Tyr   Leu   Ser   Asn   Ser   Gly   Phe   Ile
                    180                           185                           190

Gln   His   Leu   Arg   Val   His   Thr   Arg   Glu   Gln   Ile   Met   Tyr   Val   Leu   His
                    195                           200                           205

Val   Val   Lys   Pro   Ser   Val   Ile   Ala   Gln   Pro   Leu   Leu   Ser   Ile   Arg   Xaa
              210                           215                           220

Phe   Thr   Pro   Glu   Arg   Asn   Pro   Leu   Asn   Val   Thr   Asn   Glu   Glu   Lys   Val
        225                           230                           235                           240

Leu   Val   Leu   Asn   Ser   Xaa   Ser   Thr   Pro   Ala   Asn   Leu   Tyr   Gln   Xaa   Glu
                          245                           250                           255

Ile   Leu   Gln   Met   Tyr   Trp   Ile   Val   Ala   Asn   Phe   Ser   Cys   Tyr   Xaa   Tyr
                    260                           265                           270

Phe   His   Thr   Leu   Val   Thr   Cys   Gly   Gly   Ile   His   Met   Gly   Ile   Asn   Ser
                    275                           280                           285

His   Cys   Cys   Asn   Asp   Cys   Glu   Lys   His   Gln   Ala   Arg   Asn   Phe   Leu   Val
              290                           295                           300
```

Arg Phe Asn Ser Thr Pro Cys Lys Arg Phe Leu
305                 310                 315

( 2 ) INFORMATION FOR SEQ ID NO:35:

( i ) SEQUENCE CHARACTERISTICS:
        ( A ) LENGTH: 127 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:35:

Leu Phe Ala Glu Ala Gly Pro Asp Phe Glu Leu Arg Leu Glu Leu Tyr
1               5                   10                  15

Gly Ala Cys Val Glu Glu Glu Gly Ala Leu Thr Gly Gly Pro Lys Arg
                20                  25                  30

Leu Ala Thr Lys Leu Ser Ser Ser Leu Gly Arg Ser Ser Gly Arg Arg
            35                  40                  45

Val Arg Ala Ser Leu Asp Ser Ala Gly Gly Ser Gly Ser Ser Pro Ile
        50                  55                  60

Leu Leu Pro Thr Pro Val Val Gly Gly Pro Arg Tyr His Leu Leu Ala
65                  70                  75                  80

His Thr Thr Leu Thr Leu Gly Gly Val Gln Asp Gly Phe Arg Thr His
                85                  90                  95

Asp Leu Thr Leu Gly Ser His Glu Glu Asn Leu Pro Gly Cys Pro Phe
                100                 105                 110

Met Val Ala Cys Val Ala Val Trp Gln Leu Ser Leu Ser Ala Xaa
                115                 120                 125

( 2 ) INFORMATION FOR SEQ ID NO:36:

( i ) SEQUENCE CHARACTERISTICS:
        ( A ) LENGTH: 358 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:36:

Glu Phe Cys Gly Arg Gln Gln Arg Asp Glu Tyr Leu Glu Ser Phe Cys
1               5                   10                  15

Lys Phe Gly Pro Val Asn Asn Ser Thr Met Lys Ile Asp His Phe Gln
                20                  25                  30

Leu Asp Asn Glu Lys Pro Met Arg Val Val Asp Asp Glu Asp Trp Val
            35                  40                  45

Asp Gln Arg Leu Ile Ser Glu Leu Arg Lys Glu Tyr Gly Leu Thr Tyr
        50                  55                  60

Thr Asp Ser Ser Trp Cys Xaa Gln Met Trp Ile Xaa Glu Ser Ser Asn
65                  70                  75                  80

Thr Met Arg Tyr Gln Xaa Gln Xaa Ser Leu Cys Leu His Leu Ile Asp
                85                  90                  95

Thr Phe Gln Ser Arg Ile Lys Asp Met Glu Lys Gln Lys Lys Glu Gly
                100                 105                 110

Ile Val Cys Lys Glu Asp Lys Lys Gln Ser Leu Glu Asn Phe Leu Ser
            115                 120                 125

```
Arg  Phe  Arg  Trp  Arg  Arg  Arg  Leu  Leu  Val  Ile  Ser  Ala  Pro  Asn  Asp
     130                 135                      140

Glu  Asp  Trp  Ala  Tyr  Ser  Gln  Gln  Leu  Ser  Ala  Leu  Ser  Gly  Gln  Ala
145                      150                      155                      160

Cys  Asn  Leu  Gly  Leu  Arg  His  Ile  Thr  Ile  Leu  Lys  Leu  Xaa  Ala  Leu
                    165                      170                      175

Glu  Arg  Lys  Leu  Gly  Glu  Ser  Xaa  Asn  Cys  Ser  Gln  Leu  Met  Gly  Ala
               180                 185                         190

Leu  Leu  Leu  Ser  Glu  Lys  Thr  Xaa  Gln  Pro  Ile  Cys  Glu  Arg  His  Ser
          195                      200                    205

Xaa  Leu  Phe  Ser  Ser  Glu  Pro  Gly  Val  Leu  Leu  His  Ala  Ser  Ser  Arg
     210                      215                      220

Lys  Arg  Arg  Lys  Cys  Gln  Ile  Leu  Val  Ser  Phe  Pro  Asn  Val  Val  His
225                      230                      235                      240

Gly  Asp  Cys  Val  Arg  Phe  Asn  Xaa  Phe  Asp  Ala  Thr  Ser  Glu  Thr  Gly
                    245                      250                      255

Asn  Gly  Asp  Ser  Ala  Val  Thr  Gly  Asp  Ala  Leu  Pro  Arg  Arg  Xaa  Val
               260                      265                      270

Cys  Arg  Leu  Trp  Leu  Pro  Xaa  Leu  Pro  Pro  Arg  Ile  Pro  Gly  Trp  Leu
          275                      280                      285

Pro  Gly  Xaa  Leu  Pro  Ser  Ser  Xaa  Glu  Leu  Ser  Pro  Trp  Ile  Pro  Leu
     290                      295                      300

Leu  Ser  Arg  Asn  Met  Xaa  Pro  Xaa  Thr  His  His  Phe  Leu  Cys  Ser  Cys
305                      310                      315                      320

Trp  Asn  Tyr  Asp  Trp  Pro  Ala  Pro  Phe  Phe  His  Thr  Gly  Val  Leu  His
                    325                      330                      335

Phe  Leu  Ala  Phe  Ser  Phe  Lys  Gly  Phe  Ser  Leu  Gly  Leu  Lys  Xaa  Ile
                    340                      345                      350

Ser  Lys  Leu  Phe  Asn  Pro
               355
```

(2) INFORMATION FOR SEQ ID NO:37:

(i) SEQUENCE CHARACTERISTICS:
   (A) LENGTH: 120 amino acids
   (B) TYPE: amino acid
   (D) TOPOLOGY: linear (ii) MOLECULE TYPE: peptide (v) FRAGMENT TYPE: internal (xi) SEQUENCE DESCRIPTION: SEQ ID NO:37:

```
His  Tyr  Ser  Cys  Asn  Ile  Ser  Gly  Ser  Leu  Lys  Arg  His  Tyr  Asn  Arg
1              5                        10                      15

Lys  His  Pro  Asn  Glu  Glu  Tyr  Ala  Asn  Val  Gly  Thr  Gly  Glu  Leu  Ala
               20                      25                      30

Ala  Glu  Val  Leu  Ile  Gln  Gln  Gly  Gly  Leu  Lys  Cys  Pro  Val  Cys  Ser
          35                      40                      45

Phe  Val  Tyr  Gly  Thr  Lys  Trp  Glu  Phe  Asn  Arg  His  Leu  Lys  Asn  Lys
     50                      55                      60

His  Gly  Leu  Lys  Val  Val  Glu  Ile  Asp  Gly  Asp  Pro  Lys  Trp  Glu  Thr
65                      70                      75                      80

Ala  Thr  Glu  Ala  Pro  Glu  Glu  Pro  Ser  Thr  Gln  Tyr  Leu  His  Ile  Thr
                    85                      90                      95

Glu  Ser  Glu  Glu  Asp  Val  Pro  Arg  Asp  Thr  Gly  Ser  Gly  Gly  Arg  Ala
                    100                     105                     110
```

```
    Pro  Gly  Pro  Glu  Ile  Gln  Leu  Xaa
         115                      120
```

(2) INFORMATION FOR SEQ ID NO:38:

(i) SEQUENCE CHARACTERISTICS:
        (A) LENGTH: 83 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:38:

```
Glu  Arg  Glu  Arg  Glu  Arg  Glu  Arg  Glu  Arg  Glu  Arg  Glu  Arg  Glu  Arg
1                   5                        10                      15

Glu  Arg  Glu  Arg  Glu  Arg  Glu  Arg  Glu  Arg  Glu  Arg  Glu  Arg  Glu  Arg
              20                        25                      30

Glu  Arg  Glu  Arg  Glu  Arg  Glu  Arg  Glu  Arg  Glu  Arg  Glu  Arg  Glu  Arg
              35                        40                      45

Glu  Arg  Glu  Arg  Glu  Ser  Pro  Gly  Leu  Asn  Thr  Tyr  Gly  Thr  Asp  Val
         50                   55                      60

Ile  Ser  Thr  Ser  Pro  Phe  Ile  Glu  Ser  Val  Ile  Tyr  Leu  Glu  Trp  Arg
65                       70                        75                      80

His  Arg  Phe
```

(2) INFORMATION FOR SEQ ID NO:39:

(i) SEQUENCE CHARACTERISTICS:
        (A) LENGTH: 191 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:39:

```
Glu  Phe  Cys  Gly  Arg  Arg  Ser  Glu  Val  Leu  Leu  Val  Ser  Glu  Asp  Gly
1                   5                        10                      15

Lys  Ile  Leu  Ala  Glu  Ala  Asp  Gly  Leu  Ser  Thr  Asn  His  Trp  Leu  Ile
              20                        25                      30

Gly  Thr  Asp  Lys  Cys  Val  Glu  Arg  Ile  Asn  Glu  Met  Val  Asn  Arg  Ala
              35                        40                      45

Lys  Arg  Lys  Ala  Gly  Val  Asp  Pro  Leu  Val  Pro  Leu  Arg  Ser  Leu  Gly
         50                   55                      60

Leu  Ser  Leu  Ser  Gly  Gly  Asp  Gln  Glu  Asp  Ala  Gly  Arg  Ile  Leu  Ile
65                       70                        75                      80

Glu  Glu  Leu  Arg  Asp  Arg  Phe  Pro  Tyr  Leu  Ser  Glu  Ser  Tyr  Leu  Ile
              85                        90                      95

Thr  Thr  Asp  Ala  Ala  Gly  Ser  Ile  Asp  Thr  Ala  Thr  Pro  Asp  Gly  Gly
              100                       105                     110

Val  Val  Leu  Ile  Ser  Gly  Thr  Gly  Ser  Asn  Cys  Arg  Leu  Ile  Asn  Pro
              115                       120                     125

Asp  Gly  Ser  Glu  Ser  Gly  Cys  Gly  Arg  Leu  Gly  Gly  Ile  Leu  Trp  Val
         130                  135                     140

Met  Arg  Val  Gln  Pro  Thr  Gly  Ser  His  Thr  Lys  Gln  Xaa  Lys  Xaa  Cys
145                      150                       155                     160

Leu  Asp  Ser  Ile  Glu  Asn  Xaa  Arg  Arg  Ser  His  Asp  Ile  Gly  Tyr  Val
                   165                       170                     175
```

```
Lys Gln Ala Met Phe His Tyr Phe Gln Val Gln Ile Arg Xaa Val
            180                 185                 190
```

(2) INFORMATION FOR SEQ ID NO:40:

(i) SEQUENCE CHARACTERISTICS:
        (A) LENGTH: 56 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:40:

```
Gln Ser Ser Thr Glu Ile Ser Lys Thr Arg Gly Gly Glu Thr Lys Arg
1               5                   10                  15

Glu Val Arg Val Glu Glu Ser Thr Gln Val Gly Gly Ala Pro Leu Pro
            20                  25                  30

Cys Cys Val Trp Gly Leu Pro Gly Pro Gly Ala Pro Gly Ile Leu Arg
        35                  40                  45

Gln Tyr His Pro Ala Ala Gly Gly
        50                  55
```

(2) INFORMATION FOR SEQ ID NO:41:

(i) SEQUENCE CHARACTERISTICS:
        (A) LENGTH: 93 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:41:

```
Gly Glu Glu Lys Arg Val Ser Arg Glu Pro Ala Gly Val Leu Ser Gln
1               5                   10                  15

Ser Gly Met Gln Leu Glu Tyr Leu Ser Leu Pro Phe Gln Leu Pro Ala
            20                  25                  30

Arg Arg Ser Leu Gln Val Glu Leu Cys Gly Gly Gln Pro Val Leu Ser
        35                  40                  45

Arg Val Lys Val Gln Trp Arg Pro Ser Gly Ser Thr Pro Asn Val Ile
        50                  55                  60

Glu Gly Asp Leu Leu Val Phe Gly Gln Gln Leu Ala Pro Pro Met Gly
65                  70                  75                  80

Met Gly Glu Val Met Glu Glu Arg Arg Leu Cys Xaa
            85                  90
```

(2) INFORMATION FOR SEQ ID NO:42:

(i) SEQUENCE CHARACTERISTICS:
        (A) LENGTH: 84 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:42:

```
Ala Leu His Val Asn Asn Asp Arg Ala Lys Val Ile Leu Lys Pro Asp
1               5                   10                  15

Lys Thr Thr Ile Thr Glu Pro His His Ile Trp Pro Thr Leu Thr Asp
```

```
                            20                      25                      30
        Glu   Glu   Trp   Ile   Lys   Val   Glu   Val   Gln   Leu   Lys   Asp   Leu   Ile   Leu   Ala
                          35                      40                      45

Asp   Tyr   Gly   Lys   Lys   Asn   Asn   Val   Asn   Val   Ala   Ser   Leu   Thr   Gln   Ser
              50                      55                      60

Glu   Ile   Arg   Asp   Ile   Ile   Leu   Gly   Ile   Glu   Asp   Leu   Arg   Glu   Pro   Ser
        65                      70                      75                      80

Gln   Glu   Gly   Glu
```

( 2 ) INFORMATION FOR SEQ ID NO:43:

( i ) SEQUENCE CHARACTERISTICS:
    ( A ) LENGTH: 301 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:43:

```
        Glu   Phe   Cys   Gly   Arg   Leu   Leu   Asn   Val   Phe   Thr   Pro   Gln   Lys   Thr   Leu
        1                       5                       10                      15

Glu   Glu   Phe   Gln   Asp   Val   Tyr   Leu   Val   Met   Glu   Leu   Met   Asp   Ala   Asn
                          20                      25                      30

Leu   Cys   Gln   Val   Ile   His   Met   Glu   Leu   Asp   His   Glu   Arg   Met   Ser   Tyr
                          35                      40                      45

Leu   Leu   Tyr   Gln   Met   Leu   Cys   Gly   Ile   Lys   His   Leu   His   Ser   Ala   Gly
                    50                      55                      60

Ile   Ile   His   Arg   Asp   Leu   Lys   Pro   Ser   Asn   Ile   Val   Val   Lys   Ser   Asp
        65                      70                      75                      80

Cys   Thr   Leu   Lys   Ile   Leu   Asp   Phe   Gly   Leu   Ala   Arg   Thr   Ala   Cys   Thr
                                85                      90                      95

Asn   Phe   Met   Met   Thr   Pro   Tyr   Val   Val   Thr   Arg   Tyr   Tyr   Arg   Ala   Pro
                          100                     105                     110

Glu   Val   Ile   Leu   Gly   Met   Gly   Tyr   Lys   Glu   Asn   Val   Asp   Ile   Trp   Ser
                          115                     120                     125

Val   Gly   Cys   Ile   Met   Gly   Glu   Leu   Val   Lys   Gly   Cys   Val   Ile   Phe   Gln
                    130                     135                     140

Gly   Thr   Asp   His   Ile   Asp   Gln   Trp   Asn   Lys   Val   Ile   Glu   Gln   Leu   Gly
        145                     150                     155                     160

Thr   Pro   Ser   Ala   Glu   Phe   Met   Lys   Lys   Leu   Gln   Pro   Thr   Val   Arg   Asn
                          165                     170                     175

Tyr   Val   Glu   Asn   Arg   Pro   Lys   Phe   Pro   Gly   Ile   Lys   Leu   Glu   Glu   Leu
                    180                     185                     190

Phe   Pro   Asp   Trp   Leu   Phe   Pro   Ser   Glu   Ser   Glu   Arg   Asp   Lys   Ile   Lys
                    195                     200                     205

Thr   Ser   Gln   Ala   Arg   Asp   Leu   Leu   Ser   Gln   Met   Leu   Val   Ile   Asp   Pro
                    210                     215                     220

Asp   Lys   Arg   Ile   Ser   Val   Asp   Glu   Ala   Leu   Arg   His   Pro   Tyr   Ile   Thr
        225                     230                     235                     240

Val   Trp   Tyr   Asp   Pro   Ala   Glu   Ala   Glu   Ala   Pro   Pro   Pro   Pro   Ile   Tyr
                          245                     250                     255

Asp   Ala   Gln   Leu   Glu   Glu   Arg   Glu   His   Ala   Ile   Glu   Glu   Trp   Lys   Glu
                          260                     265                     270

Leu   Ile   Tyr   Lys   Glu   Val   Met   Asp   Trp   Glu   Glu   Arg   Ser   Lys   Asn   Gly
                    275                     280                     285
```

|        |        |        |        |        |        |        |        |        |        |        |        |
|--------|--------|--------|--------|--------|--------|--------|--------|--------|--------|--------|--------|
| Val    | Val    | Lys    | Asp    | Gln    | Pro    | Ser    | Ala    | Gln    | Met    | Gln    | Gln    | Xaa |
|        | 290    |        |        |        |        | 295    |        |        |        |        | 300    |

(2) INFORMATION FOR SEQ ID NO:44:

(i) SEQUENCE CHARACTERISTICS:
        (A) LENGTH: 151 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:44:

| His | Glu | Glu | Asn | Met | His | Asp | Leu | Gln | Tyr | His | Thr | His | Tyr | Ala | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Asn | Arg | Thr | Val | Glu | Arg | Phe | Glu | Ser | Leu | Val | Gly | Arg | Met | Ala | Ser |
|     |     |     | 20  |     |     |     |     | 25  |     |     |     |     | 30  |     |     |
| His | Glu | Ile | Glu | Ile | Gly | Thr | Ile | Phe | Thr | Asn | Ile | Asn | Ala | Thr | Asp |
|     |     | 35  |     |     |     |     | 40  |     |     |     |     | 45  |     |     |     |
| Asn | His | Ala | His | Ser | Met | Leu | Met | Tyr | Leu | Asp | Asp | Val | Arg | Leu | Ser |
|     | 50  |     |     |     |     | 55  |     |     |     |     | 60  |     |     |     |     |
| Cys | Thr | Leu | Gly | Phe | His | Thr | His | Ala | Glu | Glu | Leu | Tyr | Tyr | Leu | Asn |
| 65  |     |     |     |     | 70  |     |     |     |     | 75  |     |     |     |     | 80  |
| Lys | Ser | Val | Ser | Ile | Met | Leu | Gly | Thr | Thr | Asp | Leu | Leu | Arg | Glu | Arg |
|     |     |     |     | 85  |     |     |     |     | 90  |     |     |     |     | 95  |     |
| Phe | Ser | Leu | Leu | Ser | Ala | Arg | Leu | Asp | Leu | Asn | Val | Arg | Asn | Leu | Ser |
|     |     |     | 100 |     |     |     |     | 105 |     |     |     |     | 110 |     |     |
| Met | Ile | Val | Glu | Glu | Met | Lys | Gly | Gly | Asp | Thr | Gln | Asn | Gly | Glu | Ile |
|     |     | 115 |     |     |     |     | 120 |     |     |     |     | 125 |     |     |     |
| Leu | Arg | Asn | Val | Thr | Ser | Tyr | Glu | Val | Pro | Pro | Ala | Ser | Arg | Thr | Lys |
|     | 130 |     |     |     |     | 135 |     |     |     |     | 140 |     |     |     |     |
| Arg | Phe | Lys | Arg | Asp | Leu | Ala |
| 145 |     |     |     |     | 150 |     |

(2) INFORMATION FOR SEQ ID NO:45:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:45:

| Ser | Arg | Gly | Phe | Glu | Gly | Gln | Gly | Arg | Arg | Gly | Leu | Phe | Arg | Gln | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Arg | Arg | Lys | Lys | Glu | Glu | Gly | Leu | Ala | Gly | His | Gln | Arg | Val | Gly | Arg |
|     |     |     | 20  |     |     |     |     | 25  |     |     |     |     | 30  |     |     |
| Thr | Ala | Cys | Ala | Arg | Arg |
|     |     | 35  |     |     |     |

(2) INFORMATION FOR SEQ ID NO:46:

(i) SEQUENCE CHARACTERISTICS:
        (A) LENGTH: 143 amino acids
        (B) TYPE: amino acid
        (D) TOPOLOGY: linear (ii) MOLECULE TYPE: peptide ( v ) FRAGMENT TYPE: internal ( x i ) SEQUENCE DESCRIPTION: SEQ ID NO:46:

| Arg | Arg | His | Pro | Ser | Arg | Ser | Gly | Leu | Gly | Arg | Gln | Gly | Lys | Met | Val |
| 1 | | | | 5 | | | | | 10 | | | | | 15 | |
| Asp | Tyr | Ser | Val | Trp | Asp | His | Ile | Glu | Val | Ser | Asp | Asp | Glu | Asp | Glu |
| | | | 20 | | | | | 25 | | | | | 30 | | |
| Thr | His | Pro | Asn | Ile | Asp | Thr | Ala | Ser | Leu | Phe | Arg | Trp | Arg | His | Gln |
| | | 35 | | | | | 40 | | | | | 45 | | | |
| Ala | Arg | Val | Glu | Arg | Met | Glu | Gln | Phe | Gln | Lys | Glu | Lys | Glu | Glu | Leu |
| | 50 | | | | | 55 | | | | | 60 | | | | |
| Asp | Ser | Gly | Cys | Arg | Glu | Cys | Lys | Arg | Lys | Val | Ala | Glu | Cys | Gln | Arg |
| 65 | | | | | 70 | | | | | 75 | | | | | 80 |
| Lys | Leu | Lys | Glu | Leu | Glu | Val | Ala | Glu | Gly | Gly | Lys | Ala | Glu | Leu | Glu |
| | | | | 85 | | | | | 90 | | | | | 95 | |
| Arg | Leu | Gln | Ala | Glu | Ala | Gln | Gln | Leu | Arg | Asn | Glu | Glu | Arg | Ser | Trp |
| | | | 100 | | | | | 105 | | | | | 110 | | |
| Glu | Gln | Lys | Leu | Glu | Glu | Met | Arg | Lys | Lys | Glu | Lys | Ser | Met | Pro | Trp |
| | | 115 | | | | | 120 | | | | | 125 | | | |
| Gln | Arg | Gly | His | Ala | Gln | Gln | Arg | Arg | Leu | Gln | Gln | Arg | Ala | Trp | |
| | 130 | | | | | 135 | | | | | 140 | | | | |

( 2 ) INFORMATION FOR SEQ ID NO:47:

( i ) SEQUENCE CHARACTERISTICS:
( A ) LENGTH: 77 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:47:

| Glu | Arg | Glu | Arg | Glu | Arg | Glu | Arg | Glu | Arg | Glu | Arg | Glu | Arg | Glu | Arg |
| 1 | | | | 5 | | | | | 10 | | | | | 15 | |
| Glu | Arg | Glu | Arg | Glu | Arg | Glu | Arg | Glu | Arg | Glu | Arg | Glu | Arg | Glu | Arg |
| | | | 20 | | | | | 25 | | | | | 30 | | |
| Glu | Arg | Glu | Arg | Glu | Arg | Glu | Arg | Glu | Arg | Glu | Arg | Glu | Ser | Leu | Tyr |
| | | 35 | | | | | 40 | | | | | 45 | | | |
| Asp | Leu | Ser | Ile | Gln | Asn | Phe | Gln | Val | Ser | Pro | Tyr | Val | Glu | Pro | Lys |
| | 50 | | | | | 55 | | | | | 60 | | | | |
| Ser | Phe | Phe | Leu | Pro | Arg | Asn | Phe | Thr | Thr | Ile | Arg | Xaa | | | |
| 65 | | | | | 70 | | | | | 75 | | | | | |

( 2 ) INFORMATION FOR SEQ ID NO:48:

( i ) SEQUENCE CHARACTERISTICS:
( A ) LENGTH: 72 amino acids
( B ) TYPE: amino acid
( D ) TOPOLOGY: linear ( i i ) MOLECULE TYPE: peptide ( v ) FRAGMENT TYPE: N-terminal ( x i ) SEQUENCE DESCRIPTION: SEQ ID NO:48:

| Met | Ser | Asp | Ser | Asn | Cys | Glu | Ser | Gln | Phe | Phe | Gly | Val | Lys | Val | Glu |
| 1 | | | | 5 | | | | | 10 | | | | | 15 | |
| Asp | Ser | Thr | Ser | Thr | Val | Leu | Lys | Arg | Tyr | Gln | Lys | Leu | Lys | Pro | Ile |
| | | | 20 | | | | | 25 | | | | | 30 | | |

```
Gly  Ser  Gly  Ala  Gln  Gly  Ile  Val  Gly  Ala  Ala  Ser  Gly  Thr  Val  Leu
          35                      40                      45

Gly  Asp  Lys  Cys  Trp  Ser  Gln  Gly  Ile  Lys  Pro  Ala  Pro  Phe  Gln  Asn
     50                      55                      60

Pro  Thr  His  Glu  Arg  Glu  Phe  Ser
65                       70
```

( 2 ) INFORMATION FOR SEQ ID NO:49:

( i ) SEQUENCE CHARACTERISTICS:
        ( A ) LENGTH: 548 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:49:

```
CCCAGGTTTA  ATGATTTATT  TAACTGGTGG  GAACAAAAAT  TAACCCAGAT  TACCCACACC      60
CATGCCTAAC  TTTATCAATT  GTTTAGGAGG  TAATTTTGAT  TCTTATTTGA  AAAAATGTTC     120
CATCCATTAT  AAACAATTCC  CAATAATCCG  GTCAATTATT  TTCCTAAATT  TCCCCCCAAT     180
TCCTTAGGAG  AGGATGTAAT  TGGGAGGTAA  CTTTTGGACG  GCTTACTATC  TTAACAAGNT     240
TGGGGTGAAG  GGTTGAGGAG  TCCAAACCCT  TCCAGATGG   TGGGNGNNGG  GTNAAGGAAT     300
TCCCTTTNTC  CCCCCCCCC   NNNGGGGNCN  GCCCCCCCC   NGGGNCCCC   CNGGGGGGAA     360
CCCNCTCCNG  TTTNAANAAA  AAANNGGGGG  GAGAGNCCNA  NAGCGGGGGT  TTTTTTTGGG     420
GGGCCCCCCC  CCCCCCNCCN  AAANTTCTCC  CCCCCNAGNG  GGGGAAANNG  NCNNCNCNTT     480
TTCACTNCNA  CNNCTNCNCC  NGCNNNGGGG  GGGGGGTTCC  CCCCCCCNC   NCGGGNCCCC     540
CCCCCCCC                                                                  548
```

( 2 ) INFORMATION FOR SEQ ID NO:50:

( i ) SEQUENCE CHARACTERISTICS:
        ( A ) LENGTH: 239 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

```
TCCCCCAAGT  CCAAATTTTT  TTTTTCCTCT  GATTGGGGAT  GATTTTAGG   GGGAAGGGAA      60
ATTGATTTTC  AAAAGGTTTT  TTGGAAAATC  CATTTAAATC  CTGGTTTTTT  CCTTAAAAGT     120
TTCAGAAAGG  TAAAATTTTG  AACTAAAAAG  GAAGGGAGGC  CGTAACAAGG  TTTTGGGTGT     180
TGAGATTAAT  TGAACAGGGA  TTTTTAACAT  GGTTTTGGTT  TACAACTGGG  GGAATANAA     239
```

( 2 ) INFORMATION FOR SEQ ID NO:51:

( i ) SEQUENCE CHARACTERISTICS:
        ( A ) LENGTH: 379 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:51:

```
GGGTGATCAT  GCACAAGTCT  TAATTTATTG  GGTAAAAACA  TTAATTTATT  ACAACATTTT      60
TCCCAATAAA  GCATAATAAA  TAGAATCCAT  TTCTTTTAAA  ACGCTGTACA  AGAGACTGGA     120
```

```
AAACAAGCTC  CCAACAGAAT  ATGAATAACT  CATAACTCAT  CCTACCTTCT  TATTGATTGG    180
GGACGCTCCC  CCCACCCCCC  ATGCCTGAAG  CAACGTGCAC  ACTTCAGGTC  TCTGARCACA    240
GCCGGCCAAG  GCCACCAGCT  TCTAGGSTCC  CTGGAGGTCA  TGACTTCACT  CTTAAATGCT    300
CTGCCCTTGG  GTCTCGTCTT  AGGCCCAGGA  GGCTGAGGGC  AGGAGAACTG  ACCCGTTAGG    360
TGGTTGTGGC  CTGGAGGAG                                                    379
```

(2) INFORMATION FOR SEQ ID NO:52:

(i) SEQUENCE CHARACTERISTICS:
        (A) LENGTH: 296 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

```
ATCAGTCTGA  TGTAGCTTTT  ATTGAGTAAA  GGAAAAGGG   AATTCAGCCG  CATGATACAG     60
AGGTTCCAGT  TGATCAGAGT  GCGCAAACAC  CCTTCCTGTC  TGCGTGATGG  GAACCGCACC    120
AGCACACGGG  GTACGCGGAA  GCCACTGCCG  CAAGGAGATG  GTTCCCACTC  TCACGCACAT    180
GAGCAGCTCC  TGGTCAGTCC  CAAGAGGCAA  GGGCAGAGGG  CATGGTGGCT  CTCACAGAGC    240
TACTTTACAA  ATAAACTGTG  TGTCTTCCTC  AGGAGTCTCT  TACAACACTT  TTAAAA        296
```

(2) INFORMATION FOR SEQ ID NO:53:

(i) SEQUENCE CHARACTERISTICS:
        (A) LENGTH: 365 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

```
AACTATTTTA  ATTAGAATTT  TTATTTGGTG  CTTCAGGGCC  ACAGGATAAA  ATAACTACAT     60
TTAGCTTGCC  TTTCAGTGAC  GCTTTGGCCA  AATGTCAGCT  ACAAGGAGTC  ATCTCCCTCA    120
CCGCCAAGCT  GTCTAGCAGC  CAGAGTGGTA  GCTTTACTGT  AACACACAGT  ACTTTTGGTA    180
ATCAGACTCA  AAGTCTTCAT  CCATACTGCT  TGTGTCTGCC  ATCTTTTGGG  CATCAGTCTT    240
GGGCAGAAAT  TGTGCATAGT  CTATCCCCTG  CTGCTCATAG  AAAAGATTGT  AGGCAGAGTC    300
GGGTGTCAAT  TTCATCCGGG  TGAAGTTCCT  TACAGCTGCT  GTCATTGTAC  AAGTACCACT    360
TGCAG                                                                    365
```

(2) INFORMATION FOR SEQ ID NO:54:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

```
CCAGAATACC  AAACACACCT  TTATCCAGGT  GGAAGTACAA  AAGCACATCC  CTAAACCAAA     60
CGCATACATG  TGATTTTTAC  ATTTCCTGTT  TTTAGGGAT   TACATAATCC  TGTTTCAGTC    120
ACCATACGTG  ACTACTGGTC  TCTATACATA  AGGGTATACA  TGTTGGACAG  GAAAAAACAC    180
```

```
ATGCATTTTC CATTGGCTTT TACATTTRGA TCACTCCATT TATTTTTCAA TTTCATTTAG      240

ATTCCTACCT GGCCTGGATG AAATCCTACT CTKGCTGATG GCAAAGAAGT AAAATATAGT      300

GGCAGAACTA TCCTAGAGGG TTAGCCATAG GGGGATTAT                             339
```

( 2 ) INFORMATION FOR SEQ ID NO:55:

( i ) SEQUENCE CHARACTERISTICS:
        ( A ) LENGTH: 529 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:55:

```
AGCCATAGGA GTTATAGAGT GAGCAACATA TTTGTATGTA TTTGTTGAGG GTCCCTACTG       60

AATATTATAA CACTGCAACT ATGAAAGCCT CAATTGCTGG ACTGACAACA AGAATTTTAA      120

ATAACATTTG TCTTACTCAC AAAATGTTAT AAAGCTTAAG ATGGAAAAAT ACAAAATGTT      180

GGACATTAC CTAAAGAATC ATGAACTCTT GTTAGGTATA TGATGGTGGC CCTGAACTTG       240

AGCCAACATC TTGTAATCAC TTTTATCAGT CAAAAAGCCA TGTTCTTTTA TATAGCCTGT      300

AGACTATTAA AATACAAAAA TGTGGTAATG GATAAACAAC TATACACAAA GCCCTCACAC      360

TTCAAATACT GTCCTGGATT GATGAGAGAG GAGCAGAATT CAACCATTTA TCTGCAATCC      420

TAATGGGTAA AATTTTACCA GGAACAGACC TGCACTCTCT GAATACTGCT CTGAGATTAC      480

ATACGACAGG ATCATCTCTT GTTGGGAGGC TACATCCCCT ATGAGCGAT                  529
```

( 2 ) INFORMATION FOR SEQ ID NO:56:

( i ) SEQUENCE CHARACTERISTICS:
        ( A ) LENGTH: 386 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:56:

```
GGCTGTTAAA TAACTTTAAT GGTTGATGTG GGAGTCACAA GGGAGGTATG TTGGCTCCAA       60

GGGTTCTCCA GTGCCATCCT CAAAGCTGGT TAGTGAAGGG AGGTAGGGAA GAGTTGGTTC      120

CAGTTTTCTC CCAGGAAGGG TTTAGGGAGG TCCCAGCGAG CCCCAGGAAT GAGTCCCTCG      180

GTACCATGGA AACCACAATT TAAGAGGGGC TTCTGCCCAC CCCTGCAGCC TACCCCAGGT      240

CCAGCAGAGG AACAGGAGGC CAGACTGGCC AACTTGCTAT AGACAGCGCC GTATCCAGAG      300

CCCAACTGCG CATGGGTCAT TTTCTCTTCT GGGCAGATCC TATGCCAGAC CTTCTCTCTC      360

ACACTGGTGA CTTGGAGCCA AGTGCG                                           386
```

( 2 ) INFORMATION FOR SEQ ID NO:57:

( i ) SEQUENCE CHARACTERISTICS:
        ( A ) LENGTH: 306 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:57:

```
AAGGTGAAAG TTGGCTATTT ATTTAGTCTT AGAAAAACAC TGAAAGAAAA AGGCAGGAAA       60

TGTAGTACGC AGTGTGGGAA GAATGGGGGC TGGCCACATG TAGTTTTAGC AAGCTGCAGA      120
```

```
GGAAACCTGG CTGAGTTCTA AGGTTACAAT TTTTCTTGTT CAGGAAGGGG TTTCCAAGGG      180

GAATACCTCT CATGATGGAC GGGAGCCAAT CCCGGTAACC CACCCCGGGT TTCCCGGGGG      240

GGTAACTTTG GGAAACCCAT GGCCTGGAAT CCTCATCTTT CCTGGGAAGG GGCATCCCCA      300

GGGGAA                                                                 306
```

( 2 ) INFORMATION FOR SEQ ID NO:58:

( i ) SEQUENCE CHARACTERISTICS:
        ( A ) LENGTH: 471 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:58:

```
CTGCGAAAGC CGAACTTTTT TGGGGGTTTC CCACCTAAGA AGTTCCCAGT TGAGTTGAAT       60

GAAATGTGAA AAAGTCCCCT AGAAAGTTGG GCCTCGCAGT GTGTAAAAAA GGCCCCCCAT      120

GGGGAAGAGC CGTGAAACCA TTTTAAAAAA AGAGAAAGTG AGAGAGAATT CAGGCCCCCT      180

GGGAGCCTGG TTTGGGTGGA GTGAACATCG TTCAGGCCGG CCCATGTGCC AGGCCACTCC      240

TGTTGGTTCG GGGGCTGTTT TCTTCTCTAA TTGTGCTTTC CCNNCCAAGT CCTAAAANCT      300

CTGGGGTTGN GGCCACCAGA NAGACCAGAC CAANTCCCCG GGGTNAAGAG GGTTTNTTNC      360

CTNGGCGAAG TTGGNGGTGC CCCAAAAAAG NNACCCNAAA AANTNTTCCC CCCTTTCAGC      420

CCCCCNGANN CAAGGTTCCC TGGCNNGANC CCCCAACCCT NTTCCCACC C                471
```

( 2 ) INFORMATION FOR SEQ ID NO:59:

( i ) SEQUENCE CHARACTERISTICS:
        ( A ) LENGTH: 463 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:59:

```
ATACAAAATT TATTATTATA TTTTATTCAG GATGACAAGC CATCAGGAGG TCAACAACAC       60

AAGCACAGAC AGAGGGAAAG AGGGCAACCT GCTGAATGTC AGGGGCTGTC TTGAGGGGTT      120

GAGGGTTCCG CCCTCGGGAG GGTTGAGGAA GAGGGAAGGG AACCGGCAAG GATTCAAGTT      180

CCCCCCCTCC CGAGGGGTAA CCCTCCCCTC CTAAGGAGAA AAGTTGAGGG ATGTGAGAGG      240

CCTTTAACCC GTGCGGAGAT CTCTGTGGTG CCCCCCCAGT TGGNCTCATT TNCATTTGGG      300

GGACAACCCC CACACCCATA NGNTNGNNGT NCCCNCGNGG TCTTGNGAGG NCCCNTNNGG      360

NCGCCAAGGA ANNGCCCCAA AAGAAGATNT TCACCCTNTC ATTGNTTNAA GGAAGTCCCN      420

TGGGNNNNGC CGCCTCTTTT TTTCNTTGGG CCCCTCCCNN CCC                        463
```

( 2 ) INFORMATION FOR SEQ ID NO:60:

( i ) SEQUENCE CHARACTERISTICS:
        ( A ) LENGTH: 392 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:60:

```
GAATTCGGCA CGAGGTTTTT TTTTTTTTT TTTTTTTTT TTTTTGAAT GGGGTTATCC      60
AGGATGTGAC TTTGGGAGAT TGGTTTTTTC CGTGGATTAT CCTGCCCCTG AGATCCACCC     120
AAGTTGTGGG ATCTGAAACT GGCCCACCCT CCGGGATTTT GAAGGACGCT GAATCATGAG     180
CGACAGTAAT TGTGAAAGCC AGTTTTTGG  TGTGAAAGTG GAAGACTCAA CCTCCACTTG     240
TCCTAAAACG GTTACCAGAA GTTGAACCCA ATTGGTTCCT GGGGCCCAAG GGATTGTTGG     300
GTGTTGCATT GGGTACAGCC CTTGGGATAA TTGTTGGAGG CCAAGAAATT AGGCCCCCCT     360
TTCCAGACCC AACTCATGAA AGGGAGTTCT CC                                  392
```

( 2 ) INFORMATION FOR SEQ ID NO:61:

( i ) SEQUENCE CHARACTERISTICS:
    ( A ) LENGTH: 506 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:61:

```
TTGACCAAAC CTCTGGCGAA GAAGTCCAAA GCTTCTCGAG GGCCAACAGG GCCCCTTTCT      60
CCCACAGGCC CGGCCTCTCC AGGTTGTCCC TGAGGACCCT GGGTCCCAG  GGGGCCCAAG     120
CTGCCGGGGT CTCCTTTCGG GCCTCTGCCG CCAACAGGCC CTTTCACGCC CATATCTCCT     180
TGGAATCCTC TTGGTCCTGG AGGGCCGGGG GCACCTCGTA GGATGGTGAC ATTGCGAAGG     240
ATTTCTCCAT GCTGTGTGTC CACTGCCTTC ATCTCCTCCA CGATCATGGA GAGGTTCCGG     300
ACGTTGAGGT CCAGCCGGGC ACTGAGCAGG CTGAAGCGCT CCCGGAGCAG GTCTGTGGTG     360
CCCAGCATGA TGGAGACAGA CTTGTTCAGG TAGTAGAGCT CCTCGGCATG GGTGTGGAAG     420
CCCAGCGTGC AGGAGAGCCG AACGTCATCC AGGTACTTGG AGCATGTTGT GCACGTGGTG     480
GTCGGTGGAA TTGATGTTGG TGAAGA                                         506
```

( 2 ) INFORMATION FOR SEQ ID NO:62:

( i ) SEQUENCE CHARACTERISTICS:
    ( A ) LENGTH: 474 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:62:

```
CCAAAGGCAT TCAGGCTCTT TAATGTCTGA GGATGGGGGG AAGAAGTCAA TGGTGAGGCT      60
CCTCTGGGAA ATTCTGAAGG CCTGGTGGTT CTCTAAGCCC CTCTAGCAAC ATGTGGATAT     120
GGGCTTGGAT ATCCATGGAG TCCTTGGTGA GGCTGTTGCT GAGCTCTGTG AGGAGAGAGC     180
TCTTACGACC AATGAACTGG AGAGCTTCTG CCAGTGTCAC CTCCAGGAAA AACCATATC     240
CCAGGGCCAC ATAGATGCGT GAAGTATCTG GGACCACTGT GTCAACGAAG AAGTTACAGC     300
CCAAATCCAC CTGCATATAT AACTCCGAGT GCTTAGCTTC CTGGAGTCGC TCAATGACAT     360
TTCTCAGTTG AGGGTATTTG GCCAGCTGTT CATATACCTG GTCTCGATGG TCCAGAACTT     420
TCGGAAGTCC CGCTGCAGAA CGTCACTGAT GAAGGGCTCG TGGGGAGAAT TTCT           474
```

( 2 ) INFORMATION FOR SEQ ID NO:63:

( i ) SEQUENCE CHARACTERISTICS:
    ( A ) LENGTH: 454 base pairs
    ( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:63:

| | | | | | |
|---|---|---|---|---|---|
| TGGCATCTGA | AATCTTTTAT | TGGAAGATCA | TTGTTGTTTG | CCAATTAGAA | GACACAGACA | 60 |
| GCAGACGAAC | AGTGAAAACA | GAGCCCAGTG | ACGAGAGCCG | GCCCCTTGGT | TGGGGACCCT | 120 |
| CCCCAACTAC | CTGGTAGACC | AGCCTGGTGA | CCTCTGCCCT | TCCCCGGACC | CCCGGGCCTT | 180 |
| TGGCATAATG | CTGATGGGGG | GCTGCAGGCA | GTGAAGCCCC | TTGACTCAAA | GCAGAGACTT | 240 |
| GATTGGGCGC | TGGAGAGTGG | AGACAGTGGA | GAGGCCAGGG | AGGGCTGGGC | GGGCCCCCA | 300 |
| GGCTGGGCCG | AGCAGCGCAA | GTAGAGGAAG | TCAGGAGCGG | GCGAGATGGC | ATCTATCTTG | 360 |
| TTTTCTTGAA | AAGGGGGCAC | ATAGGGGGCC | TGGGAAGCAG | GTGGCGGGTG | GGTAGCTTGG | 420 |
| GGAAGGTCAA | CACACTGAAC | ATCCTTCTTC | ATCG | | | 454 |

( 2 ) INFORMATION FOR SEQ ID NO:64:

( i ) SEQUENCE CHARACTERISTICS:
    ( A ) LENGTH: 307 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:64:

| | | | | | |
|---|---|---|---|---|---|
| AGTGATTATG | CTTTTATTTA | TTTCCAACTT | CTTATGGGTA | ACATAATTTC | CAGACAATGT | 60 |
| TAGCTGTTTT | TAATCCATCA | GTAAACTGCA | TTAAGATTCT | TAATAAACAA | ACACTGANGG | 120 |
| CCTCTTCCAT | ATTGGTTTCA | TCTGCATTTT | TTTTTATATG | CTGGTCATGT | GGCTTTACTT | 180 |
| TCAGCCTCAC | TCTTTTCTTC | TTCCAAATGG | ATTATCCTTA | AACCTTTTAC | CTTTAAAGAG | 240 |
| CCTGAGATTT | ATATTTAACT | CGAACAACAG | TTGGGCTCTG | TTGGCCCTGT | GTTCATGTTT | 300 |
| TCCTAAG | | | | | | 307 |

( 2 ) INFORMATION FOR SEQ ID NO:65:

( i ) SEQUENCE CHARACTERISTICS:
    ( A ) LENGTH: 319 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:65:

| | | | | | |
|---|---|---|---|---|---|
| CCCCCTTTAA | GTGTTACACT | TTTTTTAAA | ACTTAACATT | TCAGGAGGTC | ATACGCATAC | 60 |
| ACCTCAAACT | GCAAAAAATT | CCAGGCATAA | AAACTATTAT | CTGGGTTAGT | GTGCCATCTT | 120 |
| TCTTCTCCAA | ATGTCAAACT | GTCCACAAAA | AAAGTCTTAA | GAAAGTCAAT | TCCACTGTCC | 180 |
| ATTGGTGTGG | GGTAAGAAAC | CTATGTCTCA | TCCACTGCAT | GGAATCCATG | TTAAAAGAAC | 240 |
| CCTGCCTTGG | TTGTTTATCA | TCACAGGACT | CTTGTGTTAA | TCCATTCTCC | CTCAATTCCC | 300 |
| CACAGTAGAC | TGCCATCTT | | | | | 319 |

( 2 ) INFORMATION FOR SEQ ID NO:66:

( i ) SEQUENCE CHARACTERISTICS:
    ( A ) LENGTH: 504 base pairs
    ( B ) TYPE: nucleic acid
    ( C ) STRANDEDNESS: single ( D ) TOPOLOGY: linear ( i i ) MOLECULE TYPE: cDNA ( x i ) SEQUENCE DESCRIPTION: SEQ ID NO:66:

| | | | | | |
|---|---|---|---|---|---|
| GAATTCTGCG | GCCGCCTCCT | GAGCAAAAGC | CCATCCTCAC | TCAGCGCTAA | CATCATCAGC | 60 |
| AGCCCGAAAG | GTTCTCCTTC | TTCATCAAGA | AAAGTGGAA | CCAGCTGTCC | CTCCAGCAAA | 120 |
| AACAGCAGCC | CTAATAGCAG | CCCACGGACT | TTGGGGAGGA | GCAAGGGAG | GCTCCGGCTG | 180 |
| CCCCAGATTG | GCAGCAAAAA | TAAACTGTCA | AGTAGTAAAG | AGAACTTGGA | TGCCAGCAAA | 240 |
| GAAAATGGGG | CTGGGCAGAT | ATGTGAGCTG | GCTGACGCCT | TGAGTCGAGG | GCATGTGCTG | 300 |
| GGGGCAGCC | AACCAGAGTT | GGGTCACTCC | TCAGGACCAT | GAGGTAGCTT | TGGGCCAATG | 360 |
| GATTCCTTTA | TGAGCATGAG | GAATGTAGCA | ATGGTTACAG | CAATGGTCAG | CTTGGAACCA | 420 |
| CAGTGAGGAG | AAAGCACTGA | TGACCAAGAG | GAGATCTTCG | TTTAAGCCTA | TTTATATCTA | 480 |
| TATGAATTCG | GGCAATCAGA | TTCT | | | | 504 |

( 2 ) INFORMATION FOR SEQ ID NO:67:

( i ) SEQUENCE CHARACTERISTICS:
   ( A ) LENGTH: 504 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:67:

| | | | | | |
|---|---|---|---|---|---|
| GAATTCTGCG | GCCGCCTCCT | GAGCAAAAGC | CCATCCTCAC | TCAGCGCTAA | CATCATCAGC | 60 |
| AGCCCGAAAG | GTTCTCCTTC | TTCATCAAGA | AAAGTGGAA | CCAGCTGTCC | CTCCAGCAAA | 120 |
| AACAGCAGCC | CTAATAGCAG | CCCACGGACT | TTGGGGAGGA | GCAAGGGAG | GCTCCGGCTG | 180 |
| CCCCAGATTG | GCAGCAAAAA | TAAACTGTCA | AGTAGTAAAG | AGAACTTGGA | TGCCAGCAAA | 240 |
| GAAAATGGGG | CTGGGCAGAT | ATGTGAGCTG | GCTGACGCCT | TGAGTCGAGG | GCATGTGCTG | 300 |
| GGGGCAGCC | AACCAGAGTT | GGGTCACTCC | TCAGGACCAT | GAGGTAGCTT | TGGGCCAATG | 360 |
| GATTCCTTTA | TGAGCATGAG | GAATGTAGCA | ATGGTTACAG | CAATGGTCAG | CTTGGAACCA | 420 |
| CAGTGAGGAG | AAAGCACTGA | TGACCAAGAG | GAGATCTTCG | TTTAAGCCTA | TTTATATCTA | 480 |
| TATGAATTCG | GGCAATCAGA | TTCT | | | | 504 |

( 2 ) INFORMATION FOR SEQ ID NO:68:

( i ) SEQUENCE CHARACTERISTICS:
   ( A ) LENGTH: 365 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:68:

| | | | | | |
|---|---|---|---|---|---|
| AACTATTTTA | ATTAGAATTT | TTATTTGGTG | CTTCAGGGCC | ACAGGATAAA | ATAACTACAT | 60 |
| TTAGCTTGCC | TTTCAGTGAC | GCTTTGGCCA | AATGTCAGCT | ACAAGGAGTC | ATCTCCCTCA | 120 |
| CCGCCAAGCT | GTCTAGCAGC | CAGAGTGGTA | GCTTACTGT | AACACACAGT | ACTTTTGGTA | 180 |
| ATCAGACTCA | AAGTCTTCAT | CCATACTGCT | TGTGTCTGCC | ATCTTTTGGG | CATCAGTCTT | 240 |
| GGGCAGAAAT | TGTGCATAGT | CTATCCCCTG | CTGCTCATAG | AAAAGATTGT | AGGCAGAGTC | 300 |
| GGGTGTCAAT | TCATCCGGG | TGAAGTTCCT | TACAGCTGCT | GTCATTGTAC | AAGTACCACT | 360 |

TGCAG ( 2 ) INFORMATION FOR SEQ ID NO:69:

( i ) SEQUENCE CHARACTERISTICS:
        ( A ) LENGTH: 444 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:69:

```
GAATTCTGCG GCCGNCGGGC ACAGGCAGTG CTGGAGGAAG ACCACTACGG GATGGAGGAC      60
GTCAGGAAAC GCATCCTGGA GTTCATNGCC GTTAGCCAGC TCCGCGGNTC CACCCAGGGC     120
AAGATCCTCT GCTTCTATGG CCCCCCTGGC GTGGGTAAGA CCAGCATTGG TCGCTCCATC     180
GNCCGCGCCT GACCGAGAGT ACTTCCCGCT TCAGNGTCGG GGGGATTATG ACGTNGGTGA     240
GATCAAAGGG CACAGGGGGC CTCCGTGGGC GCCATTCCGG AAGATCATCC ANTNTTGGGG     300
AAGACCAAAN GGNGAACCCC TTATTCCNCA TCGAGAAGGN GGNAAAAATC GNCCANGTTA     360
CNAGGGGCCC CCNNNTCGNA ATTNTTNTGT TTTTTACCA  ANAAAAATNT CATTTCCCNG     420
ACCNTNCTGG GGGTCCCCTN ANTT                                            444
```

( 2 ) INFORMATION FOR SEQ ID NO:70:

( i ) SEQUENCE CHARACTERISTICS:
        ( A ) LENGTH: 423 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:70:

```
ACTGAAAATG ACTTTAATCA TTAAATAGCT TCTATGCCAC ACTCTGATTA AGCCGACTGA      60
GGTCCCTGGG ATCTGGGTCA CTGGACCGAG CTGCTCGCTC GGTGGCTCCA CTGCCAGGTC     120
CGGGCGCGCT CCCCACAGGG GTCAGTCTTG GCCAGACAGG GCTGANATCC GCGCCTGAAG     180
TCCGGGTGGG CCGCACCGTC CACGGCAGGG CTCTGCTTTC GCCGGGAGGG GAAGTCGAGG     240
TCTCCCGNNG GGTCCAGAAG GGAACCCCA  GGCCCGGGG  ATNAAGTNC  CAGGCGGGAA     300
AGTCCCCTTT TCTCNGTTGG AANAAAAAA  AANAACCCCN NGNGCTTGGG NNAAAGGCCT     360
NCTCCTGGNG GNCNACANAN NAAGATNTTN CCCGNGGGGG ATTCCCAAA  NAAANCAAAT     420
TTT                                                                   423
```

( 2 ) INFORMATION FOR SEQ ID NO:71:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:71:

```
TACCAGCCTC TTGCTGAGTG GAGA                                             24
```

( 2 ) INFORMATION FOR SEQ ID NO:72:

( i ) SEQUENCE CHARACTERISTICS:
        ( A ) LENGTH: 24 base pairs ( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:72:

TAGACAAGCC GACAACCTTG ATTG      24

( 2 ) INFORMATION FOR SEQ ID NO:73:

( i ) SEQUENCE CHARACTERISTICS:
( A ) LENGTH: 345 base pairs
( B ) TYPE: nucleic acid
( C ) STRANDEDNESS: both
( D ) TOPOLOGY: linear ( i i ) MOLECULE TYPE: cDNA ( i x ) FEATURE:
( A ) NAME/KEY: CDS
( B ) LOCATION: 7..327

( x i ) SEQUENCE DESCRIPTION: SEQ ID NO:73:

```
AAGCTT ATG GGT GCT CCT CCA AAA AAG AAG AGA AAG GTA GCT GGT ATC              48
       Met Gly Ala Pro Pro Lys Lys Lys Arg Lys Val Ala Gly Ile
        1           5                        10

AAT AAA GAT ATC GAG GAG TGC AAT GCC ATC ATT GAG CAG TTT ATC GAC              96
Asn Lys Asp Ile Glu Glu Cys Asn Ala Ile Ile Glu Gln Phe Ile Asp
 15              20                  25                      30

TAC CTG CGC ACC GGA CAG GAG ATG CCG ATG GAA ATG GCG GAT CAG GCG             144
Tyr Leu Arg Thr Gly Gln Glu Met Pro Met Glu Met Ala Asp Gln Ala
                 35              40                  45

ATT AAC GTG GTG CCG GGC ATG ACG CCG AAA ACC ATT CTT CAC GCC GGG             192
Ile Asn Val Val Pro Gly Met Thr Pro Lys Thr Ile Leu His Ala Gly
                 50              55                  60

CCG CCG ATC CAG CCT GAC TGG CTG AAA TCG AAT GGT TTT CAT GAA ATT             240
Pro Pro Ile Gln Pro Asp Trp Leu Lys Ser Asn Gly Phe His Glu Ile
             65              70                  75

GAA GCG GAT GTT AAC GAT ACC AGC CTC TTG CTG AGT GGA GAT GCC TCC             288
Glu Ala Asp Val Asn Asp Thr Ser Leu Leu Leu Ser Gly Asp Ala Ser
         80              85                  90

TAC CCT TAT GAT GTG CCA GAT TAT GCC TCT CCC GAA TTC GGCCGACTCG              337
Tyr Pro Tyr Asp Val Pro Asp Tyr Ala Ser Pro Glu Phe
 95              100             105

AGAAGCTT                                                                    345
```

( 2 ) INFORMATION FOR SEQ ID NO:74:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:74:

GGCGGCCGCG AATTCGAGAA CTTCCAAAAG GTGGAAAAG      39

( 2 ) INFORMATION FOR SEQ ID NO:75:

( i ) SEQUENCE CHARACTERISTICS:
( A ) LENGTH: 41 base pairs
( B ) TYPE: nucleic acid
( C ) STRANDEDNESS: single ( D ) TOPOLOGY: linear ( i i ) MOLECULE TYPE: other nucleic acid ( x i ) SEQUENCE DESCRIPTION: SEQ ID NO:75:

GCGGCCGCGG ATCCAGGCTA TCAGAGTCGA AGATGGGGTA C            41

( 2 ) INFORMATION FOR SEQ ID NO:76:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:76:

GCGGCCGCGA ATTCGAAGCT GGAGGAGCAA CCGGGAGC            38

( 2 ) INFORMATION FOR SEQ ID NO:77:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:77:

GCGGCCGCGG ATCCTCAATG GCGGAATCGC TGCAGCAC            38

( 2 ) INFORMATION FOR SEQ ID NO:78:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:78:

GCGGCGGCGT CGACCAGAAA TACGAGAAAC TGGAAAAG            38

( 2 ) INFORMATION FOR SEQ ID NO:79:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:79:

GCGGCGGCGT CGACCGGGGC CTAGGGCGGA CAGAAGTC            38

( 2 ) INFORMATION FOR SEQ ID NO:80:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:80:

GCGGCCGCGA ATTCGAGAAG GACGGCCTGT GCCGCGCT                      38

( 2 ) INFORMATION FOR SEQ ID NO:81:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:81:

GCGGCGGCCT CGAGGAGGCC TCAGGCTGTA TTCAGCTC                      38

( 2 ) INFORMATION FOR SEQ ID NO:82:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:82:

GGCCGGCCGG GATCCTTGTC GCTCCGCGGC TGCTCCGGCT G                  41

( 2 ) INFORMATION FOR SEQ ID NO:83:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:83:

GCGGCCGCGT CGACGTTTTA AGATTGGCTG TAGCTAGAG                     39

( 2 ) INFORMATION FOR SEQ ID NO:84:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:84:

GGCCGGCCGG AATTCGAACA CCAGCTCCTG TGCTGCGAAG                    40

( 2 ) INFORMATION FOR SEQ ID NO:85:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:85:

GCGGCCGCGT CGACGCGCCC TCAGATGTCC ACGTCCCGC                     39

( 2 ) INFORMATION FOR SEQ ID NO:86:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( i i ) MOLECULE TYPE: other nucleic acid ( x i ) SEQUENCE DESCRIPTION: SEQ ID NO:86:

GCGGCGGCGA ATTCGAGCTG CTGTGCCACG AGGTGGAC    38

( 2 ) INFORMATION FOR SEQ ID NO:87:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( i i ) MOLECULE TYPE: other nucleic acid ( x i ) SEQUENCE DESCRIPTION: SEQ ID NO:87:

GCGGCGGCGA ATTCGAGCTG CTGTGCCACG AGGTGGAC    38

( 2 ) INFORMATION FOR SEQ ID NO:88:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( i i ) MOLECULE TYPE: other nucleic acid ( x i ) SEQUENCE DESCRIPTION: SEQ ID NO:88:

GGCCGGCCGG AATTCAAGGA GGACGGCGGC GCGGAGTTC    39

( 2 ) INFORMATION FOR SEQ ID NO:89:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( i i ) MOLECULE TYPE: other nucleic acid ( x i ) SEQUENCE DESCRIPTION: SEQ ID NO:89:

GCGGCCGCGT CGACGGGTGG TCACGCCATT TCCGGCCCG    39

( 2 ) INFORMATION FOR SEQ ID NO:90:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: other nucleic acid ( x i ) SEQUENCE DESCRIPTION: SEQ ID NO:90:

GCGGCCGCGA ATTCAAGCCG CCCAGTTCAA TACAAACAAG    40

( 2 ) INFORMATION FOR SEQ ID NO:91:

( i ) SEQUENCE CHARACTERISTICS:
  ( A ) LENGTH: 40 base pairs
  ( B ) TYPE: nucleic acid
  ( C ) STRANDEDNESS: single -continued (D) TOPOLOGY: linear (ii) MOLECULE TYPE: other nucleic acid (xi) SEQUENCE DESCRIPTION: SEQ ID NO:91:

GCGGCCGCCT CGAGATTCCT TTATCTTGAT ACAGATCTTG 40

(2) INFORMATION FOR SEQ ID NO:92:

(i) SEQUENCE CHARACTERISTICS:
 (A) LENGTH: 40 base pairs
 (B) TYPE: nucleic acid
 (C) STRANDEDNESS: single
 (D) TOPOLOGY: linear (ii) MOLECULE TYPE: other nucleic acid (xi) SEQUENCE DESCRIPTION: SEQ ID NO:92:

GCGGCCGCGG ATCCAGCCGC CCAAAACCCC CCGAAAAACG 40

(2) INFORMATION FOR SEQ ID NO:93:

(i) SEQUENCE CHARACTERISTICS:
 (A) LENGTH: 44 base pairs
 (B) TYPE: nucleic acid
 (C) STRANDEDNESS: single
 (D) TOPOLOGY: linear (ii) MOLECULE TYPE: other nucleic acid (xi) SEQUENCE DESCRIPTION: SEQ ID NO:93:

GCGGCCGCGA ATTCCTCGAG CTCATTTCTC TTCCTTGTTT GAGG 44

(2) INFORMATION FOR SEQ ID NO:94:

(i) SEQUENCE CHARACTERISTICS:
 (A) LENGTH: 40 base pairs
 (B) TYPE: nucleic acid
 (C) STRANDEDNESS: single
 (D) TOPOLOGY: linear (ii) MOLECULE TYPE: other nucleic acid (xi) SEQUENCE DESCRIPTION: SEQ ID NO:94:

GCGGCCGCGG ATCCAAGCCC CTGCACCAGC AGCTCCTACA 40

(2) INFORMATION FOR SEQ ID NO:95:

(i) SEQUENCE CHARACTERISTICS:
 (A) LENGTH: 38 base pairs
 (B) TYPE: nucleic acid
 (C) STRANDEDNESS: single
 (D) TOPOLOGY: linear (ii) MOLECULE TYPE: other nucleic acid (xi) SEQUENCE DESCRIPTION: SEQ ID NO:95:

GCGGCCGCGT CGACTCAGTC TGAGTCAGGC CCTTCTGT 38

CDK4 BINDING ASSAY

BACKGROUND OF THE INVENTION

Passage of a mammalian cell through the cell cycle is regulated at a number of key control points. Among these are the points of entry into and exit from quiescence ($G_0$), the restriction point, the $G_1/S$ transition, and the $G_2/M$ transition (for review, see Draetta (1990) *Trends Biol Sci* 15:378–383; and Sherr (1993) *Cell* 73:1059–1065). For a cell to pass through a control point and enter the next phase of the cell cycle, it must complete all of the events of the preceding cell cycle phase and, in addition, satisfy a number of check-point controls. Such controls act, for example, to ensure that DNA replication has been successfully completed before the onset of mitosis. Ultimately, information from these check-point controls is integrated through the regulated activity of a group of related kinases, the cyclin-dependent kinases (CDKs). Once a phase of the cell cycle has been successfully completed, phosphorylation of a critical substrates by activated CDKs allow passage of a cell cycle transition point and execution of the next cell cycle phase.

The ordered activation of the different CDKs constitutes the basic machinery of the cell cycle. The activity of CDKs is controlled by several mechanisms that include stimulatory and inhibitory phosphorylation events, and complex formation with other proteins. To become active, CDKs require the association of a group of positive regulatory subunits known as cyclins (see, for example, Nigg (1993) *Trends Cell Biol.* 3:296). In particular, human CDK4 exclusively associates with the D-type cyclins (D1, D2, and D3) (Xiong et al. (1992) *Cell* 71:505; Xiong et al. (1993) *Genes and Development* 7:1572; and Matsushime et al. (1991) *Cell* 65:701) and, conversely, the predominant catalytic partner of the D-type cyclins is the CDK4 kinase (Xiong et al. (1992) *Cell*). The complexes formed by CDK4 and the D-type cyclins have been strongly implicated in the control of cell proliferation during the G1 phase (Motokura et al. (1993) *Biochem. Biophys. Acta.* 1155:63–78; Sherr (1993) *Cell* 73:1059–1065; Matsushimi et al. (1992) *Cell* 71:323–334); and Kamb et al. (1994) *Science* 264:436–440).

SUMMARY OF THE INVENTION

The present invention relates to the discovery of novel proteins of mammalian origin which can associate with the human cyclin dependent kinase 4 (CDK4). As described herein, a CDK4-dependent interaction trap assay was used to isolate a number of proteins which bind CDK4, and which are collectively referred to herein as "CDK4-binding proteins" or "CDK4-BPs". In particular embodiments of the present invention, human genes have been cloned for an apparent kinase (clone #225), an apparent isopeptidase (clone #269), an apparent protease (clone #71), a human cdc37 (clone #269), a selectin-like protein (clone #11). The present invention, therefore, makes available novel proteins (both recombinant and purified forms), recombinant genes, antibodies to the subject CDK4-binding proteins, and other novel reagents and assays for diagnostic and therapeutic use.

One aspect of the invention features a substantially pure preparation of a CDK4-binding protein, or a fragment thereof. In preferred embodiments: the protein comprises an amino acid sequence at least 70% homologous to the amino acid sequence represented by one of SEQ ID Nos. 25–48; the polypeptide comprises an amino acid sequence at least 80% homologous to the amino acid sequence represented by one of SEQ ID Nos. 25–48; the polypeptide comprises an amino acid sequence at least 90% homologous to the amino acid sequence of one of SEQ ID Nos. 25–48; the polypeptide comprises an amino acid sequence identical to the amino acid sequence of one of SEQ ID Nos. 25–48. In a preferred embodiment: the fragment comprises at least 5 contiguous amino acid residues of one of SEQ ID Nos. 25–48; the fragment comprises at least 20 contiguous amino acid residues of one of SEQ ID Nos. 25–48; the fragment comprises at least 50 contiguous amino acid residues of one of SEQ ID Nos. 25–48. In a preferred embodiment, the fragment comprises at least a portion of the CDK4-BP which binds to a CDK, e.g. CDK4, e.g. CDK6, e.g. CDK5.

Yet another aspect of the present invention concerns an immunogen comprising the CDK4-binding protein, or a fragment thereof, in an immunogenic preparation, the immunogen being capable of eliciting an immune response specific for the subject CDK4-BP; e.g. a humoral response, e.g. an antibody response; e.g. a cellular response.

A still further aspect of the present invention features an antibody preparation specifically reactive with an epitope of the CDK4-BP immunogen.

Another aspect of the present invention features a recombinant CDK4-binding protein, or a fragment thereof, comprising an amino acid sequence which is preferably: at least 70% homologous to one of SEQ ID Nos. 25–48; at least 80% homologous to one of SEQ ID No. 25–48; at least 90% homologous to one of SEQ ID No. 25–48. In a preferred embodiment, the recombinant CDK4-BP functions in one of either role of an agonist of cell cycle regulation or an antagonist of cell cycle regulation.

In one embodiment, the subject CDK4-BP is a protease. In preferred embodiments: the protease mediates degradation of cellular proteins, e.g. cell-cycle regulatory proteins, e.g. CDK4-associated proteins, e.g. cyclins, e.g. D-type cyclins; the protease affects the cellular half-life of a cell-cycle regulatory protein, e.g. a CDK-associated protein, e.g. a cyclin, e.g. a D-type cyclin, e.g. in normal cells, e.g. in cancerous cells.

In another embodiment, the subject CDK4-BP is a kinase, e.g. a CDK-activating kinase, e.g. a MAP kinase.

In another embodiment, the subject CDK4-BP is a Tre oncoprotein, e.g. an isopeptidase, e.g. a deubiquitinating enzyme.

In yet another embodiment, the CDK4-binding protein is a human homolog of the yeast cdc37 gene., e.g. a protein which functions to control cell-cycle progression by integrating extracellular stimulus into cell-cycle control, e.g. which binds Rb, e.g. which binds p53.

In a still further embodiment, the CDK4-binding protein is an adhesion molecule, e.g. related to a selectin, e.g. which is responsible for integrating information from surrounding cell-cell contacts into a checkpoint control.

In yet other preferred embodiments, the recombinant CDK4-binding protein is a fusion protein further comprising a second polypeptide portion having an amino acid sequence from a protein unrelated the CDK4-binding protein. Such fusion proteins can be functional in an interaction trap assay.

Another aspect of the present invention provides a substantially pure nucleic acid comprising a nucleotide sequence which encodes a CDK4-binding protein, or a fragment thereof, including an amino acid sequence at least 70% homologous to one of SEQ ID Nos. 25–48. In a more preferred embodiment, the nucleic acid encodes a protein comprising an amino acid sequence at least 70% homologous to one of SEQ ID Nos. 25–28; and more preferably at least 80% homologous to one of SEQ ID No. 25–28.

In yet a further preferred embodiment, the nucleic acid which encodes a CDK4-binding protein of the present invention, or a fragment thereof, hybridizes under stringent conditions to a nucleic acid probe corresponding to at least 12 consecutive nucleotides of SEQ ID Nos. 1-24 and 49-66; more preferably to at least 20 consecutive nucleotides of said SEQ ID listings; more preferably to at least 40 consecutive nucleotides of said SEQ ID listings. In a preferred embodiment, the nucleic acid which encodes a CDK4-binding protein of the present invention is provided by ATCC deposit No. 75788.

Furthermore, in certain preferred embodiments, nucleic acids encoding one of the subject CDK4-binding protein may comprise a transcriptional regulatory sequence, e.g. at least one of a transcriptional promoter or transcriptional enhancer sequence, operably linked to the CDK4-BP gene sequence so as to render the gene sequence suitable for use as an expression vector. In one embodiment, the CDK4-BP gene is provided as a sense construct. In another embodiment, the CDK4-BP gene is provided as an antisense construct.

The present invention also features transgenic non-human animals, e.g. mice, rabbits and pigs, which either express a heterologous CDK4-BP gene, e.g. derived from humans, or which mis-express their own homolog of a CDK4-BP gene, e.g. expression of the mouse homolog of the clone #71 protease is disrupted, e.g. expression of the mouse homolog of the clone #116 isopeptidase is disrupted, e.g. expression of the mouse homolog of the clone #225 kinase is disrupted, e.g. expression of the mouse homolog of the clone #269 cdc37 is disrupted. Such a transgenic animal can serve as an animal model for studying cellular disorders comprising mutated or mis-expressed CDK4-BP genes.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of one of SEQ ID Nos. 1-24 and 49-66, or naturally occurring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a CDK4-BP nucleic acid in a sample of cells isolated from a patient; e.g. measuring a CDK4-BP mRNA level in a cell; e.g. determining whether a genomic CDK4-BP gene has been mutated or deleted.

Another aspect of the present invention provides a method of determining if a subject, e.g. a human patient, is at risk for a disorder characterized by unwanted cell proliferation, comprising detecting, in a tissue of the subject, the presence or absence of a genetic lesion characterized by at least one of (i) a mutation of a gene encoding a CDK4-binding protein, or a homolog thereof; or (ii) the mis-expression of the CDK4-BP gene. In preferred embodiments: detecting the genetic lesion comprises ascertaining the existence of at least one of a deletion of one or more nucleotides from the gene, an addition of one or more nucleotides to the gene, an substitution of one or more nucleotides of the gene, a gross chromosomal rearrangement of the gene, a gross alteration in the level of a messenger RNA transcript of the gene, the presence of a non-wild type splicing pattern of a messenger RNA transcript of the gene, or a non-wild type level of the protein. For example, detecting the genetic lesion can comprise (i) providing a probe/primer comprising an oligonucleotide containing a region of nucleotide sequence which hybridizes to a sense or antisense sequence of one of SEQ ID Nos. 1-24 and 49-66, or naturally occurring mutants thereof, or 5' or 3' flanking sequences naturally associated with the gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the CDK4-BP gene and, optionally, of the flanking nucleic acid sequences; e.g. wherein detecting the lesion comprises utilizing the probe/primer in a polymerase chain reaction (PCR); e.g. wherein detecting the lesion comprises utilizing the probe/primer in a ligation chain reaction (LCR). In alternate embodiments, the level of the protein is detected in an immunoassay.

Other features and advantages of the invention will be apparent from the following detailed description, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., New York); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

BRIEF DESCRIPTION OF THE FIGURES

FIG. 2 is a table of demonstrating the interaction of each of the CDK-binding proteins with other cell cycle proteins.

DETAILED DESCRIPTION OF THE INVENTION

Figure 1:
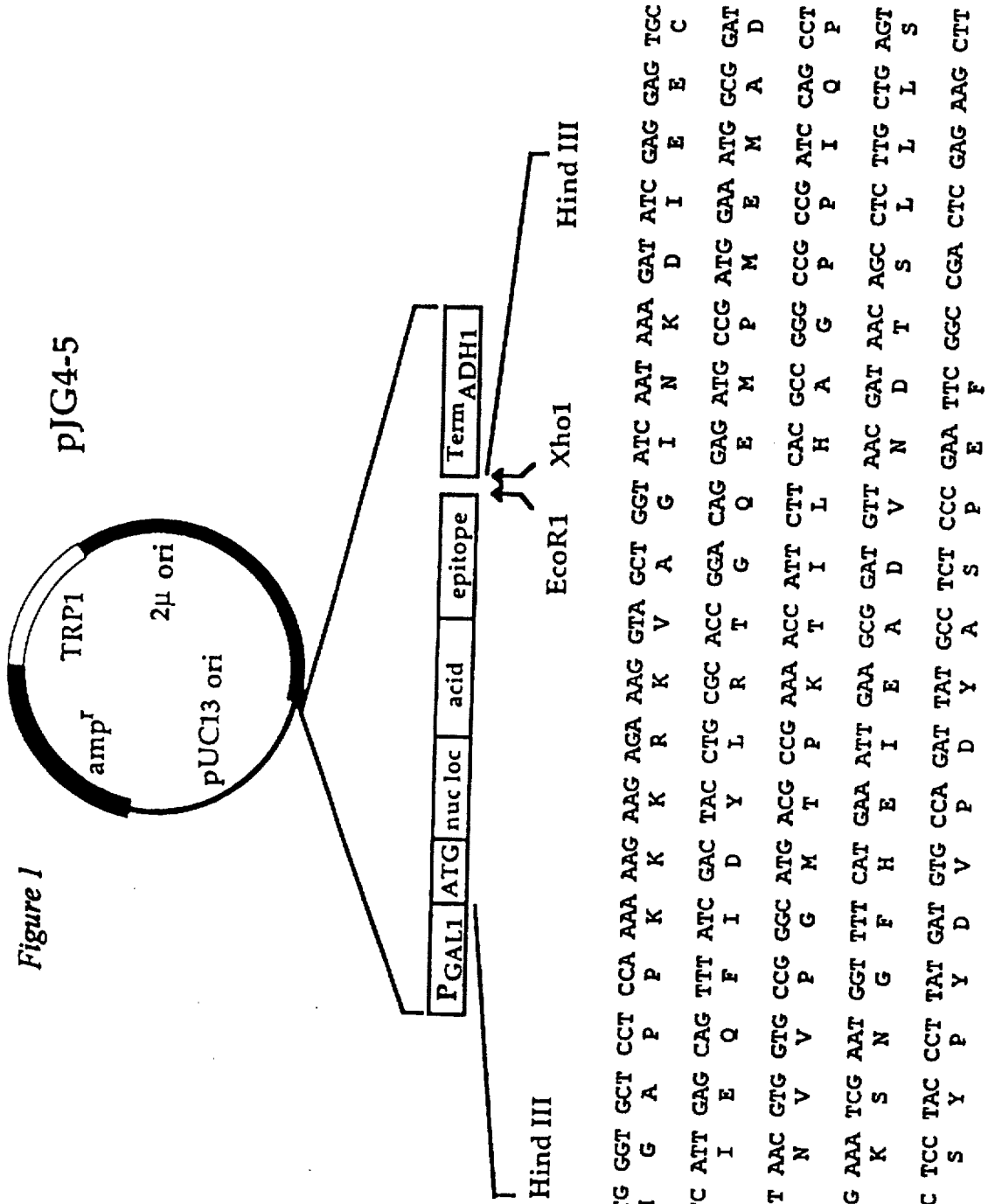
FIG. 1 illustrates the pJG4-5 library plasmid and the invariant 107 amino acid moiety (SEQ ID No. 73) it encodes. This moiety carries (amino to carboxy termini) an ATG, an SV40 nuclear localization sequence (PPKKKRKVA), the B42 transcription activation domain, and the HA1 epitope tag (YPYDVPDYA). pJG4-5 directs the synthesis of proteins under the control of the GAL1 promoter. It carries a 2μ replicator and a TRP1⁺ selectable marker. Each of the CDK4 binding proteins of ATCC deposit accession No. 75788 are inserted as EcoRI-XhoI fragments. Downstream of the XhoI site, pJG4-5 contains the ADH1 transcription terminator.

The division cycle of eukaryotic cells is regulated by a family of protein kinases known as the cyclin-dependent kinases (CDKs). The sequential activation of individual members of this family and their consequent phosphorylation of critical substrates promotes orderly progression through the cell cycle. The complexes formed by the cyclin-dependent kinase 4 (CDK4) and the D-type cyclins have been strongly implicated in the control of cell proliferation during the G1 phase, and are strong candidates for oncogenes that could be major factors in tumorigenesis. In fact, recent evidence suggests the possibility that CDK4 may serve as a general activator of cell division in most, if not all, cells. The present invention, as set out below, derives from the discovery that, in addition to cyclins, p21, p16, and PCNA, the cyclin dependent kinase 4 is also associated with several other cellular proteins (hereinafter termed "CDK4-binding proteins" or "CDK4-BPs"), which association is presumably important to the regulation of cell growth, cell proliferation, and/or cell differentiation.

As described herein, a CDK4-dependent interaction trap assay was used to identify proteins that can associate with human CDK4. Surprisingly, a number of novel proteins which interact with CDK4 were cloned from a $G_0$ fibroblast cDNA library. Given the central role of CDK4 early in $G_1$ phase, the present data suggest that CDK4 is an important multiplex receiver of signal transduction data, with multiple pathways converging on it to control various aspects of the kinases's activity, including both catalytic activity and substrate specificity. Thus, because each of the proteins identified herein act close to the point of CDK4 process control, such as by channeling converging upstream signals to CDK4 or demultiplexing the activation of the CDK4 kinase activity by directing divergent downstream signal propagation from CDK4, each of the subject proteins is a potential therapeutic target for agents capable of modulating cell proliferation and/or differentiation. The present invention, therefore, makes available novel assays and reagents for therapeutic and diagnostic uses. Moreover, drug discovery assays are provided for identifying agents which can affect the binding of one of the subject CDK-binding proteins with another cell-cycle regulatory protein, or which inhibit an enzymatic activity of the subject CDK-BP. Such agents can be useful therapeutically to alter the growth and/or differentiation a cell.

For example, in one embodiment of the present invention, the CDK4-binding protein is a protease involved in degradation of cell-cycle regulatory proteins, e.g. a G1-cyclins, e.g. cyclin D1, D2 or D3. For instance, the clone designated #71 (Table 2 and FIG. 2), corresponding to the partially characterized protein represented by SEQ ID No. 31 (encoded by the nucleic acid of SEQ ID No. 7), shares certain homology with ATP-dependent proteases and is strongly suspected of possessing proteolytic activity and being involved in regulating the cellular levels of other CDK4- or CDK6-associated proteins. For instance, the subject protease could be recruited by its interaction with CDK4 or CDK6 to a CDK4/cyclin D or CDK6/cyclin D complex in order to cause degradation of a D-type cyclin (e.g. cyclin D1). Such degradation would release the CDK for subsequent binding to another $G_1$ cyclin. Thus, agents which disrupt the binding of the protease to CDK4 or CDK6 can be used to prevent the proteolytic destruction of certain CDK4 or CDK6 associated cyclins, e.g. effectively increases the half-life of such cyclins. Alternatively, the present invention, by providing purified and/or recombinant forms of the protease, also facilitates identification of agents which act as mechanistic inhibitors of the protease and inhibit its proteolytic action on its substrates irrespective of its ability to bind CDK. As described in U.S. patent application Ser. No. 08/227,850 entitled "D1 Cyclin in $G_1$ Progression of Cell Growth, and Uses Related Thereto", the ability to increase the cellular level of cyclin D1, such as by inhibiting its proteolysis, can be useful in preventing unwanted cell growth in certain proliferative disorders.

In another embodiment, the CDK4-binding protein is an isopeptidase, such as a deubiquitinating enzyme. For instance, the clone designated #116 (Table 2 and FIG. 2), corresponding to the partially characterized protein represented by SEQ ID. No. 33 (encoded by the nucleic acid of SEQ ID No. 9) shares certain homology with previously described Tre oncogenes and isopeptidases, and is likely to function as a de-ubiquitinating enzyme. As is generally understood, the activities of several cellular proteins are reversibly regulated by ubiquitination and a successive de-ubiquitination steps such that the half-life of the protein, or allosteric control of its biological function, is fine tuned by the control of the level of ubiquitination of that protein. For example, as described above, cyclin degradation by ubiquitin-mediated proteolysis is an important step in the progression of the cell cycle. Thus, the subject de-ubiquitinating enzyme may be involved in balancing the level of ubiquitinated cyclin D by antagonistically competing with ubiquitin conjugating enzymes. Thus, CDK4 may be used by the subject enzyme to provide proximity to a substrate such as cyclin D. Moreover, CDK4 may provide additional substrate proximity with other cell cycle regulatory proteins, such as those involved in regulation of Rb function. Agents which inhibit either the interaction of the de-ubquitinating enzyme with CDK4, or which mechanistically inhibit the enzyme, can be used to disrupt the balance of ubiquitination of certain regulatory proteins.

In yet another embodiment, the CDK4-binding protein is a kinase which acts on CDK4 or other proteins which bind CDK4. For instance, the clone designated #225, corresponding to the partially characterized protein represented by SEQ ID No. 43 (C-terminus) and No. 48 (N-terminus) (encoded by SEQ ID No. 19 and 24, respectively) shares certain homology with other kinases and is suspected of being a CDK-activating kinase (CAK) which is able to phosphorylate CDK4 on a threonine or serine residue required for activation of the CDK4 kinase activity (e.g. Thr-172). To date, CAK-like activities have only been positively identified as activities in G2 phase. Thus, the subject CAK may represent a novel G1 phase CAK. It is also possible that the kinase activity of the clone #225 functions in a manner similar to a MAP kinase. This model is consistent with CDK4 being an apparent receiver of extracellular mitogenic signals, and MAP kinases being involved in the intracellular transduction pathways for those signals. Agents which prevent the subject kinase from interacting with CDK4, or which mechanistically inhibit the kinase activity, can be useful in the inhibition of CDK4 activation and/or mitogenic stimulation, and therefore function as anti-proliferative agents. Such agents may be particularly useful in down-regulating responsive of a tumor cell to growth factors and cytokines, e.g. inhibit paracrine auto-feedback loops.

In still further embodiments, the CDK4-binding protein is a human homolog of the yeast cdc37 gene (Ferguson et al. (1988) *Nuc. Acid Res.* 14:6681–6697; and Breter et al. (1983) *Mol. Cell Biol.* 3:881–891). To illustrate, the clone #269 (Table 2 and FIG. 2), corresponding to the partially characterized protein represented by SEQ. ID No. 46, and encoded by the pJ64-5-ΓDKBP clone having an EcoRI-XhoI fragment characterized by SEQ. ID No. 23 (5' end) and No. 64 (3' end), shares certain homology with the *S. cerevisiae* cdc37 gene. Mutation or deletion in yeast of the cdc37 gene results in arrest at "START", the regulatory point in the yeast cell-cycle which in many ways resembles the $G_1$ restriction point and $G_1/S$ checkpoint in mammalian cells. Thus, it is presumed that the human cdc37 functions to control cell-cycle progression, perhaps by integrating extracellular stimulus into cell-cycle control, and it is therefore expected that the CDK4-cdc37 interaction can be a very important target for drug design. For instance, agents which disrupt the binding of CDK4 and cdc37, e.g., CDK4 peptidomimetic which bind cdc37, could be used to effect the progression of cell through $G_1$. Moreover, antagonistic mutants of the subject cdc37, e.g., mutants which disrupt the function of normal cdc37, can be provided by gene therapy in order to inhibit proliferation of cells. The fact that the human cdc37 homolog binds both Rb and p53 (FIG. 2), supports the role of cdc37 in cell-cycle checkpoints, as well as suggest alternate therapeutic targets (e.g., the Rb-cdc37 or p53-cdc37 interactions).

In still further embodiments, the CDK4-binding protein is related to an adhesion molecule, such as a selectin. For example, the pJG4-5-CDKBP clone #11, corresponding to the partially characterized protein represented by SEQ. ID No. 25 (encoded by SEQ. ID No. 1) shares approximately 50% homology with selectin proteins, adhesion molecules which are found on epitheleal and possibly lymphoid cells. Growth of normal diploid mammalian cells in vitro, and presumably in vivo, is strongly regulated by the actual cell density. Cell-cell contacts via specific plasma membrane glycoproteins has been found to be a main growth regulatory principle. Malignant growth is suggested to result from impaired function of the signal transduction pathways connected with these membrane proteins. Moreover, it has been previously noted that a major control point in fibroblast cell cycle exists at the $G_0$–$G_1$ transition and is regulated by extracellular signals including contact inhibition (Han et al. (1993) *J. Cell Biol.* 122:461–471). It is asserted here that the subject adhesion molecule is responsible for integrating information from surrounding cell contacts into a checkpoint control. Consistent with this notion, nucleic acid hybridization experiments using a probe based on SEQ. ID No. 1 have detected clone 11 mRNA in normal primary fibroblasts (e.g., WI38 and IMR90), but that clone 11 mRNA levels become undetectable in SV40 Laze T transformed fibroblasts as well as fibrocarzinom or cell lines (e.g., Hs 913T cells)—each of which have lost contact inhibition and are able to form foci. Thus, the interaction of selectin-related proteins, such as clone 11, with CDKs (e.g., CDK4, CDK5 or CDK6) is a potential therapeutic target for design of agents capable of modulating proliferation and/or differentiation. In some instances, agents which restore the function of such selectin-like proteins will be desirable to inhibit proliferation. For example, peptidomimetics based on clone 11 sequences which bind CDK4, or gene therapy vehicles which deliver the clone 11 gene, can be used to mimic the function of the wild type protein and slow progression of the cell through the $G_1$ phase. For instance, in addition to treatment of cancer, such agents may be used to treat hypertension, diabetic macroangiopathy or artherosclerosis, where numerous abnormalities in vascular smooth-muscle cell (vsmc) growth is a common pathology resulting from abnormal contact inhibition and accelerated entry into the S phase.

Conversely, agents which bind clone #11 and/or other related selectins and prevent binding to a CDK can be used to prevent contact inhibition and therefore enhance proliferation (and potentially inhibit differentiation). For instance, such agents can be used to relieve contact inhibition of chondrocytes, particularly fibrochondrocytes, in order to facilitate de-differentiation of these cells into chondroblast cells which produce cartilage. Thus, therapeutic agents can be identified in assays using the subject protein which are useful in the treatment of connective tissue disorders, including cartilage repair.

In still further embodiments, the CDK4-binding protein is a DNA binding factor involved in regulation of transcription and/or replication. For example, clones 127 and 118 (see Table 2 and FIG. 2) each appear to possess zinc-finger motifs which implicate them in DNA-binding. These proteins may function as downstream targets for activation or inactivation by CDK4 phosphorylation, and/or to localize CDK4 to DNA. Moreover, the fact that clone 127 binds strongly to p53 and Rb (FIG. 2) suggests an integrated role in the $G_1$ checkpoint(s).

In another embodiment, the CDK4-binding protein contains a CDK concensus phosphorylation signal, and the CDK4-BP is a CDK4 substrate and/or an inhibitor of the CDK4 kinase activity. For example, each of clones #13, #22 and #227 contain such CDK concensus sequence. Thus, these cellular proteins can be downstream substrates of CDK4 (as well as CDK6 or CDK5). Additionally, the CDK4-BP, particularly the phosphoprotein form, can serve as an inhibitor of a CDK, such as CDK4. Thus, the phosphorylated CDK4-BP could serve as a feedback loop, either from CDK4 itself or from another CDK, acting to modulate the activity of a CDK to which it binds.

Furthermore, it is demonstrated here for the first time that p16 is able to associate with CDK6. Previously, p16 was believed to associate exclusively with CDK4 and acted as an inhibitor of the CDK4 kinase activity. The present data strongly suggests that p16 functions in the same or similar role with respect to CDK6. Thus, the interaction between p16 and CDK6 is a potential therapeutic target for agents which (i) disrupt this interaction; (ii) mimic this interaciton by binding CDK6 in a manner analogous to p16, e.g. p16 peptidomimetics which bind CDK6; or (iii) are mechanistic inhibitors of the CDK6 kinase activity. Moreover, as described below, the present invention provides differential screening assays for identifying agents which disrupt or otherwise alter the regulation of only one of either CDK4 or CDK6 without substantially affecting the other.

Polypeptides referred to herein as having an activity of a CDK4-BP protein are defined as peptides that have an amino acid sequence corresponding to all or a portion of the amino acid sequence of a subject CDK4-BP protein shown in SEQ ID NOS: 25–48 and which have at least one biological activity of a CDK4-BP protein. In preferred embodiments, a biological activity of a CDK4-BP protein can include, in addition to those activities described above for individual clones: an ability to regulate a eukaryotic cell cycle, e.g. a mammalian cell cycle, e.g., a human cell cycle; an ability to regulate proliferation/cell growth of a eukaryotic cell, e.g. a mammalian cell, e.g., a human cell; an ability to regulate progression of a eukaryotic cell through G1 phase, e.g. regulate progression of a mammalian cell from $G_0$ phase into $G_1$ phase, e.g. regulate progression of a mammalian cell through $G_1$ phase; an ability to regulate the kinase activity of a cyclin dependent kinase (cdk), e.g. a cdk active in G1 phase, e.g. CDK4, e.g. CDK6, e.g. an ability to regulate phosphorylation of an Rb or Rb-related protein by CDK4; an ability to regulate the effects of mitogenic stimulation on cell-cycle progression, e.g. regulate contact inhibition, e.g. mediate growth factor- or cytokine-induced mitogenic stimulation, e.g. regulate paracrine-responsiveness. Certain of the CDK4-binding proteins of the present invention may also have biological activities which include an ability to suppress tumor cell growth, e.g. in a tumor cell which has lost contact inhibition, e.g. in tumor cells which have paracrine feedback loops. Other biological activities of the subject CDK4-binding proteins are described herein or will be reasonably apparent to those skilled in the art.

Accordingly, one aspect of this invention pertains to an isolated nucleic acid comprising a nucleotide sequence encoding one of the subject CDK4-BP proteins, fragments thereof, and/or equivalents of such nucleic acids. The term nucleic acid as used herein is intended to include such fragments and equivalents. The term equivalent is understood to include nucleotide sequences encoding functionally equivalent CDK4-binding proteins or functionally equivalent peptides which, for example, retain the ability to bind a CDK (e.g. CDK4), and which may additionally reatin other activities of a CDK4-binding protein such as described herein. Equivalent nucleotide sequences will include sequences that differ by one or more nucleotide substitutions, additions or deletions, such as allelic variants; and will also include sequences that differ from the nucleotide sequence encoding the presently claimed CDK4-binding proteins shown in any of SEQ ID Nos: 1–24 or 49–70 due to the degeneracy of the genetic code. Equivalents will also include nucleotide sequences that hybridize under stringent conditions (i.e., equivalent to about 20°–27° C. below the melting temperature ($T_m$) of the DNA duplex formed in about 1M salt) to the nucleotide sequence of a CDK4-binding protein represented by one of SEQ ID Nos: 25–48, or to a nucleotide sequence of a CDK4-BP insert of pJG4-5-CDKBP (ATCC deposit no. 75788). In one embodiment, equivalents will further include nucleic acid sequences derived from, and evolutionarily related to, a nucleotide sequences shown in any of SEQ ID Nos: 1–24.

Moreover, it will be generally appreciated that, under certain circumstances, it may be advantageous to provide homologs of the subject CDK4-binding proteins which function in a limited capacity as one of either a CDK4-BP agonists or a CDK4-BP antagonists, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all CDK4-BP related biological activities. Such homologs of the subject CDK4-binding proteins can be generated by mutagenesis, such as by discrete point mutation(s) or by truncation. For instance, mutation can give rise to homologs which retain the substantially same, or merely a subset, of the biological activity of the CDK4-BP from which it was derived. Alternatively, antagonistic forms of the protein can be generated which are able to inhibit the function of the naturally occurring form of the protein. For example, homologs can be made which, relative the authentic form of the protein, competitively bind to CDK4 or other upstream or downstream binding partners of the naturally occurring CDK4-BP, but which are not themselves capable of forming productive complexes for propagating an intracellular signal or the like. When expressed in the same cell as the wild-type protein, such antagonistic mutants could be, for example, analogous to a dominant negative mutation arising in the cell. To illustrate, the homologs of the clone #71 protease might be generated to retain a protease activity, or, conversely, engineered to lack a protease activity, yet retain the ability to bind CDK4. In the instance of the latter, the catalytically inactive protease can be used to competitively inhibit the binding to CDK4 of the naturally-occurring form of the protease. In similar fashion, clone #225 homologs can be provided which, for example, are catalytically inactive as kinases, yet which still bind to a CDK. Such homolog are likely to act antagonistically to the role of the natural enzyme in cell cycle regulation, and can be used, for example, to inhibit paracrine feedback loops. Likewise, clone #116 homologs can be generated which are not capable of mediating ubiquitin levels, yet which nevertheless competively bind CDK4 and therefore act antagonistically to the wild-type form of the isopeptidase when expressed in the same cell.

As used herein, the term "gene" or "recombinant gene" refers to a nucleic acid comprising an open reading frame encoding a CDK4-binding protein of the present invention, including both exon and (optionally) intron sequences. A "recombinant gene" refers to nucleic acid encoding a CDK4-binding protein and comprising CDK4-Bp encoding exon sequences, though it may optionally include intron sequences which are either derived from a chromosomal CDK4-BP gene or from an unrelated chromosomal gene. Exemplary recombinant genes encoding the subject CDK4-binding proteins are represented by any one of SEQ ID Nos: 1–24. Moreover, recombinant genes encoding each of the subject CDK4-binding proteins can be isolated from ATCC deposit no. 75788, as described below. The term "intron" refers to a DNA sequence present in a given CDK4-BP gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of the CDK4-binding protein of the present invention or where anti-sense expression occurs from the transferred gene, the expression of a naturally-occurring form of the CDK4-binding protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant CDK4-BP gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the CDK4-binding protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a lymphoid lineage, e.g. B or T lymphocytes. In the illustrative embodiment of lymphoid-specific promoters, gene constructs can be used as a part of gene therapy to modulate levels of one of the subject CDK4-binding proteins in lymphoproliferative disorders, e.g. lymphomas, by directing expression of a recombinant form of one of the subject CDK4-binding proteins (e.g. agonist or antagonist) in only lymphatic tissue. The term also covers so-called "leaky" promoters, which regulate expression of a selected DNA primarily in one tissue, but cause expression in other tissues as well.

As used herein, a "transgenic animal" is any animal, preferably a non-human mammal, e.g. a rat, a mouse or pig, in which one or more of the cells of the animal includes a transgene. The transgene is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the transgenic animals described herein, the transgene causes cells to express a recombinant form of one or more of the subject CDK4-binding proteins, or alternatively, to disrupt expression of one or more of the naturally-occurring forms of the CDK4-BP genes.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a CDK4-binding protein" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject CDK4-binding proteins with a second amino acid sequence defining a domain foreign to and not substantially homologous with any domain of the subject CDK4-BP. A chimeric protein may present a foreign domain which is found (albeit in a different protein) in an organism which also expresses the first protein, or it may be an "interspecies", "intergeneric", etc. fusion of protein structures expressed by different kinds of organisms.

The term "evolutionarily related to", with respect to nucleic acid sequences encoding CDK4-binding proteins, refers to nucleic acid sequences which have arisen naturally in an organism, including naturally occurring mutants. The term also refers to nucleic acid sequences which, while derived from (e.g. isolated from) a naturally occurring CDK4-BP, have been altered by mutagenesis, as for example, combinatorial mutagenesis described below, yet still encode polypeptides which have at least one activity of a subject CDK4-binding protein, or which are antagonists of that proteins activities.

In one embodiment, the nucleic acid is a cDNA encoding a peptide having at least one activity of a subject CDK4-binding protein. Preferably, the nucleic acid is a cDNA molecule comprising at least a portion of the nucleotide sequence represented in any of SEQ ID NOS: 1-24. A preferred portion of the cDNA molecule includes the coding region of the molecule represented in any of SEQ ID NOS: 1-24.

Preferred nucleic acids encode a peptide having a CDK4-binding protein activity and being at least 60% homologous, more preferably 70% homologous and most preferably 80% homologous with an amino acid sequence shown in any of SEQ ID NOS: 25-48. Nucleic acids which encode peptides having an activity of a subject CDK4-binding protein and having at least about 90%, more preferably at least about 95%, and most preferably at least about 98-99% homology with a sequence shown in any of SEQ ID NOS: 25-48 are also within the scope of the invention. Homology refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. The degree of homology between sequences is a function of the number of matching or homologous positions shared by the sequences.

The nucleotide sequences shown in SEQ ID Nos. 1-24 and 49-70 encode portions of the subject CDK4-binding proteins. Therefore, in a further embodiment of the invention, the recombinant CDK4-BP genes can further include, in addition to nucleotides encoding the amino acid sequence shown in SEQ ID Nos. 25-48, additional nucleotide sequences which encode amino acids at the C-terminus and N-terminus of each protein, though not shown in those SEQ ID Nos. For instance, a recombinant CDK4-BP gene can include nucleotide sequences of a PCR fragment generated by amplifying the one of the coding sequence of one of the CDK4-BP clones of pJG4-5-CDKBP using sets of primers derived from Table 1.

Another aspect of the invention provides a nucleic acid which hybridizes under high or low stringency conditions to a nucleic acid which encodes a peptide having all or a portion of an amino acid sequence shown in any of SEQ ID NOS: 25-48. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, New York (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids encoding peptides, as described herein, and having a sequence which differs from the nucleotide sequence shown any of SEQ ID NOS: 1–24 due to degeneracy in the genetic code are also within the scope of the invention. Such nucleic acids encode functionally equivalent peptides (i.e., a peptide having a biological activity of a CDK4-binding protein) but differ in sequence at the nucleic acid level from the sequence shown in said sequence listings due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of the CDK4-binding protein. However, it is expected that DNA sequence polymorphisms that do lead to changes in the amino acid sequences of the subject CDK4-binding proteins will exist among vertebrates. One skilled in the art will appreciate that these variations in one or more nucleotides (up to about 3–5% of the nucleotides) of the nucleic acids encoding polypeptides having an activity of a CDK4-binding protein may exist among individuals of a given species due to natural allelic variation. Any and all such nucleotide variations and resulting amino acid polymorphisms are within the scope of this invention.

Fragments of the nucleic acids encoding the active portion of the presently claimed CDK4-binding proteins are also within the scope of the invention. As used herein, a fragment of the nucleic acid encoding the active portion of a CDK4-binding protein refers to a nucleic acid having fewer nucleotides than the nucleotide sequence encoding the entire amino acid sequence of a CDK4-binding protein but which nevertheless encodes a peptide having an agonist activity of a CDK4-binding protein (i.e., a peptide having at least one biological activity of a CDK4-binding protein) or alternatively, which is an antagonist of at least one biological activity of a CDK4-BP of the present invention. Nucleic acid fragments within the scope of the present invention include those capable of hybridizing under high or low stringency conditions with nucleic acids from other species for use in screening protocols to detect CDK4-BP homologs, as well as those capable of hybridizing with nucleic acids from human specimens for use in detecting the presence of a nucleic acid encoding one of the subject CDK4-BPs, including alternate isoforms, e.g. mRNA splicing variants. Nucleic acids within the scope of the invention may also contain linker sequences, modified restriction endonuclease sites and other sequences useful for molecular cloning, expression or purification of recombinant forms of the subject CDK4-binding proteins.

As indicated by the examples set out below, a nucleic acid encoding a peptide having an activity of one of the subject CDK4-binding protein may be obtained from mRNA present in any of a number of eukaryotic cells. It should also be possible to obtain nucleic acids encoding the subject CDK4-binding proteins from genomic DNA obtained from both adults and embryos. For example, a gene encoding a subject CDK4-binding protein can be cloned from either a cDNA or a genomic library in accordance with protocols herein described, as well as those generally known to persons skilled in the art. A cDNA encoding one of the subject CDK4-binding proteins can be obtained by isolating total mRNA from a cell, e.g. a mammalian cell, e.g. a human cell, including tumor cells. Double stranded cDNAs can then be prepared from the total mRNA, and subsequently inserted into a suitable plasmid or bacteriophage vector using any one of a number of known techniques. A gene encoding a subject CDK4-binding protein can also be cloned using established polymerase chain reaction techniques in accordance with the nucleotide sequence information provided by the invention. The nucleic acid of the invention can be DNA or RNA. A preferred nucleic acid is: e.g. a cDNA comprising a nucleic acid sequence represented by any one of SEQ ID Nos: 1–24 and 49–70; e.g. a cDNA derived from the pjG4-5-CDKBP library of ATCC deposit no. 75788.

This invention also provides expression vectors containing a nucleic acid encoding a peptide having an activity of one of the subject CDK4-binding proteins, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the CDK4-binding protein in either a constitutive or inducible manner, as well as, if desired, in a tissue-specific or cell-type specific manner. Accordingly, the term transcriptional regulatory sequence includes promoters, enhancers and other expression control elements. Such regulatory sequences are described in, for example, Goeddel; *Gene Expression Technology: Methods in Enzymology* 185, Academic Press, San Diego, Calif. (1990). It should be understood that the design of the expression vector may depend on such factors as the choice of the host cell to be transformed and/or the type of protein desired to be expressed. In one embodiment, the expression vector includes a recombinant gene encoding a peptide having an activity of a subject CDK4-binding protein, or alternatively, encoding a peptide which is an antagonistic-form of the subject CDK4-binding protein. Such expression vectors can be used to transfect cells and thereby produce proteins or peptides, including fusion proteins or peptides, encoded by nucleic acids as described herein.

Moreover, such vectors can be used as a part of a gene therapy protocol to reconstitute the function of, or alternatively, abrogate the function of one of the subject CDK4-binding proteins in a cell. Illustrative examples of therapeutic vehicles useful for delivery of a CDK4-BP construct to a target cell are disclosed in, for example, PCT publication WO 93/04701, PCT publication WO 92/22635, PCT publication WO 92/20316, PCT publication WO 92/19749, and PCT publication WO 92/06180.

Another aspect of the present invention concerns recombinant forms of the subject CDK4-binding proteins which are encoded by genes derived from eukaryotic organisms, e.g. mammals, e.g. humans, and which have at least one biological activity of a subject CDK4-binding protein, or alternatively, which is an antagonist of at least one biological activity of a CDK4-BP of the present invention, including naturally occurring dysfunctional mutants. The term "recombinant protein" refers to a protein of the present invention which is produced by recombinant DNA techniques, wherein generally DNA encoding the subject CDK4-binding protein is inserted into a suitable expression vector which is in turn used to transform a host cell to produce the heterologous protein. Moreover, the phrase "derived from", with respect to a recombinant gene encoding the recombinant CDK4-BP, is meant to include within the meaning of "recombinant protein" those proteins having an amino acid sequence of a native CDK4-binding protein of the present invention, or an amino acid sequence similar thereto, which is generated by mutations including substitutions and deletions (including truncation) of a naturally occurring CDK4-binding protein of an organism. Recombinant proteins preferred by the present invention, in addition to CDK4-binding proteins, are at least 60% homologous, more preferably 70% homologous and most preferably 80% homologous with an amino acid sequence shown in any of SEQ ID NOS: 25–48. Polypeptides having an activity of, or which are antagonistic to, the subject CDK4-binding proteins and having at least about 90%, more preferably at least about 95%, and most preferably at least about 98–99% homology with a sequence of either in any of SEQ ID NOS: 25–48 are also within the scope of the invention.

The present invention further pertains to recombinant forms of the subject CDK4-binding proteins which are encoded by genes derived from an organism and which have amino acid sequences evolutionarily related to a subject CDK4-binding protein of any of SEQ ID NOS: 25–48. Such recombinant CDK4-binding proteins preferably are capable of functioning in one of either role of an agonist or antagonist of at least one biological activity of the present CDK4-BPs. The term "evolutionarily related to", with respect to amino acid sequences of the present recombinant CDK4-binding proteins, refers to CDK4-binding proteins having amino acid sequences which have arisen naturally, as well as mutational variants of CDK4-binding proteins which are derived, for example, by combinatorial mutagenesis. Such evolutionarily derived CDK4-binding protein preferred by the present invention are at least 60% homologous, more preferably 70% homologous and most preferably 80% homologous with an amino acid sequence shown in any of SEQ ID NOS: 25–48. Polypeptides having at least about 90%, more preferably at least about 95%, and most preferably at least about 98–99% homology with a sequence shown in any of SEQ ID NOS: 25–48 are also within the scope of the invention.

The present invention further pertains to methods of producing the subject CDK4-binding proteins. For example, a host cell transfected with a nucleic acid vector directing expression of a nucleotide sequence encoding one of the subject CDK4-binding proteins can be cultured under appropriate conditions to allow expression of the peptide to occur. The peptide may be secreted and isolated from a mixture of host cells and medium. Alternatively, the peptide may be retained cytoplasmically and the cells harvested, lysed and the protein isolated. A cell culture includes host cells, media and other byproducts. Suitable media for cell culture are well known in the art. The recombinant CDK4-BP peptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant CDK4-binding protein is a fusion protein containing a domain which facilitates its purification, such as a CDK4-BP-GST fusion protein.

This invention also pertains to a host cell transfected to express a recombinant form of at least one of the subject CDK4-binding proteins. The host cell may be any prokaryotic or eukaryotic cell. Thus, a nucleotide sequence derived from the cloning of the CDK4-binding proteins of the present invention, encoding all or a selected portion of a protein, can be used to produce a recombinant form of a CDK4-BP via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant CDK4-binding proteins, or portions thereof, by microbial means or tissue-culture technology in accord with the subject invention.

The recombinant CDK4-BP gene can be produced by ligating a nucleic acid encoding a subject CDK4-binding protein, or a portion thereof, into a vector suitable for expression in either prokaryotic cells, eukaryotic cells, or both. Expression vehicles for production of recombinant forms of the subject CDK4-binding proteins include plasmids and other vectors. For instance, suitable vectors for the expression of a CDK4-BP include plasmids of the types: pBR322-derived plasmids, pEMBL-derived plasmids, pEX-derived plasmids, pBTac-derived plasmids and pUC-derived plasmids for expression in prokaryotic cells, such as E. coli. In an illustrative embodiment, a CDK4-binding protein is produced recombinantly utilizing an expression vector generated by sub-cloning a gene encoding the protein from the pJG4-5-CDKBP library (ATCC deposit no. 75788) using, for example, primers based on 5' or 3' sequences of the particular pJG4-5 gene (see Table 1) and/or primers based on the flanking plasmid sequences of the pJG4-5 plasmid (e.g. SEQ ID Nos. 71 and 72).

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in *Experimental Manipulation of Gene Expression*, ed. M. Inouye Academic Press, p. 83). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning: A Laboratory Manual*, 2nd Ed., ed. by Sambrook, Fritsch and Maniatis (Cold Spring Harbor Laboratory Press: 1989) Chapters 16 and 17. In some instances, it may be desirable to express the recombinant CDK4-binding protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a portion of one of the subject CDK4-binding proteins is desired, i.e. a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing CDK4-BP-derived polypeptides in a host which produces MAP (e.g., *E. coli* or CM89 or *S. cerevisiae*), or in vitro by use of purified MAP (e.g., procedure of Miller et al. supra).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a CDK4-binding protein. For example, the VP6 capsid protein of rotavirus can be used as an immunologic carrier protein for portions of the CDK4-BP polypeptide, either in the monomeric form or in the form of a viral particle. The nucleic acid sequence corresponding to a portion of a subject CDK4-binding protein to which antibodies are to be raised can be incorporated into a fusion gene construct which includes coding sequences for a late vaccinia virus structural protein to produce a set of recombinant viruses expressing fusion proteins comprising a portion of the protein CDK4-BP as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a subject CDK4-binding protein and the poliovirus capsid protein can be created to enhance immunogenicity of the set of polypeptide antigens (see, for example, EP Publication No. 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized to generate an immunogen, wherein a desired portion of a subject CDK4-binding protein is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of the subject CDK4-binding proteins can also be expressed and presented by bacterial cells.

In addition to utilizing fusion proteins to enhance immunogenicity, it is widely appreciated that fusion proteins can also facilitate the expression of proteins, such as any one of the CDK4-binding proteins of the present invention. For example, a CDK4-binding protein of the present invention can be generated as a glutathione-S-transferase (GST-fusion protein). Such GST fusion proteins can enable easy purification of a CDK4-binding protein, such as by the use of glutathione-derivativized matrices (see, for example, *Current Protocols in Molecular Biology*, eds. Ausabel et al. (New York: John Wiley & Sons, 1991)). In another embodiment, a fusion gene coding for a purification leader sequence, such as a poly(His)/enterokinase cleavage site sequence at the N-terminus of the desired portion of a CDK4-binding protein, can allow purification of the poly (His)-expressed CDK4-BP-fusion protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Another aspect of the invention pertains to isolated polypeptides having an activity of one of the subject CDK4-binding proteins, or which are antagonists of at least one of the biological activities of the subject CDK4-BPs. In preferred embodiments, a biological activity of a CDK4-BP protein can include: an ability to bind to a CDK, e.g. CDK4, CDK6 and/or CDK5; an ability to regulate a eukaryotic cell cycle, e.g. a mammalian cell cycle, e.g., a human cell cycle; an ability to regulate proliferation/cell growth of a eukaryotic cell, e.g. a mammalian cell, e.g., a human cell; an ability to regulate progression of a eukaryotic cell through G1 phase, e.g. regulate progression of a mammalian cell from $G_0$ phase into $G_1$ phase, e.g. regulate progression of a mammalian cell through $G_1$ phase; an ability to regulate the kinase activity of a cyclin dependent kinase (cdk), e.g. a cdk active in G1 phase, e.g. CDK4, e.g. CDK6, e.g. an ability to regulate phosphorylation of an Rb or Rb-related protein by CDK4; an ability to regulate the effects of mitogenic stimulation on cell-cycle progression, e.g. regulate contact inhibition, e.g. mediate growth factor- or cytokine-induced mitogenic stimulation, e.g. regulate paracrine-responsiveness. Certain of the CDK4-binding proteins of the present invention may also have biological activities which include an ability to suppress tumor cell growth, e.g. in a tumor cell which has lost contact inhibition, e.g. in tumor cells which have paracrine feedback loops. Other biological activities of the subject CDK4-binding proteins are described herein or will be reasonably apparent to those skilled in the art. A polypeptide having at least one biological activity of one of the subject CDK4-binding proteins may differ in amino acid sequence from the sequence of that protein shown in the appended Sequence Listing, but such differences result in a modified protein which functions in the same or similar manner as a native CDK4-binding protein or which has the same or similar characteristics of a native CDK4-binding protein. Various modifications of a CDK4-binding protein of the present invention to produce these and other functionally equivalent peptides are described in detail herein. The term peptide, as used herein, refers to peptides, proteins, and polypeptides.

The present invention also makes available isolated CDK4-binding proteins which are isolated from, or otherwise substantially free of other cellular or viral proteins normally associated with the protein, e.g. other cell-cycle proteins, e.g. human CDKs. The term "substantially free of other cellular or viral proteins" (also referred to herein as "contaminating proteins") is defined as encompassing CDK4-BP preparations comprising less than 20% (by dry weight) contaminating protein, and preferably comprises less than 5% contaminating protein. Functional forms of the subject CDK4-binding proteins can be prepared, for the first time, as purified preparations by using, for example, a cloned gene as described herein. By "purified", it is meant, when referring to a peptide or DNA or RNA sequence, that the indicated molecule is present in the substantial absence of other biological macromolecules, such as other proteins (e.g. other CDK4-BPs, or CDKs). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding the subject CDK4-BP preferably includes no more than 10 kilobases (kb) of nucleic acid sequence which naturally immediately flanks the CDK4-BP gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Moreover, isolated peptidyl portions of the subject CDK4-binding proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a CDK4-binding protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a CDK4-binding protein activity, such as by microinjection assays.

It is also possible to modify the structure of the subject CDK4-binding proteins for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the CDK4-binding proteins described in more detail herein. Such modified polypeptides can be produced, for instance, by amino acid substitution, deletion, or addition. Moreover, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing= cysteine and methionine. (see, for example, *Biochemistry*, 2nd ed, Ed. by L. Stryer, W. H. Freeman and Co.:1981). Whether a change in the amino acid sequence of a peptide results in a functional CDK4-BP homolog can be readily determined by assessing the ability of the variant peptide to produce a response in cells in a fashion similar to the wild-type CDK4-BP. Peptides in which more than one replacement has taken place can readily be tested in the same manner.

This invention further contemplates a method of generating sets of combinatorial mutants of any one of the presently disclosed CDK4-binding proteins, as well as truncation mutants, and is especially useful for identifying potentially useful variant sequences which are useful in regulating cell growth of differentiation. One purpose for screening such combinatorial libraries is, for example, to isolate novel CDK4-BP homologs which function i the capacity of one of either an agonists or an antagonist of the biological activities of the wild-type ("authentic") protein, or alternatively, which possess novel activities all together. To illustrate, homologs of the clone #225 kinase can be engineered by the present method to provide catalytically inactive enzymes which maintain binding to CDK4 but which act antagonistically to the role of the native kinase in eukaryotic cells, e.g. in regulating cell growth, e.g. in regulating paracrine signal transduction. Such proteins, when expressed from recombinant DNA constructs, can be used in gene therapy protocols.

Likewise, mutagenesis can give rise to CDK4-BP homologs which have intracellular half-lives dramatically different than the corresponding wild-type protein. For example, the altered protein can be rendered either more stable or less stable to proteolytic degradation or other cellular process which result in destruction of, or otherwise inactivation of, the authentic CDK4-binding protein. Such CDK4-BP homologs, and the genes which encode them, can be utilized to alter the envelope of expression for the particular recombinant CDK4 binding proteins by modulating the half-life of the recombinant protein. For instance, a short half-life can give rise to more transient biological effects associated with a particular recombinant CDK4-binding protein and, when part of an inducible expression system, can allow tighter control of recombinant CDK4-BP levels within the cell. As above, such proteins, and particularly their recombinant nucleic acid constructs, can be used in gene therapy protocols.

In an illustrative embodiment of this method, the amino acid sequences for a population of CDK4-BP homologs or other related proteins are aligned, preferably to promote the highest homology possible. Such a population of variants can include, for example, CDK4-BP homologs from one or more species, or CDK4-BP homologs from the same species but which differ due to mutation. Amino acids which appear at each position of the aligned sequences are selected to create a degenerate set of combinatorial sequences.

In a preferred embodiment, the combinatorial CDK4-BP library is produced by way of a degenerate library of genes encoding a library of polypeptides which each include at least a portion of potential CDK4-BP sequences. A mixture of synthetic oligonucleotides can be enzymatically ligated into gene sequences such that the degenerate set of potential CDK4-BP sequences are expressible as individual polypeptides, or alternatively, as a set of larger fusion proteins (e.g. for phage display) containing the set of CDK4-BP sequences therein.

There are many ways by which the library of potential CDK4-BP homologs can be generated from a degenerate oligonucleotide sequence. Chemical synthesis of a degenerate gene sequence can be carried out in an automatic DNA synthesizer, and the synthetic genes then can be ligated into an appropriate gene for expression. The purpose of a degenerate set of genes is to provide, in one mixture, all of the sequences encoding the desired set of potential CDK4-BP sequences. The synthesis of degenerate oligonucleotides is well known in the art (see for example, Narang, S. A. (1983) *Tetrahedron* 39:3; Itakura et al. (1981) *Recombinant DNA, Proc 3rd Cleveland Sympos. Macromolecules*, ed. A. G. Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations and for screening cDNA libraries for gene products having a certain property. Such techniques will be generally adaptable for rapid screening of the gene libraries generated by the combinatorial mutagenesis of CDK4-BP homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate CDK4-BP sequences created by combinatorial mutagenesis techniques.

In one screening assay, the candidate CDK4-BP gene products are displayed on the surface of a cell or viral particle, and the ability of particular cells or viral particles to bind a CDK4 (or CDK6) protein via this gene product is detected in a "panning assay". For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, fluorescently labeled CDK4 can be used to score for potentially functional CDK4-BP homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al, PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

In an illustrative embodiment, the recombinant phage antibody system (RPAS, Pharmacia Catalog number 27-9400-01) can be easily modified for use in expressing and screening CDK4-BP combinatorial libraries. For instance, the pCANTAB 5 phagemid of the RPAS kit contains the gene which encodes the phage gIII coat protein. The CDK4-BP combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate CDK4-BP gene insert. The resulting recombinant phage contain phagemid DNA encoding a specific candidate CDK4-BP, and display one or more copies of the corresponding fusion coat protein. Those phage-displayed candidate CDK4-BPs which retain the ability to bind CDK4 are selected or enriched by panning with CDK4. For instance, the phage library can be panned on glutathione-immobilized CDK4-GST fusion proteins, and unbound phage washed away from the cells. The bound phage is then isolated, and if the recombinant phage express at least one copy of the wild type gIII coat protein, they will retain their ability to infect *E. coli*. Thus, successive rounds of reinfection of *E. coli*, and panning will greatly enrich for CDK4-BP homologs which can retain an ability to bind CDK4 (or other CDKs) and which can subsequently be screened for further biological activities in order to differentiate agonists and antagonists.

In light of the present disclosure, other forms of mutagenesis generally applicable will be apparent to those skilled in the art in addition to the aforementioned combinatorial mutagenesis approach. For example, homologs of the subject CDK4-binding proteins (both agonist and antagonist forms) can be generated and screened using, for example, alanine scanning mutagenesis and the like (Ruf et al. (1994)

*Biochemistry* 33:1565–1572; Wang et al. (1994) *J Biol Chem* 269:3095–3099; Balint et al. (1993) *Gene* 137:109–118; Grodberg et al. (1993) *Eur J Biochem* 218:597–601; Nagashima et al. (1993) *J Biol Chem* 268:2888–2892; Lowman et al. (1991) *Biochemistry* 30:10832–10838; and Cunningham et al. (1989) *Science* 244:1081–1085); by linker scanning mutagenesis (Gustin et al. (1993) *Virology* 193:653–660; Brown et al. (1992) *Mol Cell Biol* 12:2644–2652; McKnight et al. (1982) *Science* 232:316); or by saturation mutagenesis (Meyers et al. (1986) *Science* 232:613).

An important goal of the present invention is to provide reduction of the subject CDK4-binding proteins to generate CDK4-BP mimetics, e.g. peptide or non-peptide agents, which are able to disrupt binding of a CDK4-BP of the present invention with cyclin-dependent kinase particularly CDK4 or CDK6. Thus, such mutagenic techniques are particularly useful to map the determinants of the CDK4-BP which participate in protein-protein interactions involved in, for example, binding of the subject CDK4-binding protein to CDK4. To illustrate, the critical residues of a subject CDK4-binding protein which are involved in molecular recognition of CDK4 can be determined and used to generate a CDK4-BP-derived peptidomimetics which competitively inhibit binding of the CDK4-BP with CDK4 (see, for example, "Peptide inhibitors of human papillonavirus protein binding to retinoblastoma gene protein" European patent applications EP-412,7624 and EP-531,080A). By employing, for example, scanning mutagenesis to map the amino acid residues of a particular CDK4-BP involved in binding CDK4, peptidomimetic compounds (e.g. diazepine or isoquinoline derivatives) can be generated which mimic those residues in binding to CDK4, and which therefore can inhibit binding of the CDK4-BP to CDK4 and thereby interfere with the regulation of CDK4.

Another aspect of the invention pertains to an antibody specifically reactive with one of the subject CDK4-binding proteins. For example, by using immunogens derived from the present activity CDK4-binding proteins, based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or a rabbit can be immunized with an immunogenic form of the peptide (e.g., CDK4-binding protein or an antigenic fragment which is capable of eliciting an antibody response). Techniques for conferring immunogenicity on a protein or peptide include conjugation to carriers or other techniques well known in the art. An immunogenic portion of the subject CDK4-binding proteins can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the CDK4-binding proteins of the present invention, e.g. antigenic determinants of a protein represented by one of SEQ ID NOS: 25–48 or a closely related human or non-human mammalian homolog (e.g. 90 percent homologous, more preferably at least 95 percent homologous). In yet a further preferred embodiment of the present invention, the anti-CDK4-BP antibodies do not substantially cross react (i.e. react specifically) with a protein which is: e.g. less than 90 percent homologous to one of SEQ ID NOS: 25–48; e.g. less than 95 percent homologous with one of SEQ ID NOS: 25–48; e.g. less than 98–99 percent homologous with one of SEQ ID NOS: 25–48. By "not substantially cross react", it is meant that the antibody has a binding affinity for a nonhomologous protein (e.g. CDK4) which is less than 10 percent, more preferably less than 5 percent, and even more preferably less than 1 percent, of the binding affinity of that antibody for a protein of SEQ ID NOS: 25–48.

Following immunization, anti-CDK4-BP antisera can be obtained and, if desired, polyclonal anti-CDK4-BP antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with a CDK4-binding protein of the present invention and monoclonal antibodies isolated from a culture comprising such hybridoma cells.

The term antibody as used herein is intended to include fragments thereof which are also specifically reactive with one of the subject CDK4-binding protein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-CDK4-BP portion.

Both monoclonal and polyclonal antibodies (Ab) directed against the subject CDK4-BP or CDK4-BP variants, and antibody fragments such as Fab' and F(ab')$_2$, can be used to block the action of a subject CDK4-BP and allow the study of the role of a particular CDK4 binding protein of the present invention in the normal cellular function of the subject CDK4-binding protein, e.g. by microinjection of anti-CDK4BP antibodies of the present invention.

Antibodies which specifically bind CDK4-BP epitopes can also be used in immunohistochemical staining of tissue samples in order to evaluate the abundance and pattern of expression of each of the subject CDK4-binding protein. Anti-CDK4-BP antibodies can be used diagnostically in immuno-precipitation and immuno-blotting to detect and evaluate CDK4-BP levels in tissue or bodily fluid as part of a clinical testing procedure. Likewise, the ability to monitor CDK4-BP levels in an individual can allow determination of the efficacy of a given treatment regimen for an individual afflicted with a disorder. The level of CDK4-BP can be measured in cells found in bodily fluid, such as in samples of cerebral spinal fluid, or can be measured in tissue, such as produced by biopsy. Diagnostic assays using anti-CDK4-BP antibodies can include, for example, immunoassays designed to aid in early diagnosis of a neoplastic or hyperplastic disorder, e.g. the presence of cancerous cells in the sample, e.g. to detect cells in which a lesion of the CDK4-BP gene has occurred.

Another application of anti-CDK4-BP antibodies is in the immunological screening of cDNA libraries constructed in expression vectors such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject CDK4-BP can then be detected with antibodies, as, for example, reacting nitrocellulose filters lifted from infected plates with anti-CDK4-BP antibodies. Phage, scored by this assay, can then be isolated from the infected plate. Thus, the presence of CDK4-BP homologs can be detected and cloned from other sources, and alternate isoforms (including splicing variants) can be detected and cloned from human sources.

Moreover, the nucleotide sequence determined from the cloning of the subject CDK4-binding proteins from a human cell line will further allow for the generation of probes designed for use in identifying CDK4-BP homologs in other human cell types, as well as CDK4-BP homologs from other animals. For instance, the present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of one of SEQ ID Nos. 1–24 and 49–66, or naturally occurring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a CDK4-BP nucleic acid in a sample of cells isolated from a patient; e.g. measuring a CDK4-BP mRNA level in a cell; e.g. determining whether a genomic CDK4-BP gene has been mutated or deleted. As described below, the probe can be generated from the pJG4-5-CDKBP clones of ATCC deposit no. 75788.

The nucleotide probes of the present invention will permit genomic mapping of the genes for each of the subject CDK4-binding proteins employing standard protocols as, for example, fluorescent in situ hybridzation ("FISH"; see Demetrick et al. (1994) Cytogenet Cell Genet 66:72–74; Demetrick et al. (1993) Genomics 18:144–147; and DeMarini et al. (1991) Environ Mol Mutagen 18:222–223) or the use of somatic cell hybrids.

In addition, nucleotide probes can be generated from the cloned sequence of the subject CDK4-binding proteins, which allow for histological screening of intact tissue and tissue samples for the presence of a CDK4-BP mRNA. Similar to the diagnostic uses of anti-CDK4-BP antibodies, the use of probes directed to CDK4-BP mRNAs, or to genomic CDK4-BP sequences, can be used for both predictive and therapeutic evaluation of allelic mutations which might be manifest in, for example, neoplastic or hyperplastic disorders (e.g. unwanted cell growth). Used in conjunction with anti-CDK4-BP antibody immunoassays, the nucleotide probes can help facilitate the determination of the molecular basis for a developmental disorder which may involve some abnormality associated with expression (or lack thereof) of a CDK4-binding protein. For instance, variation in CDK4-BP synthesis can be differentiated from a mutation in the CDK4-BP coding sequence.

For example, the present method provides a method for determining if a subject is at risk for a disorder characterized by unwanted cell proliferation. In preferred embodiments, the subject method can be generally characterized as comprising detecting, in a tissue of the subject (e.g. a human patient), the presence or absence of a genetic lesion characterized by at least one of (i) a mutation of a gene encoding one of the subject CDK4-BPs or (ii) the mis-expression of a subject CDK4-BP gene. To illustrate, such genetic lesions can be detected by ascertaining the existence of at least one of (i) a deletion of one or more nucleotides from a subject CDK4-BP gene, (ii) an addition of one or more nucleotides to such a CDK4-BP gene, (iii) a substitution of one or more nucleotides of a CDK4-BP gene, (iv) a gross chromosomal rearrangement of one of the subject CDK4-BP genes, (v) a gross alteration in the level of a messanger RNA transcript of a CDK4-BP gene, (vi) the presence of a non-wild type splicing pattern of a messanger RNA transcript of a CDK4-BP gene, and (vii) a non-wild type level of a CDK4-binding protein. In one aspect of the invention, there is provided a probe/primer comprising an oligonucleotide containing a region of nucleotide sequence which is capable of hybridizing to a sense or antisense sequence of any of SEQ ID Nos: 1–24 and 49–70 or naturally occurring mutants thereof, or 5' or 3' flanking sequences or intronic sequences naturally associated with the subject CDK4-BP genes or naturally occurring mutants thereof. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR) (see, e.g. U.S. Pat. Nos. 4,683,195 and 4,683,202), or, alternatively, in a ligation chain reaction (LCR) (see, e.g., Landegran et al. (1988) Science 241:1077–1080; and Nakazawa et al. (1944) PNAS 91:360–364), the later of which can be particularly useful for detecting point mutations in the CDK4-BP gene. Alternatively, the level of CDK4-binding protein can detected in an immunoassay.

Also, the use of anti-sense techniques (e.g. microinjection of antisense molecules, or transfection with plasmids whose transcripts are anti-sense with regard to a CDK4-BP mRNA or gene sequence) can be used to disrupt expression of the naturally occurring gene and thus employed to investigate role of each of the subject CDK4-BP in cell growth, proliferation and differentiation in transformed cells, e.g. tumor cells, as well as the normal cellular function of each of the novel CDK4-BPs. Such techniques can be utilized in cell culture, but can also be used in the creation of transgenic animals.

Furthermore, by making available purified and recombinant CDK4-binding proteins, the present invention facilitates the development of assays which can be used to screen for drugs which are either agonists or antagonists of the normal cellular function of the subject CDK4-binding proteins. In one embodiment, the assay is derived to score for the ability of a compound to inhibit binding between a CDK4-BP and a CDK, e.g. CDK4. A variety of assay formats will suffice and, in light of the present invention, will be readily apparent to the skilled artisan. For example, in one such screening assay the compound of interest is contacted with an isolated and purified CDK4-binding protein of the present invention. The mixture of the compound and CDK4-BP is then added to a composition containing the CDK which does not contain CDK4-BP. Detection and quantification of labelled CDK/CDK4-BP complexes provides a means for determining the compound's efficacy at inhibiting complex formation between the CDK and the subject CDK4-BP. Conveniently, a control assay is also performed to provide a baseline for comparison. In the control assay, isolated and purified CDK4-BP is added to a composition containing the CDK, and the formation of CDK/CDK4-BP complex is quantitated in the absence of the test compound.

Complex formation between the CDK4-BP and a CDK may be detected by a variety of other methods as well. For example, glutathione S-transferase-CDK4 (GST-CDK4) fusion proteins are adsorbed onto glutathione sepharose beads which are then combined with an $^{35}$S-labeled CDK4-binding protein and incubated under conditions conducive to complex formation, e.g., at 4° C. in a buffer of 25 mM Tris-HCl (pH 7.2), 50 mM NaCl and 0.2% NP-40. Following incubation, the beads are washed to remove any unbound CDK4-BP, and the sepharose bead-bound radiolabel determined directly (e.g. beads placed in scintilant), or in the superntantant after the CDK4/CDK4-BP complexes are dissociated (e.g. by treatment with DTT). The supernatant containing the complexes can optionally be seperated by SDS-PAGE gel before detection.

Additionally, the subject CDK4+ binding protein can be used to generate an interaction trap assay, as described in the examples below (see also, U.S. Pat. No. 5,283,317; Zervos et al. (1993) Cell 72:223–232; Madura et al. (1993) J Biol Chem 268:12046–12054; Bartel et al. (1993) Biotechniques 14:920–924; and Iwabuchi et al. (1993) Oncogene 8:1693–1696), for subsequently detecting agents which disrupt binding of the CDK4-BP to a CDK or other cell cycle protein. The interaction trap assay relies on reconstituting in vivo a fuctional transcriptional activator protein from two separate fusion proteins, one of which comprises the DNA-binding domain of a transcriptional activator fused to a CDK, such as CDK4 or CDK6. The second fusion protein comprises a transcriptional activation domain (e.g. able to initiate RNA polymerase transcription) fused to one of the subject CDK4-binding proteins. When the CDK4 and CDK4-binding protein interact, the two domains of the transcriptional activator protein are brought into sufficient proximity as to cause transcription of a reporter gene. In an illustrative embodiment, Saccharomyces cerevisiae YPB2 cells are transformed simultaneously with a plasmid encoding a GAL4db-CDK4 fusion and with a plasmid encoding the GAL4ad domain fused to a subject CDK4-BP. Moreover, the strain is transformed such that the GAL4-responsive promoter drives expression of a phenotypic marker. For example, the ability to grow in the absence of histidine can depends on the expression of the HIS3 gene. When the HIS3 gene is placed under the control of a GAL4-responsive promoter, relief of this auxotrophic phenotype indicates that a functional GAL4 activator has been reconstituted through the interaction of CDK4 and the CDK4-BP. Thus, agent able to inhibit CDK4-BP interaction with CDK4 will result in yeast cells unable to growth in the absence of histidine. Alternatively, the phenotypic marker (e.g. instead of the HIS3 gene) can be one which provides a negative selection when expressed such that agents which disrupt CDK4/CDK4-BP interactions confer positive growth selection to the cells.

Furthermore, it will be possible to perform such assays as differential screening assays, which permit comparison of the effects of a drug on a number of different complexes formed between the CDK4-binding protein and other cell-cycle regulatory proteins, e.g. other CDKs. For instance, each of the above assays can be run with a subject CDK4-BP and each of CDK4, CDK5 and CDK6. In side-by-side comparison, therefore, agents can be chosen which selec- tively effect the formation of, for example, the CDK-BP/CDK4 complex without substantially interferring with the other CDK complexes.

Moreover, inhibitors of the enzymatic activity of any of the subject CDK-binding proteins which are enzymes, e.g. a kinase, e.g. an isopeptidase, e.g. a protease, can be identified using assays derived from measuring the ability of an agent to inhibit catalytic converstion of a substrate by the subject proteins.

In another aspect, the invention features transgenic non-human animals which express a recombinant CDK4-BP gene of the present invention, or which have had one or more of the subject CDK4-BP gene(s), e.g. heterozygous or homozygous, disrupted in at least one of the tissue or cell-types of the animal.

In another aspect, the invention features an animal model for developmental diseases, which has a CDK4-BP allele which is mis-expressed. For example, a mouse can be bred which has a CDK4-BP allele deleted, or in which all or part of one or more CDK4-BP exons are deleted. Such a mouse model can then be used to study disorders arising from mis-expressed CDK4-BP genes.

Exemplification

Manipulation of E. coli, yeast and DNA was by standard methods

Interaction Trap

A general transcription-based selection for protein-protein interactions was used to isolate cDNA which encode proteins able to bind to CDK4. Development of the "interaction trap assay" or ITS, is described in, for example, Gyuris et al. (1993) Cell 75:791–803; Chien et al. (1991) PNAS 88:9578–9582; Dalton et al. (1992) Cell 68:597–612; Durfee et al. (1993) Genes Dev 7:555–569; Vojteck et al. (1993) Cell 74:205–214; Fields et al. (1989) Nature 340:245–246; and U.S. Ser. No. 5,283,173). As carried out in the present invention, the interaction trap comprises three different components: a fusion protein that contains the LexA DNA-binding domain and that is known to be transcriptionally inert (the "bait"); reporter genes that have no basal transcription and whose transcriptional regulatory sequences are dependent on binding of LexA; and the proteins encoded by an expression library, which are expressed as chimeras and whose amino termini contrain an activation domain and other useful moieties (the "fish"). Briefly, baits were produced constitutively from a 211 HIS3+ plasmid under the control of the ADH1 promoter and contained the LexA carboxy-terminal oligomerization region. Baits were made in pLexA(1-202)+pl (described in Ruden et al. Nature (1991) 350:250–252; and Gyuris et al. Cell (1993) 75:791–803) after PCR amplification of the bait coding sequences from the second amino acid to the Stop codon, except for p53 where the bait moiety starts at amino acid 74. Using the PCR primers described in Table I, CDK2 and CDK3 were cloned as EcoR1-BamH1 fragments; CDK4, cyclin D1, cyclin D2, Cyclin E as EcoR1-SalI fragments; CDK5, CDK6, Cdi1 as EcoR1-XhoI fragments; and retinoblastoma (pRb), mutRb(Δ702–737), p53 and cyclin C as BamH1-SalI fragments. When EcoR1 is used, there are two amino acid inserted (EF) between the last amino acid of LexA and the bait moieties. BamH1 fusion results in five amino acid insertion (EFPGI) between LexA and the fused protein.

TABLE 1

PCR primers

CDK2:
5'-GGC GGC CGC GAA TTC GAG AAC TTC C AAA AGG TGG AAA AG-3'
5'-GC GGC CGC GGA TCC AGG CTA TC AGA GTC GAA GAT GGG GTA C-3'

CDK3:
5' GC GGC CGC GAA TTC GAA GCT GGA GGA GCA ACC GGG AGC-3'
5'-GC GGC CGC GGA TCC TC AAT GGC GGA ATC GCT GCA GCA C-3'

CDK5:
5'-GC GGC GGC GTC GAC C AGA AAT ACG AGA AAC T GGA AAA G-3'
5'-GC GGC GGC GTC GAC C GGG GCC TAG GGC GGA C AGA AGT C-3'

CDK6:
5'-GC GGC CGC GAA TTC GAG AAG GAC GGC CT GT GCC GC GCT-3'
5'-GC GGC GGC CTC GAG GAG GCC TC AGG CT GT ATT C AGC TC-3'

Cyclin C:
5'-GGC CGG CC GGG ATC CT TGT CGC TCC GCG GCT GCT CCG GCT G-3'
5'-GC GGC CGC GTC GAC GTT TT AAG ATT GGC TGT AGC T AGA G-3'

Cyclin D1:
5'-GGC CGG CC GGA ATT C GAA CAC CAG CTC CT GT GCT GCG AAG-3'
5'-GC GGC CGC GTC GAC GCG CCC T CAG ATG TCC ACG TCC CGC-3'

Cyclin D2:
5'-GC GGC GGC GAA TTC GAG CTG CT GT GCC ACG AGG T GGA C-3'
5'-GC GGC GGC GAA TTC GAG CTG CT GT GCC ACG AGG T GGA C-3'

Cyclin E:
5'-GGC CGG CC GGA ATT C AAG GAG GAC GGC GGC GC GGA GTT C-3'
5'-GC GGC CGC GTC GAC GGG T GGT C ACG CC ATT T CCG GCC CG-3'

Cdi1:
5'-GC GGC CGC GAA TTC AAG CCG CCC AGT TC AAT ACA AAC AAG-3'
5'-GC GGC CGC CTC GAG ATT CCT TTA TCT TGA TAC AGA TCT TG-3'

Rb:
5'-GC GGC CGC GGA TCC AGC CGC CC AAA ACC CCC GAA AAA CG-3'
5'-GC GGC CGC GAA TTC CTC GAG CTC ATT TCT CTT CCT TGT TTG AGG-3' p53:
5'-GC GGC CGC GGA TCC AAG CCC TGC ACC AGC AGC TCC TAC A-3'
5'-GC GGC CGC GTC GAC T CAG TCT GAG TCA GGC CCT TCT GT-3'

Reports

The LexAop-LEU2 construction replaced the yeast chromosomal LEU2 gene. The other reporter, pRB1840, one of a series of LexAop-GAL1-lacZ genes (Brent et al. (1985) *Cell* 43:729-736; Kamens et al. (1990) *Mol Cell Biol* 10:2840-2847), was carried on a 2µ plasmid. Basal reporter transcription was extremely low, presumably owing both to the removal of the entire upstream activating sequence from both reporters and to the fact that LexA operators introduced into yeast promoters decrease their transcription (Brent and Ptashne (1984) *Nature* 312:612-615). Reporters were chosen to differ in sensitivity. The LEU2 reporter contained three copies of the high affinity LexA-binding site found upstream of *E. coli* colE1, which presumably bind a total of six dimers of the bait. In contrast, the lacZ gene contained a single lower affinity operator that binds a single dimer of the bait. The operators in the LEU2 reporter were closer to the transcription start point than they were in the lacZ reporter. These differences in the number, affinity, and operator position all contribute to that fact that the LEU2 reporter is more sensitive than the lacZ gene.

Expression Vectors and Library

Library proteins were expressed from pJG4-5, a member of a series of expression plasmids designed to be used in the interaction trap and to facilitate analysis of isolated proteins. These plasmids carry the 2µ replicator and the TRP1 marker. pJG4-5, shown in FIG. 1, directs the synthesis of fusion proteins. Proteins expressed from this vector possess the following features: galactose-inducible expression so that their synthesis is conditional, an epitope tag to facilitate detection, a nuclear localization signal to maximize intranuclear concentration to increase selection sensitivity, and an activation domain derived from *E. coli* (Ma and Ptashne (1987) *Cell* 57:113-119), chosen because its activity is not subject to known regulation by yeast proteins and because it is weak enough to avoid toxicity (Gill and Ptashne (1988) *Nature* 334:721-724; Berger et al. (1992) *Cell* 70:251-265) that might restrict the number or type of interacting proteins recovered. We introduced EcoRI-XhoI cDNA-containing fragments, which were generated from a quiescent normal fibroblast line (WI38), into the pJG4-5 plasmid.

CDK4 Interaction Trap

We began with yeast cells which contained LexAop-LEU2 and LexAop-lacZ reporters and the LexA-CDK4 bait. We introduced the WI38 cDNA library (in pJG4-5) into this strain. We recovered a number of transformants on glucose Ura$^-$ His$^-$ Trp$^-$ plates, scraped them, suspended them in approximately 20 ml of 65% glycerol, 10 mM Tris-HCl (pH 7.5), 10 mM MgCl$_2$, and stored the cells in 1 ml aliquots at $-80°$ C. We determined plating efficiency on galactose Ura$^-$ His$^-$ Trp$^-$ after growing 50 µl of cell suspension for 5 hr in 5 ml of YP medium, 2% galactose. For the selection, about $2 \times 10^7$ galactose-viable cells were plated on four standard circular 10 cm galactose Ura$^-$ His$^-$ Trp$^-$ Leu$^-$ plates after galactose induction. After 4 days at 30° C., LEU+ colonies appeared and were collected on glucose Ura⁻ His⁻ Trp⁻ master plates and retested on glucose Ura⁻ His⁻ Trp⁻ Leu⁻, galactose Ura⁻ His⁻ Trp⁻ Leu⁻, glucose X-Gal Ura⁻ His⁻ Trp⁻, and galactose X-Gal Ura⁻ His⁻ Trp⁻ plates. Of these, plasmid DNAs were rescued from colonies which showed galactose-dependent growth on Leu⁻ media and galactose-dependent blue color on X-Gal medium (Hoffman and Winston, (1987) Gene 57:267–272), introduced into E. coli KC8, and transformants collected on Trp⁻ ampicillin plates.

We classified library plasmids by restriction pattern on 1.8% agarose, 0.5×Tris-borate-EDTA gels after digestion with EcoRI and Xho1 and either AluI or HaeIII. We reintroduced those plasmids from each map class that contained the longest cDNAs into EGY48 derivatives that contained a panel of different baits, e.g. other CDKs, cyclins, p53, Rb, etc. As is evident from inspection of the data for this experiment (see FIG. 2), each of the subject CDK4-binding proteins displayed different binding affinities for other cell-cycle regulatory proteins. This finding is significant for a number of reasons. For example, in chosing a particular CDK4 interaction as a therapeutic target for drug design, therapeutic index concerns might cause selection of a CDK4-BP target which interacts primarily with CDK4 and much less with any other CDK. Alternatively, if desired, the ability of a particular CDK4-BP to bind multiple CDKs can be exploited in testing compounds in differential screening assays as described above. Thus, drugs which can alter the binding of, for example, a particular CDK4-BP to CDK4 but which have less effect on the same complexformed with CDK5, will presumably have a better therapeutic index with regard to neuronal side effects than a drug which interferes equally with both.

Furthermore, a deposit of each of these clones as a library of pJG4-5 plasmids (designated "pJG4-5-CDKBP") containing 24 different proteins isolated in the CDK4 interaction trap has been made with the American Type Culture Collection (Rockville, Md.) on May 26, 1994, under the terms of the Budapest Treaty. ATCC deposit No. 75788 has been assigned to the deposit. The cDNAs were inserted into this vector as EcoR1-Xho1 fragments. The EcoR1 adaptor sequence is 5'-GAATTCTGCGGCCGC-3' and the open reading frame encoding the interacting protein starts with the first G. With this deposit in hand, one of ordinary skill in the art can generate the subject recombinant CDK4-BP genes abd express recombinant forms of the subject CDK4-binding proteins. For instance, each of the CDK4-binding proteins of the present invention can be amplified from ATCC deposit no. 75788 by PCR using the following primers:

5'- TAC CAG CCT CTT GCT GAG TGG AGA -3' (SEQ ID No. 71)
5'- TAG ACA AGC CGA CAA CCT TGA TTG -3' (SEQ ID No. 72)

Moreover, it will be immediately evident to those skilled in the art that, in light of the guide to the 5' and 3' ends to each of the clones provided in Table 2, each individual clone of the ATCC deposit can be isolated using primers based on the nucleotide sequences provided by SEQ ID Nos. 1–24 and 49–70, or a combination of such primers and the primers of SEQ ID Nos. 71 and 72.

Isolated clones can be subcloned into expression vectors in order to produce a recombinant protein, or can be used to generate anti-sense constructs, or can be used to generate oligonucleotide probes. In an illustrative embodiment, oligonucleotide probes have been generated using the coding sequences for each of the clones of the subject ATCC deposit, and used in Southern hybridization and in situ hybridization assays to detect the pattern and abundance of expression of each of the CDK4-binding proteins.

Moreover, because each member of the ATCC deposit is a plasmid encoding a fusion protein identified from an interaction trap assay, the clone can be utilized directly from the deposit in a similar ITS employed as, for example, a drug screening assay, or alternatively, a mutagenesis assay for mapping CDK4 binding epitopes.

TABLE 2

Guide to pJG4-5-CDKBP

| Clone | Nucleotide | Peptide |
|---|---|---|
| 11 | SEQ ID No. 1 | SEQ ID No. 25 |
| 13 | SEQ ID No. 2 | SEQ ID No. 26 |
| 22 | SEQ ID No. 3 | SEQ ID No. 27 |
| 36 | SEQ ID No. 4 (5') SEQ ID No. 49 (3') | SEQ ID No. 28 (N-terminal) |
| 61 | SEQ ID No. 5 (5') SEQ ID No. 50 (3') | SEQ ID No. 29 (N-terminal) |
| 68 | SEQ ID No. 6 (5') SEQ ID No. 51 (3') | SEQ ID No. 30 (N-terminal) |
| 71 | SEQ ID No. 7 (full length) SEQ ID No. 69 (5') SEQ ID No. 70 (3') | SEQ ID No. 31 |
| 75 | SEQ ID No. 8 (5') SEQ ID No. 52 (3') | SEQ ID No. 32 (N-terminal) |
| 116 | SEQ ID No. 9 (full length) SEQ ID No. 67 (5') SEQ ID No. 68 (3') | SEQ ID No. 33 |
| 118 | SEQ ID No. 10 (5') SEQ ID NO. 55 (3') SEQ ID No. 55 (Internal) | SEQ ID No. 34 (N-terminal) |
| 121 | SEQ ID No. 11 (5') SEQ ID No. 56 (3') | SEQ ID No. 35 (N-terminal) |
| 125 | SEQ ID No. 12 (5') SEQ ID No. 57 (3') | SEQ ID No. 36 (N-terminal) |
| 127 | SEQ ID No. 13 | SEQ ID No. 37 |
| 165 | SEQ ID No. 65 | |
| 166 | SEQ ID No. 15 | SEQ ID No. 39 |
| 190 | SEQ ID No. 16 (5') SEQ ID No. 58 (3') | SEQ ID No. 40 (N-terminal) |
| 193 | SEQ ID No. 17 | SEQ ID NO. 41 |
| 216 | SEQ ID No. 18 (5') SEQ ID No. 59 (3') | SEQ ID NO. 42 |
| 225 | SEQ ID No. 19 (3') SEQ ID No. 24 (5') | SEQ ID No. 43 (C-terminal) SEQ ID No. 48 (N-terminal) |
| 227 | SEQ ID No. 20 (5') SEQ ID No. 61 (3') | SEQ ID No. 44 (N-terminal) |
| 267 | SEQ ID No. 21 (5') SEQ ID No. 62 (3') | SEQ ID No. 45 (N-terminal) |
| 269 | SEQ ID No. 22 (5') SEQ ID No. 63 (3') | SEQ ID No. 46 (N-terminal) |
| 295 | SEQ ID No. 23 (5') SEQ ID No. 64 (3') | SEQ ID No. 47 (N-terminal) |
| 297 | SEQ ID No. 14 | SEQ ID No. 38 |

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An assay for screening test compounds for an inhibitor of an interaction of a cyclin dependent kinase (CDK) with a CDK4-binding protein (CDK-BP) comprising i. combining a CDK and a CDK4-BP comprising an amino acid sequence selected from a group consisting of SEQ ID Nos. 25–48, under conditions wherein said CDK and said CDK4-BP are able to interact;

ii. contacting said combination with a test compound; and iii. detecting the formation of a complex comprising said CDK and said CDK4-BP, wherein a decrease in the formation of said complex in the presence of said test compound is indicative of an inhibitor of the interaction between said CDK and said CDK4-binding protein.

* * * * *